(12) United States Patent
Philippe et al.

(10) Patent No.: US 12,209,267 B2
(45) Date of Patent: *Jan. 28, 2025

(54) MICROBIAL PRODUCTION OF ROTUNDONE

(71) Applicant: MANUS BIO INC., Cambridge, MA (US)

(72) Inventors: Ryan N. Philippe, Cambridge, MA (US); Ajikumar Parayil Kumaran, Cambridge, MA (US); Christine Nicole S. Santos, Cambridge, MA (US); Jason Donald, Cambridge, MA (US); Stephen Sarria, Cambridge, MA (US)

(73) Assignee: Manus Bio Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/172,594

(22) Filed: Feb. 22, 2023

(65) Prior Publication Data

US 2023/0183760 A1 Jun. 15, 2023

Related U.S. Application Data

(63) Continuation of application No. 17/273,567, filed as application No. PCT/US2019/050004 on Sep. 6, 2019, now Pat. No. 11,618,908.

(60) Provisional application No. 62/727,815, filed on Sep. 6, 2018.

(51) Int. Cl.
| | |
|---|---|
| *C12P 7/26* | (2006.01) |
| *C12N 9/02* | (2006.01) |
| *C12N 9/04* | (2006.01) |
| *C12N 9/10* | (2006.01) |
| *C12N 9/88* | (2006.01) |
| *C12N 15/52* | (2006.01) |

(52) U.S. Cl.
CPC .............. *C12P 7/26* (2013.01); *C12N 9/0006* (2013.01); *C12N 9/0071* (2013.01); *C12N 9/1085* (2013.01); *C12N 9/88* (2013.01); *C12N 15/52* (2013.01); *C12Y 205/0101* (2013.01); *C12Y 402/03087* (2013.01)

(58) Field of Classification Search
None
See application file for complete search history.

(56) References Cited

U.S. PATENT DOCUMENTS

| | | | |
|---|---|---|---|
| 9,404,130 B2 | 8/2016 | Ajikumar et al. | |
| 9,796,980 B2 | 10/2017 | Ajikumar et al. | |
| 9,957,527 B2 | 5/2018 | Ajikumar et al. | |
| 10,463,062 B2 | 11/2019 | Philippe et al. | |
| 10,480,015 B2 | 11/2019 | Kumaran et al. | |
| 10,501,760 B2 | 12/2019 | Kumaran et al. | |
| 10,662,442 B2 | 5/2020 | Kumaran et al. | |
| 10,774,314 B2 | 9/2020 | Donald et al. | |
| 10,934,564 B2 | 3/2021 | Kumaran et al. | |
| 2015/0007368 A1 | 1/2015 | Saran et al. | |
| 2015/0218588 A1 | 8/2015 | Schalk et al. | |
| 2017/0356059 A1 | 12/2017 | Kino et al. | |
| 2018/0135081 A1 | 5/2018 | Kumaran et al. | |
| 2020/0299737 A1* | 9/2020 | Goeke | C12P 7/38 |
| 2021/0161092 A1 | 6/2021 | Kumaran et al. | |

FOREIGN PATENT DOCUMENTS

| | | | |
|---|---|---|---|
| JP | 2016154502 A | * | 9/2016 |
| JP | 2017525395 A | | 9/2017 |
| JP | 2017216974 A | | 12/2017 |
| WO | WO 2016029153 A1 | | 2/2016 |

OTHER PUBLICATIONS

EP patent application 17205361.3 filed Dec. 5, 2017. (Year: 2017).*
Drew, et al., "Two key polymorphisms in a newly discovered allele of the *Vitis vinifera* TPS24 gene are responsible for the production of the rotundone precursor α-guaiene", Journal of Experimental Botany.
Kato, et al., "Enhanced Production of δ-Guaiene, a Bicyclic Sesquiterpene Accumulated in Agarwood, by Coexpression of δ-Guaiene Synthase and Farnesyl Diphosphate Synthase Genes in *Escherichia coli*", Natural Product Communications, 2016, vol. 11, No. 9, 1221-1224.
Degenhardt, et al., "Monoterpene and sesquiterpene synthases and the origin of terpene skeletal diversity in plants," Phytochemistry, 2009, vol. 70, Issues 15-16, pp. 1621-1637.
GenBank, Accession No. JF289265, 2011, www.ncbi.nlm.nih.gov.
GenBank, Accession No. AMQ67166, 2016, www.ncbi.nlm.gov.
GenBank, Accession No. XM 002282452, 2016, www.ncbi.nlm.nih.gov.
GenBank, Accession No. A0A076U535, 2018, www.ncbi.nlm.nih.gov.
Kumeta, et al., "Genomic organization of δ-guaiene synthase genes in *Aquilaria crassna* and its possible use for the identification of *Aquilaria* species," J. Nat. Med., 2011, vol. 65, pp. 508-513.
Uniprot, Accession No. Q46856, 2017, www.uniprot.org.
Extended European Search Report for EP 19856874.3, dated Apr. 26, 2022, 10 pgs.

(Continued)

*Primary Examiner* — Todd M Epstein
(74) *Attorney, Agent, or Firm* — Morgan, Lewis & Bockius LLP

(57) ABSTRACT

The present disclosure provides methods and compositions for producing rotundone. In various aspects, the present disclosure provides enzymes, polynucleotides encoding said enzymes, and recombinant microbial host cells (or microbial host strains) for the production of rotundone. In some embodiments, the present disclosure provides microbial host cells for producing rotundone at high purity and/or yield, from either enzymatic transformation of α-guaiene, or from sugar or other carbon source. The present disclosure further provides methods of making products containing rotundone, including flavor or fragrance products, among others.

24 Claims, 13 Drawing Sheets

Specification includes a Sequence Listing.

(56) References Cited

OTHER PUBLICATIONS

Takase, et al., "Chtochrome P450 CYP71BE5 in grapevine (*Vitis vinifera* catalyzes the formation of the spicy aroma compound (−)-rotundone", Journal of Experimental Botany, 2016, vol. 67, No. 3, pp. 787-798.

Drew, et al. 'Two Key Polymorphisms in a Newly Discovered Allele of the *Vitis vinifera* TPS24 Gene are Responsible for the Production of the Rotundone Precursor alpha-guaiene', Journal of Experimental Botany, 2016, vol. 67, No. 3 pp. 799-808.

\* cited by examiner

FIG. 4

| Mutant | Fold improvement in α-guaiene |
|---|---|
| F406L | 1.71 |
| Y442L | 1.16 |
| I371L | 1.15 |
| M273L | 1.15 |
| S374A | 1.13 |
| I399V | 1.12 |
| R377V | 1.08 |
| L419T | 1.08 |
| F382L | 1.07 |
| R290K | 1.07 |
| F512L | 1.07 |
| K522D | 1.07 |
| F368M | 1.07 |
| T72I | 1.06 |
| E454K | 1.06 |
| V433I | 1.05 |
| Y381W | 1.05 |
| I298V | 1.04 |
| L297I | 1.03 |
| G268C | 1.02 |
| I343V | 1.02 |
| V311L | 1.02 |
| L446I | 1.01 |
| Q447V | 1.01 |
| E457H | 1.00 |
| I291V | 0.98 |
| P508R | 0.98 |
| I265V | 0.98 |
| I229L | 0.98 |
| S503M | 0.97 |
| Q530G | 0.97 |
| A544P | 0.95 |
| I443M | 0.94 |

| Mutant | Fold improvement in α-guaiene |
|---|---|
| V505L | 0.94 |
| W147L | 0.94 |
| V24I | 0.94 |
| A451F | 0.91 |
| Q447K | 0.89 |
| V111L | 0.89 |
| V506L | 0.88 |
| V459A | 0.88 |
| A266V | 0.87 |
| V532K | 0.87 |
| T145G | 0.86 |
| S504P | 0.86 |
| D528H | 0.86 |
| Y270F | 0.85 |
| E517D | 0.82 |
| T448S | 0.81 |
| R414M | 0.81 |
| E453Q | 0.81 |
| S224L | 0.77 |
| S527T | 0.76 |
| G339T | 0.73 |
| T25S | 0.72 |
| E431K | 0.71 |
| del_A354 | 0.67 |
| L423F | 0.67 |
| M519L | 0.64 |
| S400T | 0.58 |
| R490D | 0.49 |
| S397A | 0.40 |
| T295A | 0.39 |
| Y449H | 0.35 |
| M432I | 0.31 |

| Mutant | Fold improvement in α-guaiene |
|---|---|
| G531K | 0.27 |
| G401S | 0.25 |
| Q376F | 0.21 |
| I329L | 0.17 |
| M273H | 0.16 |
| I407A | 0.15 |
| S509I | 0.15 |
| A440C | 0.13 |
| V304A | 0.12 |
| G401C | 0.11 |
| K522D | 0.08 |
| S502P | 0.07 |
| R536F | 0.05 |
| A275V | 0.05 |
| L288F | 0.03 |
| L516I | 0.03 |
| G523E | 0.02 |
| I398L | 0.02 |
| D521K | 0.02 |
| T301I | 0.02 |
| S529V | 0.01 |
| H276Y | 0.01 |
| L297V | 0.01 |
| Y375F | 0.01 |
| ins523_524_N | 0.01 |
| T533A | 0.00 |
| T533L | 0.00 |
| R463E | 0.00 |
| G339A | 0.00 |
| ins526_527_G | 0.00 |
| del_G531 | 0.00 |

FIG. 5

| Mutant | Fold improvement in % α-guaiene |
|---|---|
| I443M | 2.40 |
| F406L | 2.12 |
| F512L | 1.23 |

FIG. 10

```
NtKO    MDAILNLQTVPLGTALTIGGPAVALG-GISLWFLKEYVNDQKRKSSNFLPPLPEVPGLPV
LsKO    MDGVIDMQTIPLRTAIAIGGTAVALVVALYFWFLRSYASP-SHH-SNHLPPVPEVPGVPV
CcKO    ----MDMQSIP---AIAIGSTAVAIALGLFFWFFRRHVPDHIDH-PNHLPSVPEVPGIPV
AaKO    MDALTDMLQIPPATPITVAITTVTIAVAI-FLYIKSHASNHSRR-STHLPPVPEVPGVPV
KOeng   --MAWEYALIGLVVGIIIGAVAMR------WYLKSYTSARRSQ-SNHLPRVPEVPGVPL
HaKO    MDALTGMLPIPPATALAIGGTAIALAVAISFWFLRSYTSG---E-SNRLPRVPEVPGVPV
                  :   : :.  ::       ::. :.      .. ** :*****:*:

NtKO    IGNLLQLTEKKPHKTFTNWAETYGPIYSIKTGANTIVVLNTNELAKEAMVTRYSAISTRK
LsKO    LGNLLQLKEKKPYMTFTKWAEMYGPIYSIRTGATSMVVVSSNEIAKEVVVTRFPSISTRK
CcKO    LGNLLQLKEKKPYMTFTKWAETYGPIYSIRTGAISMVVVSSNAIAKEALVTRFPSISTRK
AaKO    LGNLLQLKEKKPYLTFTRWAQTYGAIYSIRTGATSMVVVSSSEIAKEAMVTRFSSISTRN
KOeng   LGNLLQLKEKKPYMTFTKWAATYGPIYSIKTGATSVVVVSSNEIAKEALVTRFQSISTRN
HaKO    LGNLLQLKEKKPYMTFTRWAETYGPIYSIRTGATSMVVVSSNEIAKEAFVTRFESISTRN
        :******.****: ***.**  **.****.*** ::**:.:. :***..***: :****:

NtKO    LTNALKILTCDKSIVAISDYDEFHKTVKRHVLTSVLGPNAQKRHRIHRDTLIENVSKQLH
LsKO    LSYALKVLTEDKSMVAMSDYHDYHKTVKRHILTAVLGPNAQKKFRAHRDTMMENVSNELH
CcKO    LSKALEVLTADKTMVAMSDYNDYHKTVKRHILTAVLGPNAQKKHRVHRDIMMQNLSNQLH
AaKO    LSKALTILTADKTMVAMSDYNDYHRTVKRHILTAMLGPNAQRKQRVHRDFMIENISKQLH
KOeng   LSKALKVLTADKQMVAMSDYDDYHKTVKRHILTAVLGPNAQKKHRIHRDIMMDNISTQLH
HaKO    LSKALKILTDDKTMVAMSDYNDYHKTVKRHILTAMLGPNAQKKHRIQRDIMMENLSNRLH
        *: ** :** **  :**:***  ::*.*****:**::******.. * :** :::*:*. **

NtKO    DLVRKYP-NEAVNLRKIFQSELFGLALKQALGKDIESIYVEGLDATLPREDVLKTLVLDI
LsKO    AFFEKNP-NQEVNLRKIFQSQLFGLAMKQALGKDVESIYVEDLETTMKREEIFEVLVVDP
CcKO    TFVQNSP-QEEVNLRKVFQSELFGLAMRQTMGKDESIYVEDLGTTMNRDEIFQVLVVDP
AaKO    AFVENSP-KEEVDLRKIFQSELFGLAMKQAVGKDVESLNVEDLGVTMKRDEIFQVLVVDP
KOeng   EFVKNNPEQEEVDLRKIFQSELFGLAMRQALGKDVESLYVEDLKITMNRDEILQVLVVDP
HaKO    AFVKTSTEQEEVDLREIFQSELFGLAMRQTMGKDVESIYVEDLKITMKRDEIFQVLVVDP
         :. .  ::  *:*::***:*****.*::***:**: *:.*  *: *:::::.**:*

NtKO    MEGAIDVDWRDFFPYLKWVPNKSFENRIQRKHLRREAVMKALIMEQRKRINSGEKLNSYI
LsKO    MMGAIEVDWRDFFPYLKWVPNKSFENIIHRMYTRREAVMKALIQEHKKRIASGENLNSYI
CcKO    LMGAIEVDWRDFFPYLKWIPNRNFENTIQQMYIRREAVMKALIQEHRKRIASGENLNSYI
AaKO    MMGAIEVDWRDFFPYLKWVPNKKFENTIQQMYIRRKAVMKALIKEHKKRIASGENLNSYI
KOeng   MMGAIDVDWRDFFPYLKWVPNKKFENTIQQMYIRREAVMKSLIKEQKKRIASGEKLNSYI
HaKO    MMGAIDVDWRDFFPYLKWVPNKKFENTIQQMYIRREAVMKALIKQHKERIASGEKLNSYI
         :***:************:**..*** *:. : **:****:**  :::.** ***:*****
```

NtKO (SEQ ID NO: 45)
LsKO (SEQ ID NO: 46)
CcKO (SEQ ID NO: 47)
KOeng (SEQ ID NO: 51)
AaKO (SEQ ID NO: 49)
HaKO (SEQ ID NO: 50)

FIG. 10 (contd.)

```
NtKO    MDAILNLQTVPLGTALTIGGPAVALG-GISLWFLKEYVNDQKRKSSNFLPPLPEVPGLPV
LsKO    MDGVIDMQTIPLRTAIAIGGTAVALVVALYFWFLRSYASP-SHH-SNHLPPVPEVPGVPV
CcKO    ----MDMQSIP---AIAIGSTAVAIALGLFFWFFRRHVPDHIDH-PNHLPSVPEVPGIPV
AaKO    MDALTDMLQIPPATPITVAITTVTIAVAI-FLYIKSHASNHSRR-STHLPPVPEVPGVPV
KOeng   --MAWEYALIGLVVGIIIGAVAMR------WYLKSYTSARRSQ-SNHLPRVPEVPGVPL
HaKO    MDALTGMLPIPPATALAIGGTAIALAVAISFWFLRSYTSG---E-SNRLPRVPEVPGVPV
         :        : :.  ::          ::. :.        .. ** :*****:*:
NtKO    IGNLLQLTEKKPHKTFTNWAETYGPIYSIKTGANTIVVLNTNELAKEAMVTRYSAISTRK
LsKO    LGNLLQLKEKKPYMTFTKWAEMYGPIYSIRTGATSMVVVSSNEIAKEVVVTRFPSISTRK
CcKO    LGNLLQLKEKKPYMTFTKWAETYGPIYSIRTGAISMVVVSSNAIAKEALVTRFPSISTRK
AaKO    LGNLLQLKEKKPYLTFTRWAQTYGAIYSIRTGATSMVVVSSSEIAKEAMVTRFSSISTRN
KOeng   LGNLLQLKEKKPYMTFTKWAATYGPIYSIKTGATSVVVVSSNEIAKEALVTRFQSISTRN
HaKO    LGNLLQLKEKKPYMTFTRWAETYGPIYSIRTGATSMVVVSSNEIAKEAFVTRFESISTRN
        :******.****: *** *** ** ***.***  ::**:.:. :***..***:  :****:
NtKO    LTNALKILTCDKSIVAISDYDEFHKTVKRHVLTSVLGPNAQKRHRIHRDTLIENVSKQLH
LsKO    LSYALKVLTEDKSMVAMSDYHDYHKTVKRHILTAVLGPNAQKKFRAHRDTMMENVSNELH
CcKO    LSKALEVLTADKTMVAMSDYNDYHKTVKRHILTAVLGPNAQKKHRVHRDIMMQNLSNQLH
AaKO    LSKALTILTADKTMVAMSDYNDYHRTVKRHILTAMLGPNAQRKQRVHRDFMIENISKQLH
KOeng   LSKALKVLTADKQMVAMSDYDDYHKTVKRHILTAVLGPNAQKKHRIHRDIMMDNISTQLH
HaKO    LSKALKILTDDKTMVAMSDYNDYHKTVKRHILTAMLGPNAQKKHRIQRDIMMENLSNRLH
        *: **  :** **  :**:***  ::*.*****:**::******.. * .:** *:*:.**
NtKO    DLVRKYP-NEAVNLRKIFQSELFGLALKQALGKDIESIYVEGLDATLPREDVLKTLVLDI
LsKO    AFFEKNP-NQEVNLRKIFQSQLFGLAMKQALGKDVESIYVKDLETTMKREEIFEVLVVDP
CcKO    TFVQNSP-QEEVNLRKVFQSELFGLAMRQTMGKDVESIYEDLGTTMNRDEIFQVLVVDP
AaKO    AFVENSP-KEEVDLRKIFQSELFGLAMKQAVGKDVESLNVEDLGVTMKRDEIFQVLVVDP
KOeng   EFVKNNPEQEEVDLRKIFQSELFGLAMRQALGKDVESLYVEDLKITMNRDEILQVLVVDP
HaKO    AFVKTSTEQEEVDLREIFQSELFGLAMRQTMGKDVESIYVEDLKITMKRDEIFQVLVVDP
         :.  .  :: *:**::***:*****:.*::***:**: *:.*  *: *:::::.**:*
NtKO    MEGAIDVDWRDFFPYLKWVPNKSFENRIQRKHLRREAVMKALIMEQRKRINSGEKLNSYI
LsKO    MMGAIEVDWRDFFPYLKWVPNKSFENIIHRMYTRREAVMKALIQEHKKRIASGENLNSYI
CcKO    LMGAIEVDWRDFFPYLKWIPNRNFENTIQQMYIRREAVMKALIQEHRKRIASGENLNSYI
AaKO    MMGAIEVDWRDFFPYLKWVPNKKFENTIQQMYIRRKAVMKALIKEHKKRIASGENLNSYI
KOeng   MMGAIDVDWRDFFPYLKWVPNKKFENTIQQMYIRREAVMKSLIKEQKKRIASGEKLNSYI
HaKO    MMGAIDVDWRDFFPYLKWVPNKKFENTIQQMYIRREAVMKALIKQHKERIASGEKLNSYI
        : ***:************:**..*** *:. : **:****:**  :::.** ***:*****
```

MICROBIAL PRODUCTION OF ROTUNDONE

RELATED APPLICATIONS

This application claims the benefit of U.S. Provisional Application No. 62/727,815, filed Sep. 6, 2018, which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MAN-019PC Sequence Listing_ST25; date recorded: Sep. 6, 2019; file size: 235,920 bytes).

BACKGROUND

Rotundone is an oxygenated sesquiterpene (sesquiterpenoid) that is responsible for a pleasing spicy, 'peppery' aroma in various plants, including grapes (especially syrah or shiraz, mourvédre, durif, vespolina, and grüner veltliner varietals), and a large number of herbs and spices, such as, e.g., black and white pepper, oregano, basil, thyme, marjoram, and rosemary. Given its aroma, rotundone is an attractive molecule for applications in fragrances and flavors.

α-Guaiene is the precursor to (−)-rotundone. α-Guaiene is a sesquiterpene hydrocarbon found in oil extracts from various plants, and is converted to (−)-rotundone by aerial oxidation or enzymatic transformation.

Given the commercial value of rotundone, cost effective, scalable, and/or sustainable processes for its production are needed.

SUMMARY

In various aspects, the present disclosure provides methods and compositions for producing rotundone. In various aspects, the present disclosure provides enzymes, polynucleotides encoding said enzymes, and recombinant microbial host cells (or microbial host strains) for the production of rotundone. In some embodiments, the present disclosure provides microbial host cells for producing rotundone at high purity and/or yield, from either enzymatic transformation of α-guaiene, or from sugar or other carbon source. The present disclosure further provides methods of making products containing rotundone, including flavor or fragrance products, among others.

In some embodiments, the present disclosure provides a microbial host cell expressing an enzyme pathway catalyzing the conversion of farnesyl diphosphate (FPP) to rotundone, the enzymatic pathway comprising an α-guaiene terpene synthase enzyme (αGTPS) and an α-guaiene oxidase (αGOX) enzyme. In these embodiments, the microbial cells can synthesize rotundone product from any suitable carbon source. In some embodiments, the specificity of the α-guaiene synthase enzyme enables production of rotundone at high yield with fewer terpenoid byproducts. In some embodiments, the αGOX produces rotundone as the predominant oxygenated product.

In some embodiments, the microbial host cell further expresses or overexpresses one or more enzymes in the methylerythritol phosphate (MEP) and/or the mevalonic acid (MVA) pathway to catalyze the conversion of glucose or other carbon sources to isopentenyl pyrophosphate (IPP) and/or dimethylallyl pyrophosphate (DMAPP). In some embodiments, the microbial host cell further expresses an enzyme catalyzing the conversion of IPP and/or DMAPP to farnesyl diphosphate (FPP), allowing for rotundone to be produced from sugar or other carbon sources (carbon substrates such as C1, C2, C3, C4, C5, and/or C6 carbon substrates). In some embodiments, the host cell is a bacteria engineered to increase carbon flux through the MEP pathway.

In some embodiments, the microbial host cell expresses an α-guaiene oxidase (αGOX) enzyme, which may be a P450 enzyme, non-heme iron oxygenase (NHIO), or laccase providing for biotransformation of α-guaiene substrate. α-Guaiene substrate can be added to whole cell or cellular extracts or purified enzyme. In some embodiments, the cell further expresses at least one cytochrome P450 reductase to support P450 enzyme activity for whole cell bioconversion processes. In some embodiments, the αGOX produces rotundone as the predominant oxygenated product.

In some embodiments, the microbial host cell further expresses one or more alcohol dehydrogenases. In some embodiments, the alcohol dehydrogenase converts one or more alcohol intermediates, produced by the reaction of α-guaiene with αGOX, to rotundone.

In some embodiments, the microbial host cell is prokaryotic or eukaryotic, and may be a bacteria or yeast.

Other aspects and embodiments of the invention will be apparent from the following detailed disclosure.

BRIEF DESCRIPTION OF THE FIGURES

FIG. 4 shows results from the screening of amino acid substitutions in an exemplary α-guaiene terpene synthase (AcDGuaS3, SEQ ID NO: 8). Derivatives were tested for α-guaiene production in *E. coli*. The figure shows fold improvement in α-guaiene production.

FIG. 5 lists the altered profile toward production of α-guaiene in *E. coli* for several amino acid substitutions in AcDGuaS3. Fold improvement of α-guaiene as a % of the total products is listed.

FIG. 8A shows the abundance of rotundone in GC/MS and FIG. 8B shows the gas chromatogram for rotundone.

FIG. 10 shows a multiple sequence alignment of five kaurene oxygenases, including KOeng (SEQ ID NO: 51), which functions as α-guaiene oxidase enzyme. The homologs are HaKO (SEQ ID NO: 50), AaKO (SEQ ID NO: 49), CcKO (SEQ ID NO: 47), LsKO (SEQ ID NO: 46), and NtKO (SEQ ID NO: 45).

DETAILED DESCRIPTION

In various aspects, the present disclosure provides microbial host cells (or microbial host strains) and methods for producing rotundone and methods of making products containing rotundone, such as flavor and fragrance products, among others. In other aspects, the present invention provides enzymes and polynucleotides encoding enzymes for the production of rotundone.

In some embodiments, the present disclosure provides a microbial host cell, including bacteria and yeast, expressing an enzyme pathway catalyzing the conversion of farnesyl diphosphate (FPP) to rotundone. In various embodiments, the enzymatic pathway comprises a α-guaiene synthase enzyme (αGTPS) and an α-guaiene oxidase (αGOX) enzyme. In these embodiments, the microbial cells can synthesize rotundone product from any suitable carbon source. In some embodiments, the specificity of the α-guaiene synthase enzyme enables production of rotundone at high yield with fewer terpenoid byproducts. In some embodiments, the microbial host cell may further expresses one or more alcohol dehydrogenase enzymes (ADH). In some embodiments, the ADH converts one or more alcohol intermediates, produced by the reaction of α-guaiene with αGOX, to rotundone.

In some embodiments, the microbial host cell expresses an α-guaiene oxidase (αGOX) enzyme, providing for biotransformation of α-guaiene substrate. In some embodiments, αGOX is a P450 enzyme, non-heme iron oxygenase (NHIO), or laccase. In some embodiments, the cell may further express a cytochrome P450 reductase to support P450 activity. In some embodiments, the microbial host cell may further express one or more alcohol dehydrogenase enzymes (ADH). In some embodiments, the ADH converts one or more alcohol intermediates, produced by the reaction of α-guaiene with αGOX, to rotundone.

Figure 1:
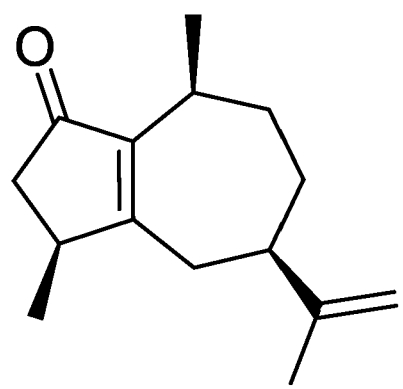
FIG. 1 shows the chemical structure of rotundone.

Rotundone comprises a guaiene carbon skeleton with a single ketone group in the carbon 2 position (see FIG. 1). α-Guaiene is the precursor to rotundone. α-Guaiene is a sesquiterpene hydrocarbon found in oil extracts from various plants. While α-guaiene can be converted to rotundone by aerial oxidation or enzymatic transformation, these processes are not efficient, in part due to the specificity of enzymes used.

Figure 2:
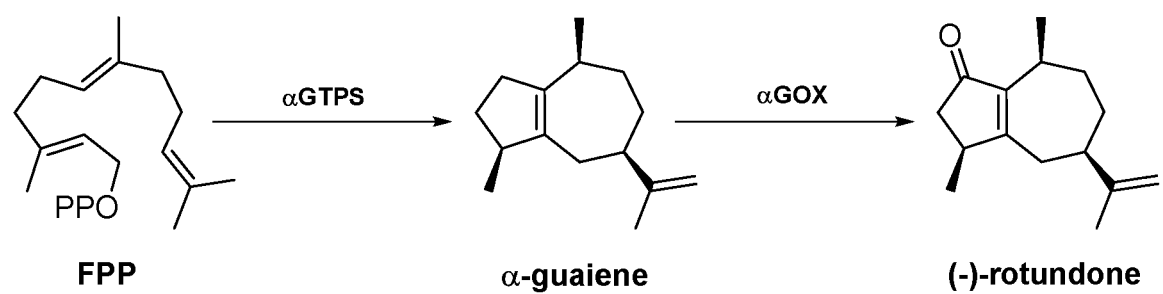
FIG. 2 illustrates a biosynthetic pathway for the production of rotundone. Farnesyl diphosphate is converted to α-guaiene by an α-guaiene terpene synthase (αGTPS) enzyme; and α-guaiene is converted to (−)-rotundone by an α-guaiene oxidase (αGOX) enzyme.

A biosynthetic pathway for rotundone is shown in FIG. 2. The C15 sesquiterpene precursor substrate farnesyl diphosphate (FPP) is cyclized to α-guaiene by an αGTPS terpene synthase enzyme. The α-guaiene (i.e., cyclized FPP) is then oxidized to rotundone via an αGOX enzyme. The production of the ketone moiety in α-guaiene resulting in rotundone can proceed directly, or can alternatively proceed through alcohol intermediates, with either stereochemistry of the alcohol intermediate, i.e., (2R)-rotundol or (2S)-rotundol (see FIG. 3).

The αGTPS enzyme is a terpene synthase enzyme (TPS). TPS enzymes are responsible for the synthesis of the terpene molecules from two isomeric 5-carbon precursor building blocks, leading to 5-carbon isoprene, 10-carbon monoterpenes, 15-carbon sesquiterpenes and 20-carbon diterpenes. The structures and functions of TPS enzymes are described in Chen et al., *The Plant Journal*, 66: 212-229 (2011). Tobacco 5-epi-aristolochene synthase, a terpene synthase, has been described along with structural coordinates, including key active site coordinates. These structural coordinates can be used for constructing homology models of αGTPS enzymes, which are useful for guiding the engineering of αGTPS enzymes with improved specificity and productivity. See, U.S. Pat. Nos. 6,645,762, 6,495,354, and 6,645,762, which are hereby incorporated by reference in their entireties.

In some embodiments, the TPS enzyme is selected from *Vitis vinifera* GuaS (VvGuas) enzyme (SEQ ID NO: 1), patchouli synthase (PcPS) enzyme from *Pogostemon cablin* (Uniprot Q49SP3) (SEQ ID NO: 2), *Vitis vinifera* germacrene D synthase (VvGDS; NCBI Ref #XP_002282488.1) (SEQ ID NO: 21), or a variant thereof. In some embodiments, the TPS enzyme is selected from *Aquilaria crassna*, for example, AcC1 (Uniprot D0VMR5); AcC2 (Uniprot D0VMR6) (SEQ ID NO: 3); AcC3 (Uniprot D0VMR7) (SEQ ID NO: 4); or AcC4 (Uniprot D0VMR8) (SEQ ID NO: 5), or a variant thereof. In some embodiments, the *A. crassna* TPS is a mutant of AcC1, for example AcC1mut1-M42 (SEQ ID NO: 6) and AcC1mut2-M50 (SEQ ID NO: 7). Other TPS enzymes are provided herein as SEQ ID NO:8 (*Aquilaria crassna* AcDGuaS3), SEQ ID NO:9 (*Aquilaria crassna* AcDGuaS4), SEQ ID NO:10 (*Aquilaria crassna* AcDGuaS2), SEQ ID NO:11 (*Aquilaria crassna* AcDGuaS5), SEQ ID NO: 12 (*Aquilaria* spp. AmiDGuaS1), SEQ ID NO: 13 (*Aquilaria* spp. AmiDGuaS2), SEQ ID NO: 14 (*Aquilaria* spp. AmiDGuaS3), SEQ ID NO: 15 (*Aquilaria* spp. AmaDGuaS1), SEQ ID NO: 16 (*Aquilaria* spp. AmaDGuaS2), SEQ ID NO: 17 (*Aquilaria* spp. AsDGuaS1), SEQ ID NO: 18 (*Aquilaria* spp. AsDGuaS2), SEQ ID NO: 19 (*Aquilaria* spp. AsDGuaS3), and SEQ ID NO: 20 (*Aquilaria* spp. AsDGuaS4), or a variant thereof.

Terpene synthase variants include α-guaiene synthase enzymes comprising an amino acid sequence that has 50% or more sequence identity with any one of SEQ ID NOs: 1 to 21. In some embodiments, the variant comprises an amino acid sequence that has at least about 60% sequence identity, or at least about 70% sequence identity, or at least about 80% sequence identity, or at least about 90% sequence identity, or at least about 95% sequence identity, or at least about 98% sequence identity, or at least about 99% sequence identity with the amino acid sequence of any one SEQ ID NOs: 1 to 21. In some embodiments, the variant includes from 1 to about 20, or from 1 to about 10, or from 1 to about 5 amino acid modifications independently selected from substitutions, deletions, and insertions to an amino acid sequence selected from SEQ ID NOs: 1 to 21. In some embodiments, the terpene synthase comprises a substitution to one or more of the substrate binding site or active site. In some embodiments, modifications to enzymes can be informed by construction of a homology model. In some embodiments, the amino acid modifications can be selected to improve one or more of: enzyme productivity, selectivity for the desired substrate and/or product, stability, temperature tolerance, and expression.

In some embodiments, the α-guaiene synthase enzyme comprises an amino acid sequence that has at least 50% sequence identity with any one of SEQ ID NOs: 1, 3, 4, 6 to 10, 11 to 15, or 19. In some embodiments, the α-guaiene synthase enzyme comprises an amino acid sequence that has at least about 60% sequence identity, or at least about 70% sequence identity, or at least about 80% sequence identity, or at least about 90% sequence identity, or at least about 95% sequence identity, or at least about 98% sequence identity, or at least about 99% sequence identity with the amino acid sequence of any one SEQ ID NOs: 1, 3, 4, 6 to 10, 11 to 15, or 19. In some embodiments, the α-guaiene synthase enzyme includes from 1 to about 20, or from 1 to about 10, or from 1 to about 5 amino acid modifications independently selected from substitutions, deletions, and insertions to an amino acid sequence selected from SEQ ID NOs: 1, 3, 4, 6 to 10, 11 to 15, or 19.

In some embodiments, the α-guaiene synthase enzyme comprises an amino acid sequence that has 50% or more sequence identity with SEQ ID NO: 8. In some embodiments, the α-guaiene synthase enzyme comprises an amino acid sequence that has at least about 60% sequence identity, or at least about 70% sequence identity, or at least about 80% sequence identity, or at least about 90% sequence identity, or at least about 95% sequence identity, or at least about 98% sequence identity, or at least about 99% sequence identity with the amino acid sequence of SEQ ID NO: 8. In some embodiments, the α-guaiene synthase enzyme includes from 1 to about 20, or from 1 to about 10, or from 1 to about 5 amino acid modifications independently selected from substitutions, deletions, and insertions to the amino acid sequence of SEQ ID NO: 8.

In some embodiments, the α-guaiene synthase may have one, two, three, four, five or more amino acid substitutions at positions corresponding to positions selected from 72, 273, 290, 368, 371, 374, 377, 381, 382, 399, 406, 419, 433, 442, 443, 454, 512, and 522 of SEQ ID NO: 8. For example, in some embodiments the α-GTPS comprises an amino acid sequence having one or more (e.g, 2, 3, 4, 5, or all) of the amino acid substitutions selected from T72I, M273L, R290K, F368M, I371L, S374A, R377V, Y381W, F382L, I399V, F406L, L419T, V433I, Y442L, I443M, E454K, F512L, and K522D relative to SEQ ID NO: 8. In some embodiments, the α-GTPS includes an amino acid substitution at the position corresponding to position 406 of SEQ ID NO: 8, and which is optionally F406L, F406A, F406I, F406V, or F406G. In some embodiments, the α-GTPS enzyme includes an amino acid substitution at the position corresponding to position 443 of SEQ ID NO: 8, which is optionally I443M. In some embodiments, the α-GTPS enzyme includes a mutation at the position corresponding to position 512 of SEQ ID NO: 8, which is optionally F512L, F512A, F512I, F512V, or F512G.

Amino acid substitutions may be conservative or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups:

(1) hydrophobic: Met, Ala, Val, Leu, Ile;
(2) neutral hydrophilic: Cys, Ser, Thr; Asn, Gln;
(3) acidic: Asp, Glu;
(4) basic: His, Lys, Arg;
(5) residues that influence chain orientation: Gly, Pro; and
(6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt a-helices. Some preferred conservative substitutions within the above six groups are exchanges within the following sub-groups: (i) Ala, Val, Leu and Ile; (ii) Ser and Thr; (iii) Asn and Gln; (iv) Lys and Arg; and (v) Tyr and Phe.

As used herein, "non-conservative substitutions" or "non-conservative amino acid exchanges" are defined as exchanges of an amino acid by another amino acid listed in a different group of the six standard amino acid groups (1) to (6) shown above.

Mutations in α-GTPS enzymes can be guided by homology models using molecular structures/models of sesquiterpene synthase disclosed in Drew et al., J. of Exp. Botany, Vol. 67, No. 3, pp. 799-808 (2015) and/or Kumeta et al., Plant Physiology, Vol. 154, pp. 1998-2007 (2010), which are hereby incorporated by reference in its entirety.

The similarity of nucleotide and amino acid sequences, i.e. the percentage of sequence identity, can be determined via sequence alignments. Such alignments can be carried out with several art-known algorithms, such as with the mathematical algorithm of Karlin and Altschul (Karlin & Altschul (1993) Proc. Natl. Acad. Sci. USA 90: 5873-5877), with hmmalign (HMMER package, http://hmmer.wustl.edu/) or with the CLUSTAL algorithm (Thompson, J. D., Higgins, D. G. & Gibson, T. J. (1994) Nucleic Acids Res. 22, 4673-80). The grade of sequence identity (sequence matching) may be calculated using e.g. BLAST, BLAT or BlastZ (or BlastX). A similar algorithm is incorporated into the BLASTN and BLASTP programs of Altschul et al (1990) J. Mol. Biol. 215: 403-410. BLAST protein searches may be performed with the BLASTP program, score=50, word length=3. To obtain gapped alignments for comparative purposes, Gapped BLAST is utilized as described in Altschul et al (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields.

TPS enzymes can generate multiple products with the guaiene skeleton from FPP with varied amounts of α-guaiene produced by different TPS enzymes. In some embodiments, the α-guaiene synthase (or engineered variant) produces predominantly α-guaiene (e.g., greater than 50%) as the product from FPP substrate. In some embodiments, the α-guaiene synthase produces greater than about 75%, or greater than about 80%, or greater than about 85%, or greater than about 90%, or greater than about 95% α-guaiene as the product from FPP. Enzyme specificity can be determined in host microbial cells producing FPP and expressing the α-guaiene synthase, followed by chemical analysis of total terpenoid products. In some embodiments, the α-guaiene produced in the αGTPS reaction is oxidized to rotundone. In some embodiments, an αGOX enzyme oxidizes α-guaiene to rotundone. In some embodiments, the αGOX oxidizes at least one portion of the α-guaiene to a ketone. In some embodiments, the oxidation of α-guaiene by αGOX results in the production of one or more alcohol intermediates. In some embodiments, the alcohol intermediates are converted to rotundone by one or more alcohol dehydrogenases.

In some embodiments, the αGOX enzyme is a cytochrome P450 (CYP450) enzyme. CYP450 enzymes are involved in the formation (synthesis) and breakdown (metabolism) of various molecules and chemicals within cells. CYP450 enzymes have been identified in all kingdoms of life (i.e., animals, plants, fungi, protists, bacteria, archaea, and even in viruses). Illustrative structure and function of CYP450 enzymes are described in Uracher et al., *TRENDS in Biotechnology*, 24(7): 324-330 (2006). In some embodiments, the P450 enzymes are engineered to have a deletion of all or part of the wild type N-terminal transmembrane region, and the addition of a transmembrane domain derived from an *E. coli* inner membrane cytoplasmic C-terminus protein. In various embodiments, the transmembrane domain is a single-pass transmembrane domain. In various embodiments, the transmembrane domain (or "N-terminal anchor") is derived from an *E. coli* gene selected from waaA, ypfN, yhcB, yhbM, yhhm, zipA, ycgG, djlA, sohB, lpxK, F11O, motA, htpx, pgaC, ygdD, hemr, and ycls. These genes were identified as inner membrane cytoplasmic C-terminus proteins through bioinformatic prediction as well as experimental validation. The invention may employ an N-terminal anchor sequence that is a derivative of the *E. coli* wild-type transmembrane domain, that is, having one or more mutations (e.g., amino acid substitutions) with respect to the wild-type sequence. Methods of making such engineered P450 enzymes as well as engineered P450 enzymes are described in U.S. Patent Publication No. 2018/0251738, which is hereby incorporated by reference in its entirety.

In some embodiments, the CYP450 is selected from the *V. vinifera* VvSTO2 (CYP71BE5; Uniprot F6I534) (SEQ ID NO: 22); *Bacillus subtilis* CYP152A1 (Uniprot O31440) (SEQ ID NO: 23); *B. subtilis* CYP107K1 (Uniprot A5HNX5) (SEQ ID NO: 24); *Bacillus cereus* CYP106 (Uniprot Q737I9) (SEQ ID NO: 25); and *B. cereus* CYP107 (Uniprot Q737F2) (SEQ ID NO: 26); or a variant thereof.

αGOX variants include enzymes comprising an amino acid sequence that has 50% or more sequence identity with any one of SEQ ID NOS: 22 to 26. In some embodiments, the variant comprises an amino acid sequence that has at least about 60% sequence identity, or at least about 70% sequence identity, or at least about 80% sequence identity, or at least about 90% sequence identity, or at least about 95% sequence identity, or at least about 98% sequence identity, or at least about 99% sequence identity with the amino acid sequence of any one SEQ ID NOS: 22 to 26. In some embodiments, the variant includes from 1 to about 20, or from 1 to about 10, or from 1 to about 5 amino acid modifications independently selected from substitutions, deletions, and insertions to an amino acid sequence selected from SEQ ID NO: 22 to 26. In some embodiments, the oxygenase comprises a substitution to one or more of the substrate binding site or active site. In some embodiments, modifications to enzymes can be informed by construction of a homology model. In some embodiments, selection and modification of enzymes is informed by assaying activity on α-guaiene substrate. In some embodiments, the amino acid modifications can be selected to improve one or more of: enzyme productivity, selectivity for the desired substrate and/or product, stability, temperature tolerance, and expression.

In some embodiments, the αGOX enzyme is a non-heme iron oxygenase (NHIO) or a laccase. In some embodiments, the laccase is derived from bacteria or fungi (including filamentous fungi and yeasts). By way of example, in some embodiments, the laccase is from a species selected from *Aspergillus*, *Neurospora* (e.g., *N. crassa*), *Podospora*, *Botrytis*, *Collybia*, *Fomes*, *Lentinus*, *Lentinus*, *Pleurotus*, *Trametes*, *Rhizoctonia* (e.g., *R. solani*), *Coprinus* (e.g., *C. plicatilis*), *Psatyrella*, *Mycehophtera* (e.g., *M. thermophila*), *Schytalidium*, and *Polyporus*, (e.g., *P. pinsitus*), *Phiebia*, and *Coriolus*, or is a derivative thereof.

In some embodiments, the CYP450 (αGOX) comprises an amino acid sequence that has at least 50% identity to SEQ ID NO: 51. In some embodiments, the CYP450 enzyme comprises an amino acid sequence that is at least about 55%, or at least about 60%, or at least about 65%, or at least about 70%, or at least about 75%, or at least about 80%, or at least about 85%, or at least about 90%, or at least about 95%, or at least 98%, or at least 99% identical to SEQ ID NO: 51. For example, the CYP450 enzyme may comprise an amino acid sequence having from 1 to 20 or from 1 to 10 amino acid modifications with respect to SEQ ID NO: 51, the amino acid modifications being independently selected from amino acid substitutions, deletions, and insertions with respect to corresponding positions in SEQ ID NO: 51.

In some embodiments, the CYP450 comprises an amino acid sequence that has at least 50% identity to SEQ ID NO: 52. In some embodiments, the CYP450 enzyme comprises an amino acid sequence that is at least about 55%, or at least about 60%, or at least about 65%, or at least about 70%, or at least about 75%, or at least about 80%, or at least about 85%, or at least about 90%, or at least about 95%, or at least 98%, or at least 99% identical to SEQ ID NO: 52. For example, the CYP450 enzyme may comprise an amino acid sequence having from 1 to 20 or from 1 to 10 amino acid modifications with respect to SEQ ID NO: 52, the amino acid modifications being independently selected from amino acid substitutions, deletions, and insertions with respect to corresponding positions in SEQ ID NO: 52.

In some embodiments, the CYP450 comprises an amino acid sequence that has at least 50% identity to SEQ ID NOs: 54, 55, or 56. In some embodiments, the CYP450 enzyme comprises an amino acid sequence that is at least about 55%, or at least about 60%, or at least about 65%, or at least about 70%, or at least about 75%, or at least about 80%, or at least about 85%, or at least about 90%, or at least about 95%, or at least 98%, or at least 99% identical to SEQ ID NOs: 54, 55, or 56. For example, the CYP450 enzyme may comprise an amino acid sequence having from 1 to 20 or from 1 to 10 amino acid modifications with respect to SEQ ID NO: 54, 55, or 56, the amino acid modifications being independently selected from amino acid substitutions, deletions, and insertions with respect to corresponding positions in SEQ ID NO: 54, 55, or 56.

Amino acid modification to CYP450 enzymes can be guided by available structures, including those described in Pallan et al., "Structural and kinetic basis of steroid 17a, 20-lyase activity in teleost fish cytochrome P450 17A1 and its absence in cytochrome P450 17A2," *Journal of Biological Chemistry* 290.6 (2015): 3248-3268, which is hereby incorporated by reference in its entirety. Pallan et al. describe a Zebra fish cytochrome P450 17A2 along with structural coordinates, including key active site coordinates. These structural coordinates can be used for constructing homology models of CYP450 enzymes, which are useful for guiding the engineering of CYP450 enzymes with improved specificity and productivity.

In some embodiments, the CYP450 enzyme requires the presence of an electron transfer protein capable of transferring electrons to the CYP450 protein. In some embodiments, this electron transfer protein is a cytochrome P450 reductase (CPR), which can be expressed by the microbial host cell. Various reductases that may be used are described in U.S.

Patent Publication No. 2018/0135081, which is hereby incorporated by reference in its entirety.

Exemplary P450 reductase enzymes include those shown herein as SEQ ID NOs: 27 to 34 or 53, or a variant thereof. Variants generally include enzymes comprising an amino acid sequence that has 50% or more sequence identity with any one of SEQ ID NOs: 27 to 34 or 53. In some embodiments, the variant comprises an amino acid sequence that has at least about 60% sequence identity, or at least about 70% sequence identity, or at least about 80% sequence identity, or at least about 90% sequence identity, or at least about 95% sequence identity, or at least about 98% sequence identity, or at least about 99% sequence identity with the amino acid sequence of any one SEQ ID NOs: 27 to 34 or 53. In some embodiments, the variant includes from 1 to about 20, or from 1 to about 10, or from 1 to about 5 amino acid modifications independently selected from substitutions, deletions, and insertions to an amino acid sequence selected from SEQ ID NOs: 27 to 34 or 53.

In some embodiments, the CPR comprises an amino acid sequence that has at least 50% identity to SEQ ID NO: 53 (CaCPR). In some embodiments, the CPR enzyme comprises an amino acid sequence that is at least about 55%, or at least about 60%, or at least about 65%, or at least about 70%, or at least about 75%, or at least about 80%, or at least about 85%, or at least about 90%, or at least about 95%, or at least 98%, or at least 99% identical to SEQ ID NO: 53. For example, the CPR enzyme may comprise an amino acid sequence having from 1 to 20 or from 1 to 10 amino acid modifications with respect to SEQ ID NO: 53, the amino acid modifications being independently selected from amino acid substitutions, deletions, and insertions with respect to corresponding positions in SEQ ID NO: 53.

Figure 3:
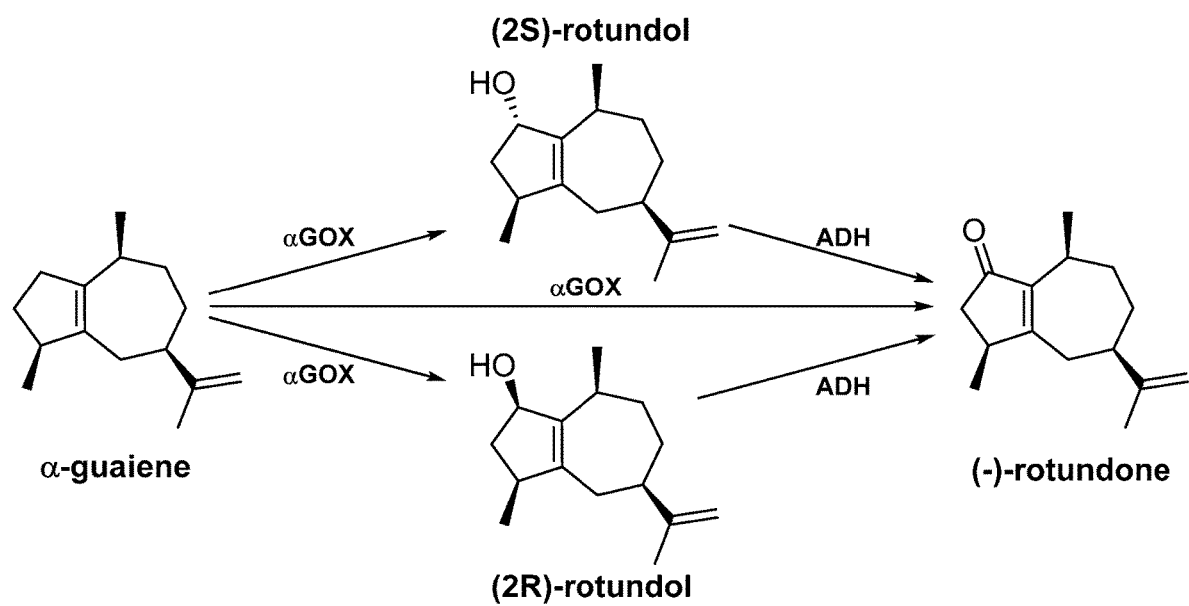
FIG. 3 illustrates that the production of (−)-rotundone from α-guaiene can proceed directly from the sesquiterpene precursor, or can involve the production of one or both alcohol intermediates which are subsequently converted to the ketone by an enzyme with alcohol dehydrogenase activity.

In some embodiments, the αGOX reaction results in hydroxylation of α-guaiene, thereby producing one or more alcohol intermediates, e.g., (2R)-rotundol or (2S)-rotundol (see FIG. 3). In some embodiments, the αGOX further oxidizes at least a portion of the α-guaiene to a ketone. In some embodiments, the alcohol intermediates (e.g., (2R)-rotundol or (2S)-rotundol) are converted to rotundone by one or more alcohol dehydrogenases (ADHs). Thus, in some embodiments, the microbial host cell expresses one or more alcohol dehydrogenases (ADH). By way of example, in some embodiments, the ADH is selected from an enzyme comprising an amino acid sequence selected from SEQ ID NOs: 35 to 44, or a variant thereof. Variants generally include enzymes comprising an amino acid sequence that has 50% or more sequence identity with any one of SEQ ID NOs: 35 to 44. In some embodiments, the variant comprises an amino acid sequence that has at least about 60% sequence identity, or at least about 70% sequence identity, or at least about 80% sequence identity, or at least about 90% sequence identity, or at least about 95% sequence identity, or at least about 98% sequence identity, or at least about 99% sequence identity with the amino acid sequence of any one SEQ ID NOS: 35 to 44. In some embodiments, the variant includes from 1 to about 20, or from 1 to about 10, or from 1 to about 5 amino acid modifications independently selected from substitutions, deletions, and insertions to an amino acid sequence selected from SEQ ID NO: 35 to 44. In some embodiments, the amino acid modifications can be selected to improve one or more of: enzyme productivity, selectivity for the desired substrate and/or product, stability, temperature tolerance, and expression.

In some embodiments, the ADH comprises an amino acid sequence that has at least 50% identity to SEQ ID NO: 43 (VvDH). In some embodiments, the ADH enzyme comprises an amino acid sequence that is at least about 55%, or at least about 60%, or at least about 65%, or at least about 70%, or at least about 75%, or at least about 80%, or at least about 85%, or at least about 90%, or at least about 95%, or at least 98%, or at least 99% identical to SEQ ID NO: 43. For example, the ADH enzyme may comprise an amino acid sequence having from 1 to 20 or from 1 to 10 amino acid modifications with respect to SEQ ID NO: 43, the amino acid modifications being independently selected from amino acid substitutions, deletions, and insertions with respect to corresponding positions in SEQ ID NO: 43.

In some embodiments, the microbial cell expresses an αGOX, and produces predominately rotundone (e.g., at least 75% of the oxygenated product is rotundone), without expression of an ADH enzyme.

In various embodiments, the αGTPS and αGOX are expressed together in an operon, or are expressed individually. The enzymes may be expressed from extrachromosomal elements such as plasmids, or bacterial artificial chromosomes, or may be chromosomally integrated.

In some embodiments, the cell does not express an αGTPS, but expresses an α-guaiene oxidase (αGOX), allowing enzymatic biotransformation of α-guaiene, which can take place with whole cells or whole or partially purified extracts of cells.

In some embodiments, the αGOX and/or the ADH are provided in a purified recombinant form for production of rotundone from α-guaiene, or (2R)-rotundol or (2S)-rotundol, in a cell free system.

In some embodiments, the microbial host cell is also engineered to express or overexpress one or more enzymes in the methylerythritol phosphate (MEP) and/or the mevalonic acid (MVA) pathway to catalyze isopentenyl pyrophosphate (IPP) and dimethylallyl pyrophosphate (DMAPP) from glucose or other carbon source.

In some embodiments, the microbial host cell is engineered to express or overexpress one or more enzymes of the MEP pathway. In some embodiments, the MEP pathway is increased and balanced with downstream pathways by providing duplicate copies of certain rate-limiting enzymes. The MEP (2-C-methyl-D-erythritol 4-phosphate) pathway, also called the MEP/DOXP (2-C-methyl-D-erythritol 4-phosphate/1-deoxy-D-xylulose 5-phosphate) pathway or the non-mevalonate pathway or the mevalonic acid-independent pathway refers to the pathway that converts glyceraldehyde-3-phosphate and pyruvate to IPP and DMAPP. The pathway typically involves action of the following enzymes: 1-deoxy-D-xylulose-5-phosphate synthase (Dxs), 1-deoxy-D-xylulose-5-phosphate reductoisomerase (IspC), 4-diphosphocytidyl-2-C-methyl-D-erythritol synthase (IspD), 4-diphosphocytidyl-2-C-methyl-D-erythritol kinase (IspE), 2C-methyl-D-erythritol 2,4-cyclodiphosphate synthase (IspF), 1-hydroxy-2-methyl-2-(E)-butenyl 4-diphosphate synthase (IspG), and isopentenyl diphosphate isomerase (IspH). The MEP pathway, and the genes and enzymes that make up the MEP pathway, are described in U.S. Pat. No. 8,512,988, which is hereby incorporated by reference in its entirety. For example, genes that make up the MEP pathway include dxs, ispC, ispD, ispE, ispF, ispG, ispH, idi, and ispA. In some embodiments, the microbial host cell expresses or overexpresses of one or more of dxs, ispC, ispD, ispE, ispF, ispG, ispH, idi, ispA, or modified variants thereof, which results in the increased production of IPP and DMAPP. In some embodiments, rotundone is produced at least in part by metabolic flux through an MEP pathway, and wherein the microbial host cell has at least one additional gene copy of one or more of dxs, ispC, ispD, ispE, ispF, ispG, ispH, idi, ispA, or modified variants thereof.

In some embodiments, the microbial host cell is engineered to express or overexpress one or more enzymes of the MVA pathway. The MVA pathway refers to the biosynthetic pathway that converts acetyl-CoA to IPP. The mevalonate pathway typically comprises enzymes that catalyze the following steps: (a) condensing two molecules of acetyl-CoA to acetoacetyl-CoA (e.g., by action of acetoacetyl-CoA thiolase); (b) condensing acetoacetyl-CoA with acetyl-CoA to form hydroxymethylglutaryl-CoenzymeA (HMG-CoA) (e.g., by action of HMG-CoA synthase (HMGS)); (c) converting HMG-CoA to mevalonate (e.g., by action of HMG-CoA reductase (HMGR)); (d) phosphorylating mevalonate to mevalonate 5-phosphate (e.g., by action of mevalonate kinase (MK)); (e) converting mevalonate 5-phosphate to mevalonate 5-pyrophosphate (e.g., by action of phosphomevalonate kinase (PMK)); and (f) converting mevalonate 5-pyrophosphate to isopentenyl pyrophosphate (e.g., by action of mevalonate pyrophosphate decarboxylase (MPD)). The MVA pathway, and the genes and enzymes that make up the MVA pathway, are described in U.S. Pat. No. 7,667,017, which is hereby incorporated by reference in its entirety. In some embodiments, the microbial host cell expresses or overexpresses one or more of acetoacetyl-CoA thiolase, HMGS, HMGR, MK, PMK, and MPD or modified variants thereof, which results in the increased production of IPP and DMAPP. In some embodiments, rotundone is produced at least in part by metabolic flux through an MVA pathway, and wherein the microbial host cell has at least one additional gene copy of one or more of acetoacetyl-CoA thiolase, HMGS, HMGR, MK, PMK, MPD, or modified variants thereof.

In some embodiments, the microbial host cell is engineered to increase production of IPP and DMAPP from glucose as described in PCT Application Nos. PCT/US2018/016848 and PCT/US2018/015527, the contents of which are hereby incorporated by reference in their entireties. For example, in some embodiments the microbial host cell overexpresses MEP pathway enzymes, with balanced expression to push/pull carbon flux to IPP and DMAPP. In some embodiments, the microbial host cell is engineered to increase the availability or activity of Fe—S cluster proteins, so as to support higher activity of IspG and IspH, which are Fe—S enzymes. In some embodiments, the host cell is engineered to overexpress IspG and IspH, so as to provide increased carbon flux to 1-hydroxy-2-methyl-2-(E)-butenyl 4-diphosphate (HMBPP) intermediate, but with balanced expression to prevent accumulation of HMBPP at an amount that reduces cell growth or viability, or at an amount that inhibits MEP pathway flux.

Conversion of IPP and DMAPP precursors to farnesyl diphosphate (FPP) is typically through the action of a farnesyl diphosphate synthase (FPPS). Exemplary FPPS enzymes are disclosed in US 2018/0135081, which is hereby incorporated by reference in its entirety.

In some embodiments, the host cell is engineered to downregulate the ubiquinone biosynthesis pathway, e.g., by reducing the expression or activity of IspB, which uses IPP and FPP substrate.

In some embodiments, the microbial host cell is a bacteria selected from *Escherichia* spp., *Bacillus* spp., *Corynebacterium* spp., *Rhodobacter* spp *Zymomonas* spp., *Vibrio* spp., and *Pseudomonas* spp. For example, in some embodiments, the bacterial host cell is a species selected from *Escherichia coli, Bacillus subtilis, Corynebacterium glutamicum, Rhodobacter capsulatus, Rhodobacter sphaeroides, Zymomonas mobilis, Vibrio natriegens*, or *Pseudomonas putida*. In some embodiments, the bacterial host cell is *E. coli*.

In some embodiments, the microbial host cell is a species of *Saccharomyces, Pichia*, or *Yarrowia*, including, but not limited to, *Saccharomyces cerevisiae, Pichia pastoris*, and *Yarrowia lipolytica*.

In another aspect, the present disclosure provides a method for making rotundone. The method comprises providing a microbial host cell (or microbial host strain) as disclosed herein. The microbial host cell expresses an αGOX enzyme, and optionally an αGTPS enzyme as described herein. Cells expressing an αGOX enzyme can be used for bioconversion of α-guaiene using whole cells or cell extracts. Cells expressing an αGOX enzyme and an αGTPS enzyme can produce rotundone from a carbon source.

In some embodiments, the microbial host cell further expresses one or more alcohol dehydrogenases (ADHs) disclosed herein. Cells expressing ADHs can convert alcohol intermediates produced by the αGOX reaction into rotundone.

In some embodiments, the host cell is cultured to produce rotundone. In some embodiments, microbial cells are cultured with carbon substrates (sources) such as C1, C2, C3, C4, C5, and/or C6 carbon substrates. In exemplary embodiments, the carbon source is glucose, sucrose, fructose, xylose, and/or glycerol. Culture conditions are generally selected from aerobic, microaerobic, and anerobic.

In various embodiments, the host cell is cultured at a temperature between 22° C. and 37° C. While commercial biosynthesis in bacteria such as *E. coli* can be limited by the temperature at which overexpressed and/or foreign enzymes (e.g., enzymes derived from plants) are stable, recombinant enzymes (including the terpenoid synthase) may be engineered to allow for cultures to be maintained at higher temperatures, resulting in higher yields and higher overall productivity. In some embodiments, the host cell is a bacterial host cell, and culturing is conducted at about 22° C. or greater, about 23° C. or greater, about 24° C. or greater, about 25° C. or greater, about 26° C. or greater, about 27° C. or greater, about 28° C. or greater, about 29° C. or greater, about 30° C. or greater, about 31° C. or greater, about 32° C. or greater, about 33° C. or greater, about 34° C. or greater, about 35° C. or greater, about 36° C. or greater, or about 37° C.

Rotundone can be extracted from media and/or whole cells, and recovered. In some embodiments, the oxygenated rotundone product is recovered and optionally enriched by fractionation (e.g. fractional distillation). The oxygenated product can be recovered by any suitable process, including partitioning the desired product into an organic phase. The production of the desired product can be determined and/or quantified, for example, by gas chromatography (e.g., GC-MS). The desired product can be produced in batch or continuous bioreactor systems. Production of product, recovery, and/or analysis of the product can be done as described in US 2012/0246767, which is hereby incorporated by reference in its entirety. For example, in some embodiments, oxidized oil is extracted from aqueous reaction medium, which may be done by partitioning into an organic phase, followed by fractional distillation. Sesquiterpene and sesquiterpenoid components of fractions may be measured quantitatively by GC/MS, followed by blending of the fractions.

In some embodiments, the microbial host cells and methods disclosed herein are suitable for commercial production of rotundone, that is, the microbial host cells and methods are productive at commercial scale. In some embodiments, the size of the culture is at least about 100 L, at least about 200 L, at least about 500 L, at least about 1,000 L, at least about 10,000 L, at least about 100,000 L, or at least about 1,000,000 L. In some embodiment, the culturing may be conducted in batch culture, continuous culture, or semi-continuous culture.

In some aspects, the present disclosure provides methods for making a product comprising rotundone, including flavor and fragrance compositions or products. In some embodiments, the method comprises producing rotundone as described herein through microbial culture, recovering the rotundone, and incorporating the rotundone into the flavor or fragrance composition, or a consumable product (e.g., a food product).

As used in this specification and the appended claims, the singular forms "a", "an" and "the" include plural referents unless the content clearly dictates otherwise. For example, reference to "a cell" includes a combination of two or more cells, and the like.

As used herein, the term "about" in reference to a number is generally taken to include numbers that fall within a range of 10% in either direction (greater than or less than) of the number.

EXAMPLES

Rotundone is a bicyclic sesquiterpene (FIG. 1) and is responsible for pepper aromas in grapes and wine and in herbs and spices, especially black and white pepper, where it has a high odor activity value (OAV). The biosynthesis of rotundone involves cyclization of the C15 sesquiterpene precursor substrate farnesyl diphosphate (FPP) to α-guaiene by an α-GTPS terpene synthase (FIG. 2). Enzymatic oxygenation of α-guaiene can produce rotundone, and may proceed through an alcohol intermediate (FIGS. 2 and 3). For example, α-guaiene may be converted to (2S)-rotundol or (2R)-rotundol by the action of αGOX, and the alcohol intermediate(s) (rotundol) can be converted to rotundone by the action of the αGOX or an alcohol dehydrogenase.

Example 1: Engineering α-Guaiene Synthase to Improve α-Guaiene Production

The α-guaiene precursor, rotundol, or rotundone can be produced by biosynthetic fermentation processes, using microbial strains that produce high levels of MEP pathway products, along with heterologous expression of rotundone biosynthesis enzymes, including, enzymes that catalyze 1) cyclization of FPP to α-guaiene; 2) oxidation of α-guaiene to rotundone, which can include 3) dehydrogenation of rotundol to rotundone. For example, in bacteria such as E. coli, isopentenyl pyrophosphate (IPP) and dimethylallyl pyrophosphate (DMAPP) can be produced from glucose or other carbon source, and which can be converted to farnesyl diphosphate (FPP) by recombinant farnesyl diphosphate synthase (FPPS). FPP is converted to α-guaiene by α-guaiene synthase (αGTPS) by cyclization. The α-guaiene is converted to rotundol or rotundone by oxygenation reaction catalyzed by an α-guaiene oxidase (αGOX). In instances where the αGOX enzyme catalyzes the production of (2S)-rotundol or (2R)-rotundol from α-guaiene, the conversion of rotundol to rotundone may be catalyzed by a dehydrogenase.

Using an E. coli background strain that produces high levels of the MEP pathway products IPP and DMAPP (see US 2018/0245103 and US 2018/0216137, which are hereby incorporated by reference), candidate αGTPS enzymes were screened by co-expression with FPPS. Fermentation was performed in 96 well plates for 48 hours. The following synthase enzymes demonstrated production of α-guaiene in E. coli: AcC1mut1_M42, AcC1mut2_M50, AcC2, AcC3, AcDGuaS2, AcDGuaS3, AcDGuaS4, AcDGuaS5, AmaDGuaS1, AmiDGuaS1, AmiDGuaS2, AmiDGuaS3, AsDGuaS3, PcPS, and VvGuaS. In addition to the desired α-guaiene product, active enzymes had varying product profiles. For example, all active Aquilaria enzymes showed α-bulnesene as a major product with α-guaiene. VvGuaS accumulated α-bulnesene and globulol in similar levels to α-guaiene. AcDGuaS3 was selected for subsequent studies based on its productivity and product profile.

Figure 6:
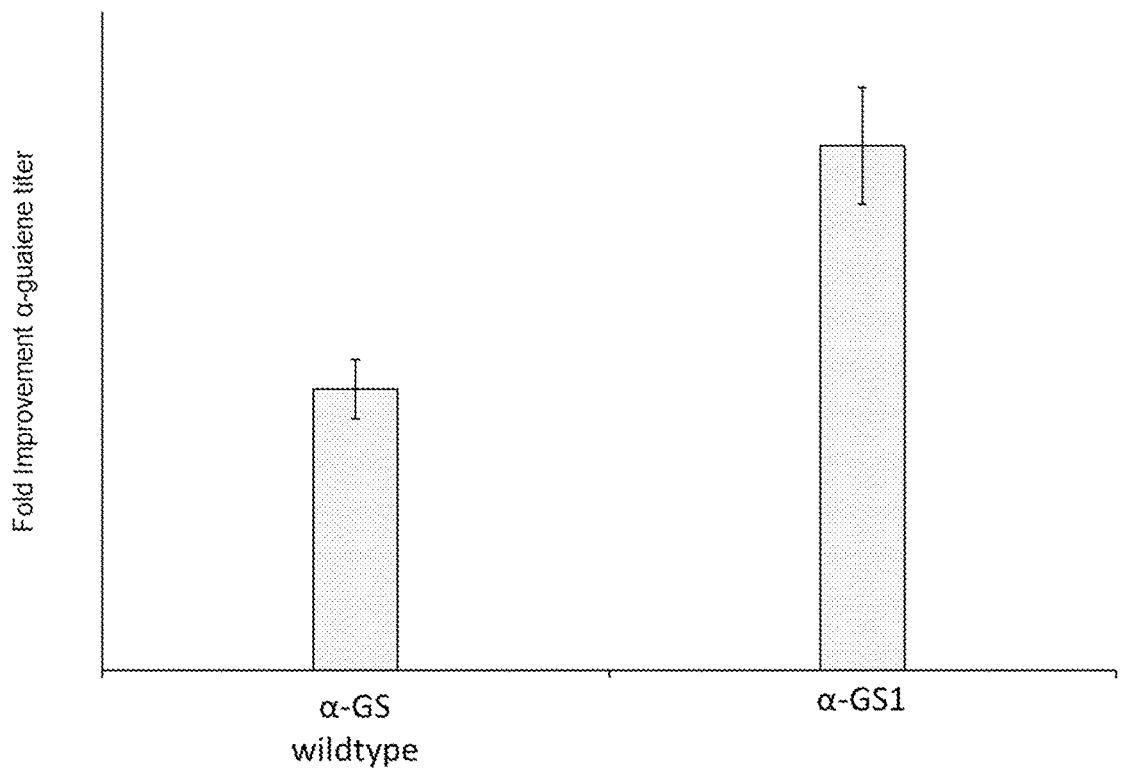
FIG. 6 shows production of α-guaiene with expression of wild-type AcDGuaS3 (α-GS) and mutant AcDGuaS3 having an F406L mutation (α-GS1) in *E. coli*.

A panel of amino acid substitutions to the AcDGuaS3 sequence were screened for their ability to convert FPP to α-guaiene in E. coli. The fermentation was conducted in 96 well plates for 48 hours. FIG. 4 shows several mutants (i.e., amino acid substitutions) and the associated fold-improvement in α-guaiene production. For example, F406L substitution in AcDGuaS3 demonstrated a significantly improved titer of α-guaiene (1.71 fold higher than wild-type). Amino acid substitutions were further evaluated for substitutions that shift the product profile toward α-guaiene. See FIG. 5. As shown, a single substitution in wild-type AcDGuaS3 (I443M) shows a 2.4 fold improvement in % α-guaiene relative to other products. Similarly, a F406L substitution shows a 2.12 fold improvement in % α-guaiene relative to other products. A F512 mutation demonstrated a 1.23 fold improvement in % α-guaiene relative to other products. FIG. 6 shows the fold improvement in titer of α-guaiene, based on expression of a variant having an F406L substitution in AcDGuaS3 (α-GS1) as compared to the parent enzyme.

Example 2: Production of Rotundone

Figure 7A:
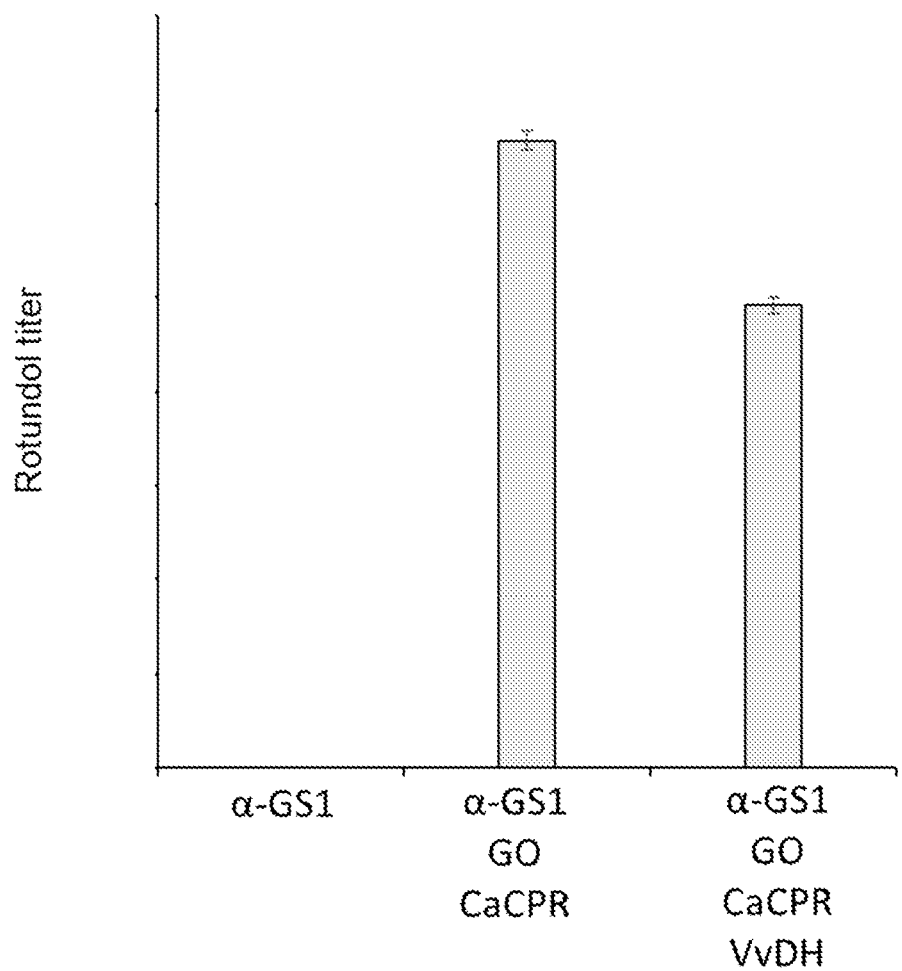
FIGS. 7A and 7B show production of rotundol and rotundone in *E. coli* expressing α-GS1 and an exemplary CYP450 system (engineered kaurene oxidase; KOeng). Expression of *Vitis vinifera* dehydrogenase (VvDH) along with α-GS1, KOeng as the α-guaiene oxidase, and *Camptotheca acuminata* cytochrome P450 reductase (CaCPR) reduces the titer of rotundol (FIG. 7A) and increases rotundone titer (FIG. 7B).
Figure 7B:
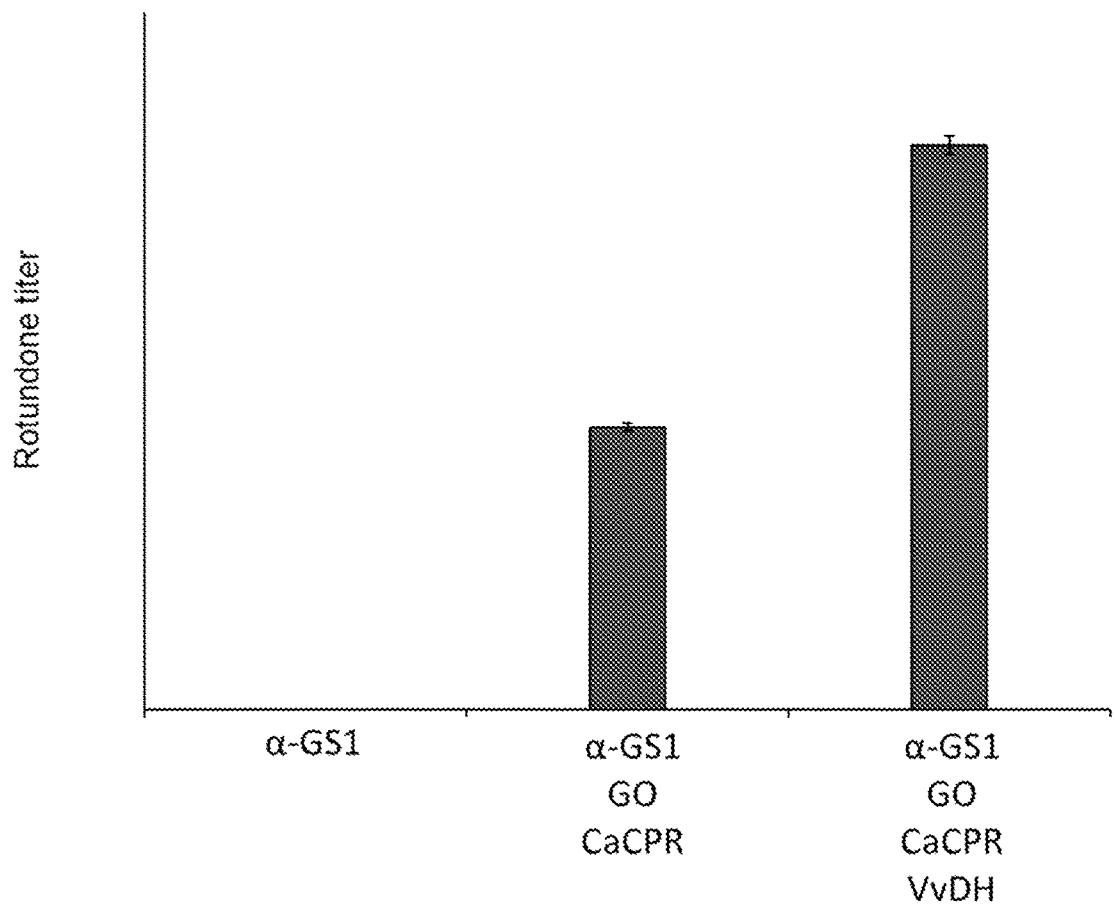
Figure 8A:
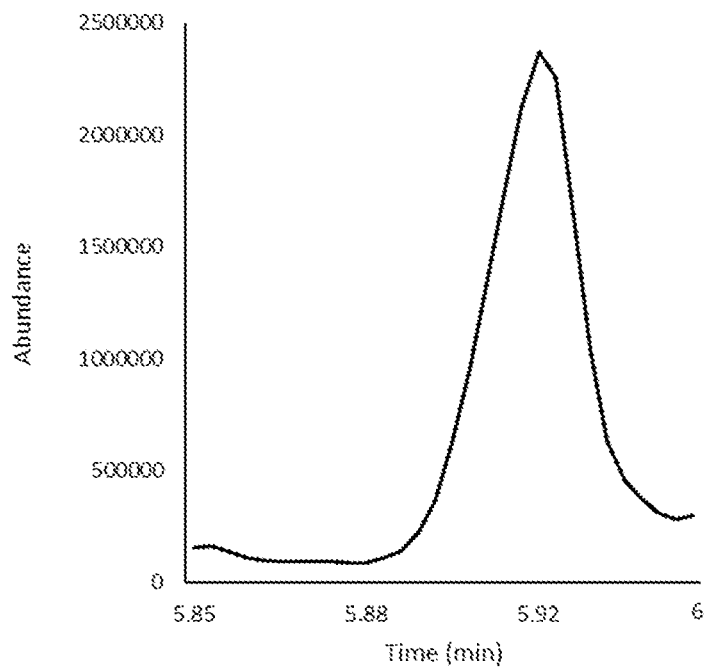
FIGS. 8A and B show Gas-Chromatography/Mass Spectrometry (GC/MS) confirmation of production of rotundone from *E. coli* strain expressing α-GS1, KOeng, CaCPR, and VvDH.
Figure 8B:
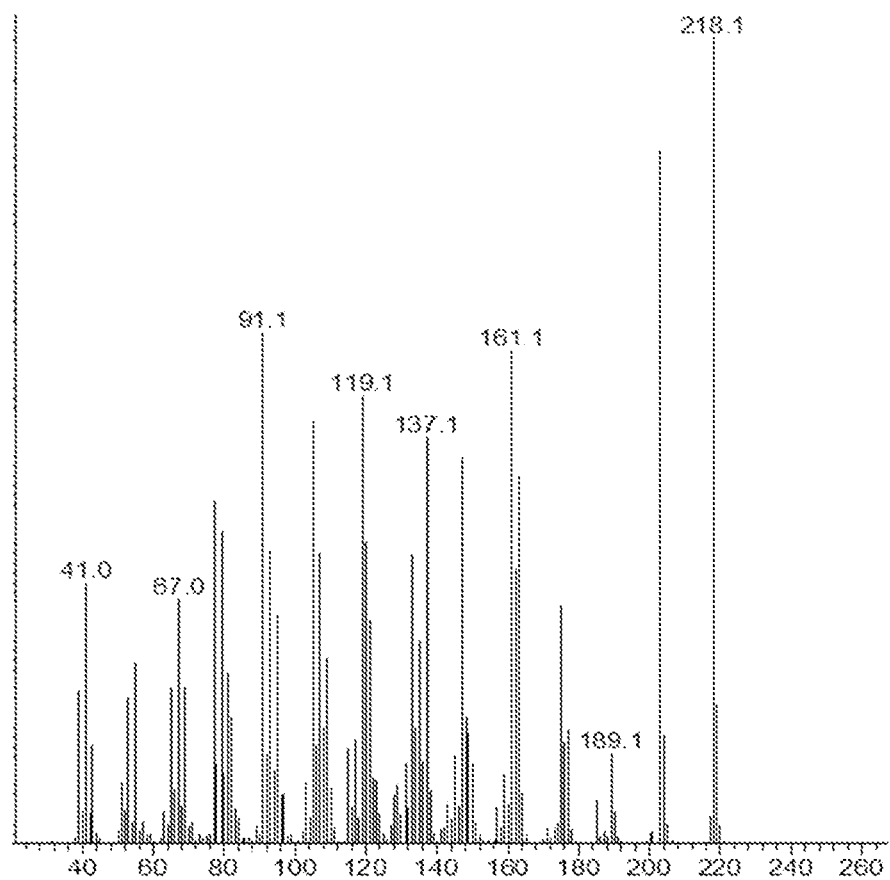

Candidate α-guaiene oxidase enzymes where screened by co-expression in E. coli with FPPS and α-GS1. Production of rotundol and rotundone were observed with expression of an engineered Kaurene Oxidase (KOeng). See, US 2018/0135081, which is hereby incorporated by reference in its entirety. Co-expression of Vitis vinifera dehydrogenase (VvDH) along with α-GS1, KOeng, and Camptotheca acuminata cytochrome P450 reductase (CaCPR) reduces the titer of rotundol (FIG. 7A) and increases rotundone titer (FIG. 7B). Rotundone derived from oxidation of α-guaiene by cytochrome P450 was confirmed by GC/MS (FIGS. 8A and 8B). The KOeng can be further engineered to improve specificity for the α-guaiene substrate. An alignment with wild-type kaurene oxidase enzymes is shown in Example 10, which can assist this engineering.

Figure 9:
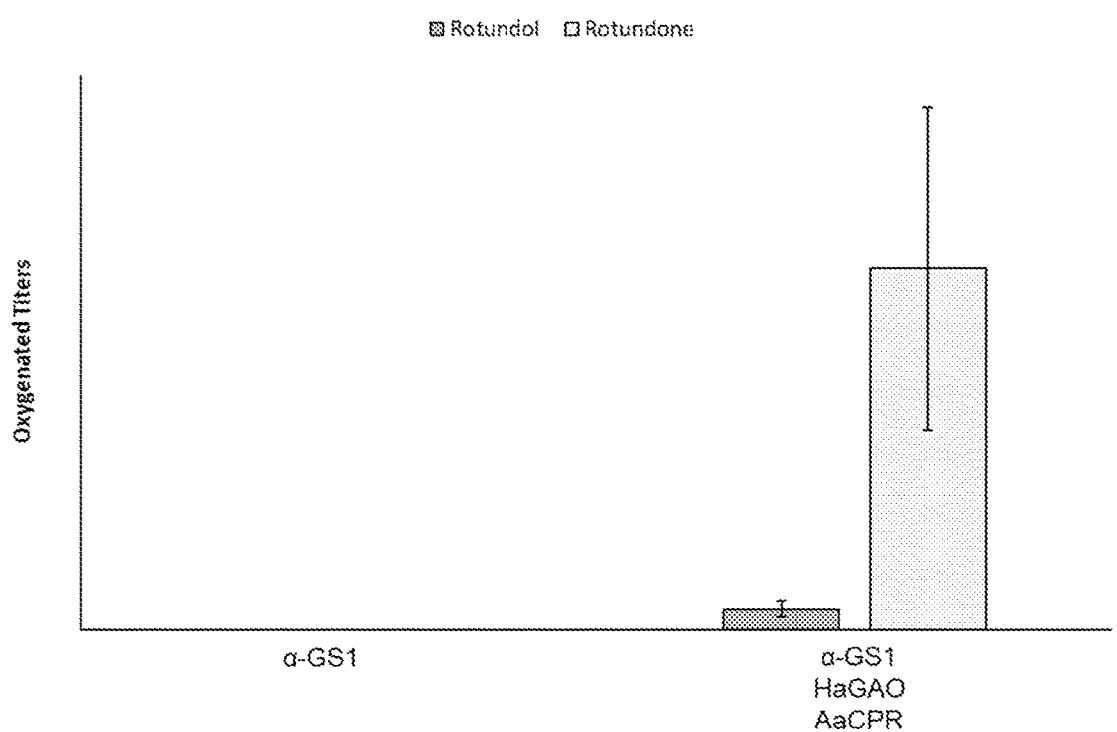
FIG. 9 shows production of rotundol and rotundone in *E. coli* expressing α-GS1 and an alternative CYP450 system. Expression of α-GS1, *Helianthus annuus* germacrene A monooxygenase engineered for expression in *E. coli* (HaGAO), and AaCPR (*Artemisia annua* cytochrome P450 reductase) produces primarily rotundone.

FIG. 9 shows in vivo production of rotundol and rotundone using an alternative CYP450 system, based on expression of Helianthus annuus germacrene A monooxygenase (HaGAO). The E. coli strain included expression of α-GS1, engineered HaGAO for expression in E. coli (SEQ ID NO:52), and AaCPR (Artemisia annua cytochrome P450 reductase; SEQ ID NO: 33). The fermentation was conducted in 96 well plates for 48 hours. As shown in FIG. 9, the oxygenated product was substantially rotundone, with only minor amounts of the rotundol intermediate.

SEQUENCES
Terpene Synthase
*Vitis vinifera* VvGuaS

SEQ ID NO: 1

MSVPLSVSVTPILSQRIDPEVARHEATYHPNFWGDRFLHYNPDDDFCGTHACKEQQIQEL

KEEVRKSLEATAGNTSQLLKLIDSIQRLGLAYHFEREIEEALKAMYQTYTLVDDNDHLTT

VSLLFRLLRQEGYHIPSDVFKKFMDEGGNFKESLVGDLPGMLALYEAAHLMVHGEDILDE

ALGFTTAHLQSMAIDSDNPLTKQVIRALKRPIRKGLPRVEARHYITIYQEDDSHNESLLK

LAKLDYNMLQSLHRKELSEITKWWKGLDFATKLPFARDRIVEGYFWILGVYFEPQYYLAR

RILMKVFGVLSIVDDIYDAYGTFEELKLFTEAIERWDASSIDQLPDYMKVCYQALLDVYE

EMEEEMTKQGKLYRVHYAQAALKRQVQAYLLEAKWLKQEYIPTMEEYMSNALVTSACSML

TTTSFVGMGDMVTKEAFDWVFSDPKMIRASNVICRLMDDIVSHEFEQKRGHVASAVECYM

KQYGVSKEEAYDEFKKQVESAWKDNNEEVLQPTAVPVPLLTRVLNFSRMVDVLYKDEDEY

TLVGPLMKDLVAGMLIDPVPM

*Pogostemon cablin* PcPS (Q49SP3)

SEQ ID NO: 2

MELYAQSVGVGAASRPLANFHPCVWGDKFIVYNPQSCQAGEREEAEELKVELKRELKEAS

DNYMRQLKMVDAIQRLGIDYLFVEDVDEALKNLFEMFDAFCKNNHDMHATALSFRLLRQH

GYRVSCEVFEKFKDGKDGFKVPNEDGAVAVLEFFEATHLRVHGEDVLDNAFDFTRNYLES

VYATLNDPTAKQVHNALNEFSFRRGLPRVEARKYISIYEQYASHHKGLLKLAKLDFNLVQ

ALHRRELSEDSRWWKTLQVPTKLSFVRDRLVESYFWASGSYFEPNYSVARMILAKGLAVL

SLMDDVYDAYGTFEELQMFTDAIERWDASCLDKLPDYMKIVYKALLDVFEEVDEELIKLG

APYRAYYGKEAMKYAARAYMEEAQWREQKHKPTTKEYMKLATKTCGYITLIILSCLGVEE

GIVTKEAFDWVFSRPPFIEATLIIARLVNDITGHEFEKKREHVRTAVECYMEEHKVGKQE

VVSEFYNQMESAWKDINEGFLRPVEFPIPLLYLILNSVRTLEVIYKEGDSYTHVGPAMQN

IIKQLYLHPVPY

*Aquilaria crassna* AcC2 (D0VMR6)

SEQ ID NO: 3

MSSAKLGSASEDVNRRDANYHPTVWGDFFLTHSSNFLENNDSILEKHEELKQEVRNLLVV

ETSDLPSKIQLTDEIIRLGVGYHFETEIKAQLEKLHDHQLHLNFDLLTTSVWFRLLRGHG

FSISSDVFKRFKNTKGEFETEDARTLWCLYEATHLRVDGEDILEEAIQFSRKKLEALLPE

LSFPLNECVRDALHIPYHRNVQRLAARQYIPQYDAEPTKIESLSLFAKIDFNMLQALHQR

ELREASRWWKEFDFPSKLPYARDRIAEGYYWMMGAHFEPKFSLSRKFLNRIIGITSLIDD

TYDVYGTLEEVTLFTEAVERWDIEAVKDIPKYMQVIYTGMLGIFEDFKDNLINARGKDYC

IDYAIEVFKEIVRSYQREAEYFHTGYVPSYDEYMENSIISGGYKMFIILMLIGRGEFELK

ETLDWASTIPEMVEASSLIARYIDDLQTYKAEEERGETVSAVRCYMREFGVSEEQACKKM

REMIEIEWKRLNKTTLEADEISSSVVIPSLNFTRVLEVMYDKGDGYSDSQGVTKDRIAAL

LRHAIEI

*Aquilaria crassna* AcC3 (D0VMR7)

SEQ ID NO: 4

MSSAKLGSASEDVSRRDANYHPTVWGDFFLTHSSNFLENNDSILEKHEELKQEVRNLLVV

ETSDLPSKIQLTDEIIRLGVGYHFETEIKAQLEKLHDHQLHLNFDLLTTSVWFRLLRGHG

FSIPSDVFKRFKNTKGEFETEDARTLWCLYEATHLRVDGEDILEEAIQFSRKRLEALLPK

LSFPLSECVRDALHIPYHRNVQRLAARQYIPQYDAEQTKIESLSLFAKIDFNMLQALHQS

ELREASRWWKEFDFPSKLPYARDRIAEGYYWMMGAHFEPKFSLSRKFLNRIVGITSLIDD

TYDVYGTLEEVTLFTEAVERWDIEAVKDIPKYMQVIYIGMLGIFEDFKDNLINARGKDYC

-continued

IDYAIEVFKEIVRSYQREAEYFHTGYVPSYDEYMENSIISGGYKMFIILMLIGRGEFELK

ETLDWASTIPEMVKASSLIARYIDDLQTYKAEEERGETVSAVRCYMREFGVSEEQACKKM

REMIEIEWKRLNKTTLEADEISSSVVIPSLNFTRVLEVMYDKGDGYSDSQGVTKDRIAAL

LRHAIEI

*Aquilaria crassna* AcC4 (D0VMR8)
SEQ ID NO: 5
MSSAKLGSASEDVSRRDANYHPTVWGDFFLTHSSDFLENNDSILEKHEELKQEVRNLLVV

ETSDLPSKIQLTDDIIRLGVGYHFETEIKAQLEKLHDHQLHLNFDLLTTSVWFRLLRGHG

FSISSDVFKRFKNTKGEFETEDARTLWCLYEATHLRVDGEDILEEAIQFSRKKLEALLPE

LSFPLNECVRDALHIPYHRNVQRLAARQYIPQYDAEPTKIESLSLFAKIDFNMLQALHQR

ELREASRWWKEFDFPSKLPYARDRIAEGYYWMMGAHFEPKFSLSRKFLNRIIGITSLIDD

TYDVYGTLEEVTLFTEAVERWDIEAVKDIPKYMQVIYIGMLGIFEDFKDNLINARGKDYC

IDYAIEVFKEIVRSYQREAEYFHTGYVPSYDEYMENSIISGGYKMFIILMLIGRGEFELK

ETLDWASTIPEMVKASSLIARYIDDLQTYKAEEERGETVSAVRCYMREYDVSEEEACKKM

REMIEIEWKRLNKTTLEADEVSSSVVIPSLNFTRVLEVMYDKGDGYSDSQGVTKDRIAAL

LRHAIEI

*Aquilaria crassna* AcC1mut1-M42
SEQ ID NO: 6
MSSAKLGSASEDVSRRDANYHPTVWGDFFLTHSSNFLENNDSILEKHEELKQEVRNLLVV

ETSDLPSKIQLTDEIIRLGVGYHFETEIKAQLEKLHDHQLHLNFDLLTTSVWFRLLRGHG

FSISSDVFKRFKNTKGEFETEDAWTLWCLYEATHLRVDGEDILEEAIQFSRKKLEALLPE

LSFPLNECVRDALHIPYHRNVQRLAARQYIPQYDAEPTKIESLSLFAKIDFNMLQALHQS

ELREASRWWKEFDFPSKLPYARDRIAEGYYWMMGAHFEPKFSLSRKFLNRIIGITSLIDD

TYDVYGTLEEVTLFTEAVERWDIEAVKDIPKYMQVIYTGMLGIFEDFKDNLINARGKDYC

IDYAIEVFKEIVRSYQREAEYFHTGYVPSYDEYMENSIISGGYKMFIILMLIGRGEFELK

ETLDWASTIPEMVKASSLIARYIDDLQTYKAEEERGETVSAVRCYMREFGVSEEQACKKM

REMIEIEWKRLNKTTLEADEISSSVVIPSLNFTRVLEVMYDKGDGYSDSQGVTKDRIAAL

LRHAIEI

*Aquilaria crassna* AcC1mut2-M50
SEQ ID NO: 7
MSSAKLGSASEDVSRRDANYHPTVWGDFFLTHSSNFLENNDSILEKHEELKQEVRNLLVV

ETSDLPSKIQLTDEIIRLGVGYHFETEIKAQLEKLHDHQLHLNFDLLTTSVWFRLLRGHG

FSISSDVFKRFKNTKGEFETEDARTLWCLYEATHLRVDGEDILEEAIQFSRKKLEALLPE

LSFPLNECVRDALHIPYHRNVQRLAARQYIPQYDAEPTKIESLSLFAKIDFNMLQALHQS

ELREASRWWKEFDFPSKLPYARDRIAEGYYWMMGAHFEPKFSLSRKFLNRIIGITSLIDD

TYDVYGTLEEVTLFTEAVERWDIEAVKDIPKYMQVIYTGMLGIFEDFKDNLINARGKDYC

IDYAIEVFKEIVRSYQREAEYFHTGYVPSYDEYMENSIISGGYKMFIILMLIGRGEFELK

ETLDWASTIPEMVKASSLIARYIDDLQTYKAEEERGETVSAVRCYMREFGVSEEQACKKM

REMIEIEWKRLNKTTLEADEISSSVVIPSLNFTRVLEVMYDKGDGYSDSQGVTKDRIAAL

LRHAIEI

*Aquilaria crassna* AcDGuaS3 (F6LJD3)
SEQ ID NO: 8
MSSAKLGSASEDVSRRDANYHPTVWGDFFLTHSSNFLENNDSILEKHEELKQEVRNLLVV

ETSDLPSKIQLTDEIIRLGVGYHFETEIKAQLEKLHDHQLHLNFDLLTTSVWFRLLRGHG

-continued

FSISSDVFKRFKNTKGEFETEDARTLWCLYEATHLRVDGEDILEEAIQFSRKKLEALLPE

LSFPLNECVRDALHIPYHRNVQRLAARQYIPQYDAEPTKIESLSLFAKIDFNMLQALHQR

ELREASRWWKEFDFPSKLPYARDRIAEGYYWMMGAHFEPKFSLSRKFLNRIIGITSLIDD

TYDVYGTLEEVTLFTEAVERWDIEAVKDIPKYMQVIYTGMLGIFEDFKDNLINARGKDYC

IDYAIEVFKEIVRSYQREAEYFHTGYVPSYDEYMENSIISGGYKMFIILMLIGRGEFELK

ETLDWASTIPEMVKASSLIARYIDDLQTYKAEEERGETVSAVRCYMREFGVSEEQACKKM

REMIEIEWKRLNKTTLEADEISSSVVIPSLNFTRVLEVMYDKGDGYSDSQGVTKDRIAAL

LRHAIEI

Aquilaria crassna AcDGuaS4 (F6LJD4)
SEQ ID NO: 9

MSSAKLGSASEDVSRRDANYHPTVWGDFFLTHSSNFLENNDNILEKHEELKQEVRNLLVV

ETSDLPSKIQLTDEIIRLGVGYHFEMEIKAQLEKLHDHQLHLNFDLLTTSVWFRLLRGHG

FSISSDVFKRFKNTKGEFETEDARTLWCLYEATHLRVDGEDILEEAIQFSRKRLEALLPK

LSFPLSECVRDALHIPYHRNVQRLAARQYIPQYDAEQTKIESLSLFAKIDFNMLQALHQS

ELREASRWWKEFDFPSKLPYARDRIAEGYYWMMGAHFEPKFSLSRKFLNRIIGITSLIDD

TYDVYGTLEEVTLFTEAVERWDIEAVKDIPKYMQVIYIGMLGIFEDFKDNLINARGKDYC

IDYAIEVFKEIVRSYQREAEYFHTGYVPSYDEYMENSIISGGYKMFIILMLIGRGEFELK

ETLDWASTIPEMVKASSLIARYIDDLQTYKAEEERGETVSAVRCYMREYDVSEEEACKKM

REMIEIEWKRLNKTTLEADEVSSSVVIPSLNETRVLEVMYDKGDGYSDSQGVTKDRIAAL

LRHAIEI

Aquilaria crassna AcDGuaS2 (F6LJD2)
SEQ ID NO: 10

MSSAKLGSASEDVSRRDANYHPTVWGDFFLTHSSNFLENNDSILEKHEELKQEVRNLLVV

ETIDLPSKIQLTDEIIRLGVGYHFEMEIKAQLEKLHDHQLHLNFDLLTTSVWFRLLRGHG

FSISSDVFKRFKNTKGEFETEDARTLWCLYEATHLRVDGEDILEEAIQFSRKKLEALLPE

LSFPLNECVRDALHIPYHLNVQRLAARQYIPQYDAEPTKIESLSLFAKIDFNMLQALHQS

ELREASRWWKEFDFPSKLPYARDRIAEGYYWMMGAHFEPKFSLSRKFLNRIIGITSLIDD

TYDVYGTLEEVTLFTEAVERWDIEAVKDIPKYMQVIYTGMLGIFEDFKDNLINARGKDYC

IDYAIEVFKEIVRSYQREAEYFHTGYVPSYDEYMENSIISGGYKMFIILMLIGRGEFELK

ETLDWASTIPEMVKASSLIARYIDDLQTYKAEEERGETVSAVRCYMREYGVSEEEACKKM

REMIEIEWKRLNKTTLEADEISSSVVIPSLNFTRVLEVMYDKGDGYSDSQGVTKDRIAAL

LRHAIEI

Aquilaria crassna AcDGuaS5 (F6LJD5)
SEQ ID NO: 11

MSSAKLGSASEDVSRRDANYHPTVWGDFFLTHSSNFLENNDNILEKHEELKQEVRNLLVV

ETSDLPSKIQLTDEIIRLGVGYHFEMEIKAQLEKLHDHQLHLNFDLLTTSVWFRLLRGHG

FSISSDVFKRFKNTKGEFETEDARTLWCLYEATHLRVDGEDILEEAIQFSRKRLEALLPK

LSFPLSECVRDALHIPYHRNVQRLAARQYIPQYDAEQTKIESLSLFAKIDFNMLQALHQS

ELREASRWWKEFDFPSKLPYARDRIAEGYYWMMGAHFEPKFSLSRKFLNRIIGITSLIDD

TYDVYGTLEEVTLFTEAVERWDIEAVKDIPKYMQVIYIGMLGIFEDFKDNLINARGKDYC

IDYAIEVFKEIVRSYQREAEYFHTGYVPSYDEYMENSIISGGYKMFIILMLIGRGEFELK

QTLDWASTIPEMVKASSLIARYIDDLQTYKAEEERGETVSAVRCYMREYDVSEEEACKKM

REMIEIEWKRLNKTTLEADEVSSSVVIPSLNFTRVLEVMYDKGDGYSDSQGVTKDRIAAL

LRHAIEI

-continued

*Aquilaria* spp. AmiDGuaS1 (A0A0U3ACM2)
SEQ ID NO: 12
MSSAKLGSASEDVSRRDANYHPTVWGDFFLTHSSNFLENNDNILEKHEELKQEVRNLLVV

ETSDLPSKIQLTDKIIRLGVGYHFEMEIKAQLEKLHDHQLHLNFDLLTTSVWFRLLRGHG

FSISSDVFKRFKNTKGEFETEDARTLWCLYEATHLRVDGEDILEEAIQFSRKKLEALLPE

LSFPLNECVRDALHIPYHRNVQRLAARQYIPQYDAELTKIESLSLFAKIDFNMLQALHQS

ELREASRWWKEFDFPSKLPYARDRIAEGYYWMMGAHFEPKFSLSRKFLNRIIGITSLIDD

TYDVYGTLEEVTLFTKAVERWDIEAVQDIPKYMQVIYTGMLGIFEDFKDNLINARGKDYC

IDYAIEVFKEIVRSYQREAEYFHTGYVPSYDEYMENSIISGGYKMFIILMLIGRGEFELK

ETLDWASTIPEMVKASSLIARYIDDLQTYKAEEKRGETVSAVRCYMREYGVSEEEACKKM

REMIEIEWKKLNKTTLEANEISSSVVIPSLNFTRVLEVMYDKGDGYSDSQGVTKDRIAAL

LRHAIEI

*Aquilaria* spp. AmiDGuaS2 (A0A0U3A773)
SEQ ID NO: 13
MSSAKLGSASEDVSRRDANYHPTVWGDFFLTHSSNFLENNDNILEKHEELKQEVTNLLVV

ETSDLPSKIQLTDEIIRLGVGYHFEMEIKAQLEKLHDHQLHLNFDLLTTSVWFRLLRGHG

FSISSDVFKRFKNTKGEFETEDARTLWCLYEATHLRVDGEDILEEAIQFSRKKLEALLPE

LSFPLNECVRDALHIPYHRNVQRLAARQYIPQYDAELTKIESLSLFAKIDFNMLQALHQS

ELREASRWWKEFDFPSKLPYARDRIAEGYYWMMGAHFEPKFSLSRKFLNRIIGITSLIDD

TYDVYGTLEEVTLFTEAVERWDIEAVKDIPKYMQVIYTGMLGIFEDFKDNLINARGKDYC

IDYAIEVFKEIVRSYQREAEYFHTGYVPSYDEYMENSIISGGYKMFIILMLIGRAEFELK

ETLDWASTIPEMVKASSLIARYIDDLQTYKAEEERGETVSAVRCYMREYGVSEEEACKKM

REMIEIEWKRLNKTTLEADEISSSVVIPSLNFTRVLEVMYDKGDGYSDSQGVTKGRIAAL

LRHAIEI

*Aquilaria* spp. AmiDGuaS3 (A0A023J8Z5
SEQ ID NO: 14
MSSAKLGSASEDVSRRDANYHPTVWGDFFLTHSSNFLENNHSILEKHEELKQEVRNLLVV

ETSDLPSKIQLTDKIIRLGVGYHFEMEIKAQLEKLHDHQLHLNFDLLTTSVWFRLLRGHG

FSISSDVFKRFKNTKGEFETEDARTLWCLYEATHLRVDGEDILEEAIQFSRKKLEALLPE

LSFPLNECVRDALHIPYHRNVQRLAARQYIPQYDAELTKIESLSLFAKIDFNMLQALHQS

ELREASRWWKEFDFPSKLPYARDRIAEGYYWMMGAHFEPKFSLSRKFLNRIIGITSLIDD

TYDVYGTLEEVTLFTEAVERWDIEAVKDIPKYMQVIYTGMLGIFEDFKDNLINARGKDYC

IDYAIEVFKEIVRSYQREAEYFHTGYVPSYDEYMENSIISGGYKMFIILMLIGRAEFELK

ETLDWASTIPEMVKASSLIARYIDDLQTYKAEEERGETVSAVRCYMREYGVSEEEACKKM

REMIEIEWKRLNKTTLEADEISSSVVIPSLNFTRVLEVMYDKGDGYSDSQGVTKDRIAAL

LRHAIEI

*Aquilaria* spp. AmaDGuaS1 (A0A1B0U478)
SEQ ID NO: 15
MSSAKLGSAPEDVSRRDANYHPTVWGDFFLTHSSNFLENNHSILEKHEELKQEVRNLLVV

ETSDLPSKIQLTDKIIRLGVGYHFEMEIKAQLEKLQDHQLHLNFDLLTTSVWFRLLRGHG

FSISSDVFKRFKNTKGEFETEDARTLWCLYEATHLRVDGEDILEEAIQFSRKKLEALLPE

LSFPLNECVRDALHIPYHRNVQRLAARQYIPQYDAELTKIESLSLFAKIDFNMLQALHQS

ELREASRWWKEFDFPSKLPYARDRIAEGYYWMMGAHFEPKFSLSRKFLNRIIGITSLIDD

TYDVYGTLEEVTLFTEAVERWDIEAVKDIPKYMQVIYTGMLGIFEDFKDNLINARGKDYC

-continued

IDYAIEVFKEIVRSYQREAEYFHTGYVPSYDEYMENSIISGGYKMFIILMLIGRAEFELK

ETLDWASTIPEMVKASSLIARYIDDLQTYKAEEERGETVSAVRCYMREYGVSEEEACKKM

REMIEIEWKRLNKTTLEADEISSSVVIPSLNFTRVLEVMYDKGDGYSDSQGVTKDRIATL

LRHAIEI

Aquilaria spp. AmaDGuaS2 (A0A0U2YQ77)
SEQ ID NO: 16
MSSAKLGSASEDVSRRDADYHPTVWGDFFLTHSSNFLENNHSILEKHEELKQEVRNLLVV

ETSDLPSKIQLTDKIIRLGVGYHFEMEIKAQLEKLHDHQLHLNFDLLTTSVWFRLLRGHG

FSISSDVFKRFKNTKGEFETEDARTSWCLYEATHLRVDGEDILEEAIQFSRKKLEALLPE

LSFPLNECVRDALHIPYHRNVQRLAARQYISQYDAELTKIESLSLFAKIDFNMLQALHQS

ELREASRWWKEFDFPSKLPYARDRIAEGYYWMMGAHFEPKFSLSRKFLNRIIGITSLIDD

TYDVYGTLEEVTLFTEAVERWDIEAVKDIPKYMQVIYTGMLGIFEDFKDNLINARGKDYC

IDYAIEVFKEIVRSYQREAEYFHTGYVPSYDEYMENSIISGGYKMFIILMLIGRAEFELK

ETLDWASTIPEMVKASSLIARYIDDLQTYKAEEERGETVSAVRCYMREYGVSEEEACKKM

REMIEIEWKRLNKTTLEADEISSSVVIPSLNFTRVLEVMYDKGDGYSDSQGVTKDRIA

Aquilaria spp. AsDGuaS1 (K9MQ67)
SEQ ID NO: 17
MSSAKLGSTSEDVSRRDANYHPTVWGDFFLTHSSNFLENNDSILEKHEELKQEVRNLLVV

ETSDLPSKIQLTDEIIRLGVGYHFETEIKAQLEKLHDHQLHLNFDLLTTSVWFRLLRGHG

FSISSDVFKRFKNTKGEFKTEDARTLWCLYEATHLRVDGEDVLEEAIQFSRKKLEALLPE

LSFPLSECVRDALHIPYHRNVQRLAARQYIPQYDAEPTKIESLSLFAKIDFNMLQALHQS

ELREASRWWKEFDFPSKLPYARDSIAEGYYWMMGAHFEPKFSLSRKFLNRIIGITSLIDD

TYDVYGTLEEVTLFTEAVERWDIEAVKDIPKYMQVIYTGMLGIFEDFKDNLINARGKDYC

IDYAIEVFKEIVRSYQREAEYFHTGYVPSYDEYMENSIISGGYKMFIILMLIGRGEFELK

ETLDWASTIPEMVKASSLIARYIDDLQTYKAEEKRGETVSAVRCYMREYGVSEEEACKKM

KEMIEIEWKRLNKTTLEADEISSSVVIPSLNFTRVLEVMYDKGDGYSDSQGVTKDRIAAL

LRHAIEI

Aquilaria spp. AsDGuaS2 (K9MNV6)
SEQ ID NO: 18
MSSAKLGSASEDVSRRDANYHPTVWGDFFLTHSSNFLENNDSILEKHEELKQEVRNLLVV

ETSDLPSKIQLTDEIIRLGVGYHFETEIKAQLEKLHDHQLHLNFDLLTTSVWFRLLRGHG

FSISSDVFKRFKNTKGEFKTEDARTLWCLYEATHLRVDGEDVLEEAIQFSRKKLEALLPE

LSFPLSECVRDALHIPYHRNVQRLAARQYIPQYDAEPTKIESLSLFAKIDFNMLQALHQS

ELREASRWWKEFDFPSKLPYARDRIAEGYYWMMGAHFEPKFSLSRKFLNRIIGITSLIDD

TYDVYGTLEEVTLFTEAVERWDIEAVKDIPKYMQVIYTGMLGIFEDFKDNLINARGKDYC

IDYAIEVFKEIVRSYQREAEYFHTGYVPSYDEYMENSIISGGYKMFIILMLIGRGEFELK

ETLDWASTIPEMVKASSLIARYIDDLQTYKAEEKRGETVSAVRCYMREYGVSEEEACKKM

KEMIEIEWKRLNKTTLEADEISSSVVIPSLNETRVLEVMYDKGDGYSDSQGVTKDRIAAL

LRHAIEI

Aquilaria spp. AsDGuaS3 (K9MPP8)
SEQ ID NO: 19
MSSAKLGSASEDVSRRDANYHPTVWGDFFLTHSSNFLENNDSILEKHEELKQEVRNLLVV

ETSDLPSKIQLTDEIIRLGVGYHFETEIKAQLEKLHDHQLHLNFDLLTTSVWFRLLRGHG

FSISSDVFKRFKNTKGEFKTEDARTLWCLYEATHLRVDGEDVLEEAIQFSRKKLEALLPE

LSFPLSECVRDALHIPYHRNVQRLAARQYIPQYDAEPTKIESLSLFAKIDFNMLQALHQS

-continued

ELREASRWWKEFDFPSKLPYARDRIAEGYYWMMGAHFEPKFSLSRKFLNRIIGITSLIDD

TYDVYGTLEEVTLFTEAVERWDIEAVKDIPKYMQVIYTGMLGIFEDFKDNLINARGKDYC

IDYAIEVFKEIVRSYQREAEYFHTGYVPSYDEYMENSIISGGYKMFIILMLIGRGEFELK

ETLDWASTIPEMVKASSLIARYIDDLQTYKAEEERGETVSAVRCYMREYGVSEEEACKKM

REMIEIEWKRLNKTTLEADEISSSVVIPSLNFTRVLEVMYDKGDGYSDSQGVTKDRIAAL

LRHAIEI

*Aquilaria* spp. AsDGuaS4 (M9SVT6)
SEQ ID NO: 20

MSSAKLGSASEDVSRRDANYHPTVWGDFFLTHSSNFLENNDNILEKHEELKQEVRNLLVV

ETSDLPSKIQLTDEIIRLGVGYHFEMEIKAQLEKLHDHQLHLNFDLLTTSVWFRLLRGHG

FSISSDVFKRFKNTKGEFETEDARTLWCLYEATHLRVDGEDILEEAIQFSRKRLEALLPK

LSFPLSECVRDALHIPYHRNVQRLAARQYIPQYDAEQTKIESLSLFAKIDFNMLQALRQS

ELREASRWWKEFDFPSKLPYARDRIAEGYYWMMGAHFEPKFSLSRKFLNRIIGITSLIDD

TYDVYGTLEEVTLFTEAVERWDIEAVKDIPKYMQVIYTGMLGIFEDFKDNLINARGKDYC

IDYAIEVFKEIVRSYQREAEYFHTGYVPSYDEYMENSIISGGYKMFIILMLIGRGEFELK

ETLDWASTIPEMVKASSLIARYIDDLQTYKAEEERGETVSAVRCYMREFGVSEEQACKKM

REMIEIEWKRLNKTTLEADEISSSVVIPSLNFTRVLEVMYDKGDGYSDSQGVTKDRIAAL

LRHAIEI

*V. vinifera* germacrene D synthase (VvGDS)
SEQ ID NO: 21

MSVPLSVSVTPILSQRIDPEVARHEATYHPNFWGDRFLHYNPDDDFCGTHACKEQQIQEL

KEEVRKSLEATAGNTSQLLKLIDSIQRLGLAYHFEREIEEALKAMYQTYTLVDDNDHLTT

VSLLFRLLRQEGYHIPSDVFKKFMDEGGNFKESLVGDLPGMLALYEAAHLMVHGEDILDE

ALGFTTAHLQSMAIDSDNPLTKQVIRALKRPIRKGLPRVEARHYITIYQEDDSHNESLLK

LAKLDYNMLQSLHRKELSEITKWWKGLDFATKLPFARDRIVEGYFWILGVYFEPQYYLAR

RILMKVFGVLSIVDDIYDAYGTFEELKLFTEAIERWDASSIDQLPDYMKVCYQALLDVYE

EMEEEMTKQGKLYRVHYAQAALKRQVQAYLLEAKWLKQEYIPRMDEYMSNALVSSACSML

TTTSFVGMGDIVTKEAFDWVFSDPKMIRASNVICRLMDDIVSHEFEQKRGHVASAVECYM

KQYGVSKEEAYDEFKKQVESAWKDNNEEFLQPTAVPVPLLTRVLNFSRMMDVLYKDEDEY

TLVGPLMKDLVAGMLIDPVPM

α-Guaiene Oxidase
*V. vinifera* VvSTO2 (F6I534; Engineered CYP71BE5 α-guaiene 2-oxidase)
SEQ ID NO: 22

MELQFSFFPILCTFLLFIYLLKRLGKPSRTNHPAPKLPPGPWKLPIIGNMHQLVGSLPHR

SLRSLAKKHGPLMHLQLGEVSAIVVSSREMAKEVMKTHDIIFSQRPCILAASIVSYDCTD

IAFAPYGGYWRQIRKISVLELLSAKRVQSFRSVREEEVLNLVRSVSLQEGVLINLTKSIF

SLTFSIISRTAFGKKCKDQEAFSVTLDKFADSAGGFTIADVFPSIKLLHVVSGMRRKLEK

VHKKLDRILGNIINEHKARSAAKETCEAEVDDDLVDVLLKVQKQGDLEFPLTMDNIKAVL

LDLFVAGTETSSTAVEWAMAEMLKNPRVMAKAQAEVRDIESRKGNADETVVRELKFLKLV

-continued

IKETLRLHPPVPLLIPRESRERCAINGYEIPVKTRVIINAWAIARDPKYWTDAESFNPER

FLDSSIDYQGTNFEYIPFGAGRRMCPGILFGMANVELALAQLLYHFDWKLPNGARHEELD

MTEGFRTSTKRKQDLYLIPITYRPLPVE

*B. subtilis* BsAGOX1 (O31440; cypC CYP152A1)
SEQ ID NO: 23

MNEQIPHDKSLDNSLTLLKEGYLFIKNRTERYNSDLFQARLLGKNFICMTGAEAAKVFYD

TDRFQRQNALPKRVQKSLFGVNAIQGMDGSAHIHRKMLFLSLMTPPHQKRLAELMTEEWK

AAVTRWEKADEVVLFEEAKEILCRVACYWAGVPLKETEVKERADDFIDMVDAFGAVGPRH

WKGRRARPRAEEWIEVMIEDARAGLLKTTSGTALHEMAFHTQEDGSQLDSRMAAIELINV

LRPIVAISYFLVFSALALHEHPKYKEWLRSGNSREREMFVQEVRRYYPFGPPFLGALVKKD

FVWNNCEFKKGTSVLLDLYGTNHDPRLWDHPDEFRPERFAEREENLFDMIPQGGGHAEKG

HRCPGEGITIEVMKASLDFLVHQIEYDVPEQSLHYSLARMPSLPESGFVMSGIRRKS

*B. subtilis* BsAGOX1 (A5HNX5; pksS CYP107K1)
SEQ ID NO: 24

MQMEKLMFHPHGKEFHHNPFSVLGRFREEEPIHRFELKRFGATYPAWLITRYDDCMAFLK

DNRITRDVKNVMNQEQIKMLNVSEDIDFVSDHMLAKDTPDHTRLRSLVHQAFTPRTIENL

RGSIEQIAEQLLDEMEKENKADIMKSFASPLPFIVISELMGIPKEDRSQFQIWTNAMVDT

SEGNRELTNQALREFKDYIAKLIHDRRIKPKDDLISKLVHAEENGSKLSEKELYSMLFLL

VVAGLETTVNLLGSGTLALLQHKKECEKLKQQPEMIATAVEELLRYTSPVVMMANRWAIE

DFTYKGHSIKRGDMIFIGIGSANRDPNFFENPEILNINRSPNRHISFGFGIHFCLGAPLA

RLEGHIAFKALLKRFPDIELAVAPDDIQWRKNVFLRGLESLPVSLSK

*B. cereus* BcAGOX1 (Q737I9; BCE_2659 CYP106)
SEQ ID NO: 25

MASPENVILVHEISKLKTKEELWNPYEWYQFMRDNHPVHYDEEQDVWNVFLYEDVNRVLS

DYRLFSSRRERRQFSIPPLETRININSTDPPEHRNVRSIVSKAFTPRSLEQWKPRIQAIA

NELVQHIGKYSEVNIVEEFAAPLPVTVISDLLGVPTTDRKKIKAWSDILFMPYSKEKFND

LDVEKGIALNEFKAYLLPIVQEKRYHLTDDIISDLIRAEYEGERLTDEEIVTFSLGLLAA

GNETTTNLIINSFYCFLVDSPGTYKELREEPTLISKAIEEVLRYRFPITLARRITEDTNI

FGPLMKKDQMVVAWVSAANLDEKKFSQASKFNIHRIGNEKHLTFGKGPHFCLGAPLARLE

AEIALTTFINAFEKIALSPSFNLEQCILENEQTLKFLPICLKTQ

*B. cereus* BcAGOX2 (Q737F3; cypA BCE_2696 CYP107)
SEQ ID NO: 26

MKKLTFNDLNSPETMRNPIMFYKNLMEQKERFFHIDDFYGMGGAWVVFHYDDVVAILKDS

RFIKDLRKFTPPHYKQNPIEENTAVSKLFEWLMNMPNMLTVDPPDHTRLRRLVSKSFTPR

MIEDLRPRIQQIADELLDVVQEQRKMEIIADFAYPLPIIVISEMLGIPATDRNQFRAWTQ

ELMKASVDPGQGTTVTATLEKFINYIEILFNEKHLNPSDDLISALVQAKEQEDKLSKNEL

LSTIWLLIIAGHETTVNLISNGVLALLQHPEQMNLLRQDPSLLASAVDELLRYAGPIMFS

SRFASEDVTIHGNRIRKGELVLLSLTAANIDPNIFPYPEELNISREENNHLAFGAGIHQC

LGAPLARLEGQIALDTLLKRLPNLRLAIEADQLIYNHSKIRSLASLPVIF

*Nicotiana tomentosiformis* NtKO
SEQ ID NO: 45

MDAILNLQTVPLGTALTIGGPAVALGGISLWFLKEYVNDQKRKSSNFLPPLPEVPGLPVI

GNLLQLTEKKPHKTFTNWAETYGPIYSIKTGANTIVVLNTNELAKEAMVTRYSAISTRKL

TNALKILTCDKSIVAISDYDEFHKTVKRHVLTSVLGPNAQKRHRIHRDTLIENVSKQLHD

LVRKYPNEAVNLRKIFQSELFGLALKQALGKDIESIYVEGLDATLPREDVLKTLVLDIME

GAIDVDWRDFFPYLKWVPNKSFENRIQRKHLRREAVMKALIMEQRKRINSGEKLNSYIDY

-continued

LSSEANTLTEKQILMLLWEAIIETSDTTVVSTEWAMYELAKDPKRQEQLFLEIQNVCGSN

KITEEKLCQLPYLCAVFHETLRKHSPVPIVPLRYVHEDTQLGGYHIPKGAEIAINIYGCN

RDKKVWESPEEWKPERFLDGKYDPVELQKTMAFGGGKRVCAGALQAMTITCTTIARLIQE

FEWSLKDGEEENVATMGLTTHKLHPMQAHIKPRK

*Lactuca sativa* LsKO

SEQ ID NO: 46

MDGVIDMQTIPLRTAIAIGGTAVALVVALYFWFLRSYASPSHHSNHLPPVPEVPGVPVLG

NLLQLKEKKPYMTFTKWAEMYGPIYSIRTGATSMVVVSSNEIAKEVVVTRFPSISTRKLS

YALKVLTEDKSMVAMSDYHDYHKTVKRHILTAVLGPNAQKKFRAHRDTMMENVSNELHAF

FEKNPNQEVNLRKIFQSQLFGLAMKQALGKDVESIYVKDLETTMKREEIFEVLVVDPMMG

AIEVDWRDFFPYLKWVPNKSFENIIHRMYTRREAVMKALIQEHKKRIASGENLNSYIDYL

LSEAQTLTDKQLLMSLWEPIIESSDTTMVTTEWAMYELAKNPNMQDRLYEEIQSVCGSEK

ITEENLSQLPYLYAVFQETLRKHCPVPIMPLRYVHENTVLGGYHVPAGTEVAINIYGCNM

DKKVWENPEEWNPERFLSEKESMDLYKTMAFGGGKRVCAGSLQAMVISCIGIGRLVQDFE

WKLKDDAEEDVNTLGLTTQKLHPLLALINPRK

*Cynara cardunculus* var. *scolymus* CcKO

SEQ ID NO: 47

MDMQSIPAIAIGSTAVAIALGLFFWFFRRHVPDHIDHPNHLPSVPEVPGIPVLGNLLQLK

EKKPYMTFTKWAETYGPIYSIRTGAISMVVVSSNAIAKEALVTRFPSISTRKLSKALEVL

TADKTMVAMSDYNDYHKTVKRHILTAVLGPNAQKKHRVHRDIMMQNLSNQLHTFVQNSPQ

EEVNLRKVFQSELFGLAMRQTMGKDVESIYVEDLGTTMNRDEIFQVLVVDPLMGAIEVDW

RDFFPYLKWIPNRNFENTIQQMYIRREAVMKALIQEHRKRIASGENLNSYIDYLLSEAQT

LSEKQLXMSLWEPIIESSDTTMVTTEWAMYELAKNPKIQDRLYREIQGVCGSDKIXEENL

GQLPYLSAIFNETLRRHGPVPIIPLRYVHEDTELGGYHIPAGTQIAVNIYGCNMEKAVWE

NPEEWNPERFFEVEGDQKTMAFGGGKRVCAGSLQAMLIACIGIGRMVQEFEWKLKDEAAQ

EDVNTLGLTTQKLRPLHAIIYPRKENDAKVWKC

*Artemisia annua* AaKO

SEQ ID NO: 49

MDALTDMLQIPPATPITVAITTVTIAVAIFLYIKSHASNHSRRSTHLPPVPEVPGVPVLG

NLLQLKEKKPYLTFTRWAQTYGAIYSIRTGATSMVVSSSEIAKEAMVTRFSSISTRNLS

KALTILTADKTMVAMSDYNDYHRTVKRHILTAMLGPNAQRKQRVHRDFMIENISKQLHAF

VENSPKEEVDLRKIFQSELFGLAMKQAVGKDVESLNVEDLGVTMKRDEIFQVLVVDPMMG

AIEVDWRDFFPYLKWVPNKKFENTIQQMYIRRKAVMKALIKEHKKRIASGENLNSYIDYL

LSEAQTFTDEQLIMSLWEPIIESSDTTMVTTEWAMYELAKNPKMQDRLYRDIQSVCGSDK

ITEENLSQLPYLSAIFHETLRRHSPVPIIPLRHVHEDTVLGGYHVPAGTELAVNIYGCNM

EKNVWENPEEYNPDRFMKENETIDMQRTMAFGGGKRVCAGSLQAMLISCIGIGRMVQEEE

WRFKDKAEEDINTLGLTTQRLNPLRAIIKPRN

*Helianthus annuus* HaKO

SEQ ID NO: 50

MDALTGMLPIPPATALAIGGTAIALAVAISFWFLRSYTSGESNRLPRVPEVPGVPVLGNL

LQLKEKKPYMTFTRWAETYGPIYSIRTGATSMVVVSSNEIAKEAFVTRFESISTRNLSKA

LKILTDDKTMVAMSDYNDYHKTVKRHILTAMLGPNAQKKHRIQRDIMMENLSNRLHAFVK

TSTEQEEVDLREIFQSELFGLAMRQTMGKDVESIYVEDLKITMKRDEIFQVLVVDPMMGA

IDVDWRDFFPYLKWVPNKKFENTIQQMYIRREAVMKALIKQHKERIASGEKLNSYIDYLL

```
SEAQSLTDRQLLMSVWEPIIESSDTTMVTTEWAIYELAKNPHIQDRLYRDIQSVCGSDII

KEEHLSQLPEITAIFHETLRRHSPVPIIPLRYVHEDTVLGGYHVPAGTELAINIYGCNME

KSVWENPEEWNPERFMKENETIDFQKTMAFGGGKRVCAGSLQAMLISCVGIGRMVQEFKW

ELKNKAQEEVNTIGLTTQMLRPLRAIIKPRN
```

Engineered Kaurene Oxidase (KOeng)
SEQ ID NO: 51
```
MAWEYALIGLVVGIIIGAVAMRWYLKSYTSARRSQSNHLPRVPEVPGVPLLGNLLQLKEK

KPYMTFTKWAATYGPIYSIKTGATSVVVVSSNEIAKEALVTRFQSISTRNLSKALKVLTA

DKQMVAMSDYDDYHKTVKRHILTAVLGPNAQKKHRIHRDIMMDNISTQLHEFVKNNPEQE

EVDLRKIFQSELFGLAMRQALGKDVESLYVEDLKITMNRDEILQVLVVDPMMGAIDVDWR

DFFPYLKWVPNKKFENTIQQMYIRREAVMKSLIKEQKKRIASGEKLNSYIDYLLSEAQTL

TDQQLLMSLWEPIIESSDTTMVTTEWAMYELAKNPKLQDRLYRDIKSVCGSEKITEEHLS

QLPYITAIFHETLRKHSPVPILPLRHVHEDTVLGGYHVPAGTELAVNIYGCNMDKNVWEN

PEEWNPERFMKENETIDFQKTMAFGGGKRVCAGSLQALLIASIGIGRMVQEFEWKLKDMT

QEEVNTIGLTNQMLRPLRAIIKPRI
```

*Helianthus annuus* germacrene A monooxygenase; Engineered HaGAO
SEQ ID NO: 52
```
MAKPPLFFIVIIGLIVVAASFLYKLLTRPTSSKNRLPEPWRLPIIGHMHHLIGTMPHRGV

MDLARKYGSLMHLQLGEVSAIVVSSPKWAKEILTTYDIPFANRPETLTGEIIAYHNTDIV

LAPYGEYWRQLRKLCTLELLSVKKVKSFQSLREEECWNLVQEIKASGSGTPFNLSEGIFK

VIATVLSRAAFGKGIKDQKQFTEIVKEILRETGGFDVADIFPSKKFLHHLSGKRGRLTSI

HNKLDSLINNLVAEHTVSKSSKVNETLLDVLLRLKNSEEFPLTADNVKAIILDMFGAGTD

TSSATVEWAISELIRCPRAMEKVQAELRQALNGKERIKEEEIQDLPYLNLVIRETLRLHP

PLPLVMPRECRQAMNLAGYDVANKTKLIVNVFAINRDPEYWKDAESFNPERFENSNTTIM

GADYEYLPFGAGRRMCPGSALGLANVQLPLANILYYFKWKLPNGASHDQLDMTESFGATV

QRKTELMLVPSF
```

Alpha-humulene 10-hydroxylase; Engineered CYP71BA1
SEQ ID NO: 54
```
MAQDLRLILIIVGAIAIIALLVHGFLLIKRSSRSSVHKQQVLLASLPPSPPRLPLIGNIH

QLVGGNPHRILLQLARTHGPLICLRLGQVDQVVASSVEAVEEIIKRHDLKFADRPRDLTF

SRIFFYDGNAVVMTPYGGEWKQMRKIYAMELLNSRRVKSFAAIREDVARKLTGEIAHKAF

AQTPVINLSEMVMSMINAIVIRVAFGDKCKQQAYFLHLVKEAMSYVSSFSVADMYPSLKF

LDTLTGLKSKLEGVHGKLDKVFDEIIAQRQAALAAEQAEEDLIIDVLLKLKDEGNQEFPI

TYTSVKAIVMEIFLAGTETSSSVIDWVMSELIKNPKAMEKVQKEMREAMQGKTKLEESDI

PKFSYLNLVIKETLRLHPPGPLLFPRECRETCEVMGYRVPAGARLLINAFALSRDEKYWG

SDAESFKPERFEGISVDFKGSNFEFMPFGAGRRICPGMTFGISSVEVALAHLLFHFDWQL

PQGMKIEDLDMMEVSGMSATRRSPLLVLAKLIIPLP
```

Ent-isokaurene C2-hydroxylase; Engineered CYP71Z18
SEQ ID NO: 55
```
MAQDLRLILIIVGAIAIIALLVHGFLKSAVTKPKLNLPPGPWTLPLIGSIHHIVSNPLPY

RAMRELAHKHGPLMMLWLGEVPTLVVSSPEAAQAITKTHDVSFADRHINSTVDILTFNGM

DMVFGSYGEQWRQLRKLSVLELLSAARVQSFQRIREEEVARFMRSLAASASAGATVDLSK

MISSFINDTFVRESIGSRCKYQDEYLAALDTAIRVAAELSVGNIFPSSRVLQSLSTARRK

AIASRDEMARILGQIIRETKESMDQGDKTSNESMISVLLRLQKDAGLPIELTDNVVMALM

FDLFGAGSDTSSTTLTWCMTELVRYPATMAKAQAEVREAFKGKTTITEDDLSTANLRYLK
```

LVVKEALRLHCPVPLLLPRKCREACQVMGYDIPKGTCVFVNVWAICRDPRYWEDAEEFKP

ERFENSNLDYKGTYYEYLPFGSGRRMCPGANLGVANLELALASLLYHFDWKLPSGQEPKD

VDVWEAAGLVAKKNIGLVLHPVSHIAPVNA

Premnaspirodiene oxygenase; Engineered CYP71D55_V482I/A484I
SEQ ID NO: 56

MAQDLRLILIIVGAIAIIALLVHGFFLLRKWKNSNSQSKKLPPGPWKLPLLGSMLHMVGG

LPHHVLRDLAKKYGPLMHLQLGEVSAVVVTSPDMAKEVLKTHDIAFASRPKLLAPEIVCY

NRSDIAFCPYGDYWRQMRKICVLEVLSAKNVRSFSSIRRDEVLRLVNFVRSSTSEPVNET

ERLFLFTSSMTCRSAFGKVFKEQETFIQLIKEVIGLAGGFDVADIFPSLKFLHVLTGMEG

KIMKAHHKVDAIVEDVINEHKKNLAMGKTNGALGGEDLIDVLLRLMNDGGLQFPITNDNI

KAIIFDMFAAGTETSSSTLVWAMVQMMRNPTILAKAQAEVREAFKGKETFDENDVEELKY

LKLVIKETLRLHPPVPLLVPRECREETEINGYTIPVKTKVMVNVWALGRDPKYWDDADNF

KPERFEQCSVDFIGNNFEYLPFGGGRRICPGISFGLANVYLPLAQLLYHFDWKLPTGMEP

KDLDLTELVGITIARKSDLMLVATPYQPSRE

Cytochrome P450 Reductase
Stevia rebaudiana SrCPR
SEQ ID NO: 27

MAQSDSVKVSPFDLVSAAMNGKAMEKLNASESEDPTTLPALKMLVENRELLTLFTTSFAV

LIGCLVFLMWRRSSSKKLVQDPVPQVIVVKKKEKESEVDDGKKKVSIFYGTQTGTAEGFA

KALVEEAKVRYEKTSFKVIDLDDYAADDDEYEEKLKKESLAFFFLATYGDEPTDNAANF

YKWFTEGDDKGEWLKKLQYGVFGLGNRQYEHFNKIAIVVDDKLTEMGAKRLVPVGLGDDD

QCIEDDFTAWKELVWPELDQLLRDEDDTSVTTPYTAAVLEYRVVYHDKPADSYAEDQTHT

NGHVVHDAQHPSRSNVAFKKELHTSQSDRSCTHLEFDISHTGLSYETGDHVGVYSENLSE

VVDEALKLLGLSPDTYFSVHADKEDGTPIGGASLPPPFPPCTLRDALTRYADVLSSPKKV

ALLALAAHASDPSEADRLKFLASPAGKDEYAQWIVANQRSLLEVMQSFPSAKPPLGVFFA

AVAPRLQPRYYSISSSPKMSPNRIHVTCALVYETTPAGRIHRGLCSTWMKNAVPLTESPD

CSQASIFVRTSNFRLPVDPKVPVIMIGPGTGLAPFRGFLQERLALKESGTELGSSIFFFG

CRNRKVDFIYEDELNNFVETGALSELIVAFSREGTAKEYVQHKMSQKASDIWKLLSEGAY

LYVCGDAKGMAKDVHRTLHTIVQEQGSLDSSKAELYVKNLQMSGRYLRDVW

Arabidopsis thaliana AtCPR1
SEQ ID NO: 28

MATSALYASDLFKQLKSIMGTDSLSDDVVLVIATTSLALVAGEVVLLWKKTTADRSGELK

PLMIPKSLMAKDEDDDLDLGSGKTRVSIFFGTQTGTAEGFAKALSEEIKARYEKAAVKVI

DLDDYAADDDQYEEKLKKETLAFFCVATYGDEPTDNAARFYKWFTEENERDIKLQQLAY

GVFALGNRQYEHFNKIGIVLDEELCKKGAKRLIEVGLGDDDQSIEDDFNAWKESLWSELD

KLLKDEDDKSVATPYTAVIPEYRVVTHDPRFTTQKSMESNVANGNTTIDIHHPCRVDVAV

QKELHTHESDRSCIHLEFDISRTGITYETGDHVGVYAENHVEIVEEAGKLLGHSLDLVFS

IHADKEDGSPLESAVPPPFPGPCTLGTGLARYADLLNPPRKSALVALAAYATEPSEAEKL

KHLTSPDGKDEYSQWIVASQRSLLEVMAAFPSAKPPLGVFFAAIAPRLQPRYYSISSSPR

LAPSRVHVTSALVYGPTPTGRIHKGVCSTWMKNAVPAEKSHECSGAPIFIRASNFKLPSN

PSTPIVMVGPGTGLAPFRGFLQERMALKEDGEELGSSLLFFGCRNRQMDFIYEDELNNFV

-continued

DQGVISELIMAFSREGAQKEYVQHKMMEKAAQVWDLIKEEGYLYVCGDAKGMARDVHRTL

HTIVQEQEGVSSSEAEAIVKKLQTEGRYLRDVW

*A. thaliana* AtCPR2
SEQ ID NO: 29
MASSSSSSSTSMIDLMAAIIKGEPVIVSDPANASAYESVAAELSSMLIENRQFAMIVTTS

IAVLIGCIVMLVWRRSGSGNSKRVEPLKPLVIKPREEEIDDGRKKVTIFFGTQTGTAEGF

AKALGEEAKARYEKTRFKIVDLDDYAADDDEYEEKLKKEDVAFFFLATYGDGEPTDNAAR

FYKWFTEGNDRGEWLKNLKYGVFGLGNRQYEHFNKVAKVVDDILVEQGAQRLVQVGLGDD

DQCIEDDFTAWREALWPELDTILREEGDTAVATPYTAAVLEYRVSIHDSEDAKFNDINMA

NGNGYTVFDAQHPYKANVAVKRELHTPESDRSCIHLEFDIAGSGLTYETGDHVGVLCDNL

SETVDEALRLLDMSPDTYFSLHAEKEDGTPISSSLPPPFPPCNLRTALTRYACLLSSPKK

SALVALAAHASDPTEAERLKHLASPAGKDEYSKWVVESQRSLLEVMAEFPSAKPPLGVFF

AGVAPRLQPRFYSISSSPKIAETRIHVTCALVYEKMPTGRIHKGVCSTWMKNAVPYEKSE

NCSSAPIFVRQSNFKLPSDSKVPIIMIGPGTGLAPFRGFLQERLALVESGVELGPSVLFF

GCRNRRMDFIYEEELQRFVESGALAELSVAFSREGPTKEYVQHKMMDKASDIWNMISQGA

YLYVCGDAKGMARDVHRSLHTIAQEQGSMDSTKAEGFVKNLQTSGRYLRDVW

*A. thaliana* eATR2
SEQ ID NO: 30
MASSSSSSSTSMIDLMAAIIKGEPVIVSDPANASAYESVAAELSSMLIENRQFAMIVTTS

IAVLIGCIVMLVWRRSGSGNSKRVEPLKPLVIKPREEEIDDGRKKVTIFFGTQTGTAEGF

AKALGEEAKARYEKTRFKIVDLDDYAADDDEYEEKLKKEDVAFFFLATYGDGEPTDNAAR

FYKWFTEGNDRGEWLKNLKYGVFGLGNRQYEHFNKVAKVVDDILVEQGAQRLVQVGLGDD

DQCIEDDFTAWREALWPELDTILREEGDTAVATPYTAAVLEYRVSIHDSEDAKFNDITLA

NGNGYTVFDAQHPYKANVAVKRELHTPESDRSCIHLEFDIAGSGLTMKLGDHVGVLCDNL

SETVDEALRLLDMSPDTYFSLHAEKEDGTPISSSLPPPFPPCNLRTALTRYACLLSSPKK

SALVALAAHASDPTEAERLKHLASPAGKDEYSKWVVESQRSLLEVMAEFPSAKPPLGVFF

AGVAPRLQPRFYSISSSPKIAETRIHVTCALVYEKMPTGRIHKGVCSTWMKNAVPYEKSE

KLFLGRPIFVRQSNFKLPSDSKVPIIMIGPGTGLAPFRGFLQERLALVESGVELGPSVLF

FGCRNRRMDFIYEEELQRFVESGALAELSVAFSREGPTKEYVQHKMMDKASDIWNMISQG

AYLYVCGDAKGMARDVHRSLHTIAQEQGSMDSTKAEGFVKNLQTSGRYLRDVW

*S. rebaudiana* SrCPR3
SEQ ID NO: 32
MAQSNSVKISPLDLVTALFSGKVLDTSNASESGESAMLPTIAMIMENRELLMILTTSVAV

LIGCVVVLVWRRSSTKKSALEPPVIVVPKRVQEEEVDDGKKKVTVFFGTQTGTAEGFAKA

LVEEAKARYEKAVFKVIDLDDYAADDDEYEEKLKKESLAFFFLATYGDGEPTDNAARFYK

WFTEGDAKGEWLNKLQYGVFGLGNRQYEHFNKIAKVVDDGLVEQGAKRLVPVGLGDDDQC

IEDDFTAWKELVWPELDQLLRDEDDTTVATPYTAAVAEYRVVFHEKPDALSEDYSYTNGH

AVHDAQHPCRSNVAVKKELHSPESDRSCTHLEFDISNTGLSYETGDHVGVYCENLSEVVN

DAERLVGLPPDTYFSIHTDSEDGSPLGGASLPPPFPPCTLRKALTCYADVLSSPKKSALL

ALAAHATDPSEADRLKFLASPAGKDEYSQWIVASQRSLLEVMEAFPSAKPSLGVFFASVA

PRLQPRYYSISSSPKMAPDRIHVTCALVYEKTPAGRIHKGVCSTWMKNAVPMTESQDCSW

-continued

APIYVRTSNFRLPSDPKVPVIMIGPTGLAPFRGFLQERLALKEAGTDLGLSILFFGCRN

RKVDFIYENELNNFVETGALSELIVAFSREGPTKEYVQHKMSEKASDIWNLLSEGAYLYV

CGDAKGMAKDVHRTLHTIVQEQGSLDSSKAELYVKNLQMSGRYLRDVW

Artemisia annua AaCPR
SEQ ID NO: 33

MAQSTTSVKLSPFDLMTALLNGKVSFDTSNTSDTNIPLAVEMENRELLMILTTSVAVLIG

CVVVLVWRRSSSAAKKAAESPVIVVPKKVTEDEVDDGRKKVTVFFGTQTGTAEGFAKALV

EEAKARYEKAVFKVIDLDDYAAEDDEYEEKLKKESLAFFFLATYGDGEPTDNAARFYKWF

TEGEEKGEWLDKLQYAVFGLGNRQYEHFNKIAKVVDEKLVEQGAKRLVPVGMGDDDQCIE

DDFTAWKELVWPELDQLLRDEDDTSVATPYTAAVAEYRVVFHDKPETYDQDQLTNGHAVH

DAQHPCRSNVAVKKELHSPLSDRSCTHLEFDISNTGLSYETGDHVGVYVENLSEVVDEAE

KLIGLPPHTYFSVHADNEDGTPLGGASLPPPFPPCTLRKALASYADVLSSPKKSALLALA

AHATDSTEADRLKFLASPAGKDEYAQWIVASHRSLLEVMEAFPSAKPPLGVFFASVAPRL

QPRYYSISSSPRFAPNRIHVTCALVYEQTPSGRVHKGVCSTWMKNAVPMTESQDCSWAPI

YVRTSNFRLPSDPKVPVIMIGPTGLAPFRGFLQERLAQKEAGTELGTAILFFGCRNRKV

DFIYEDELNNFVETGALSELVTAFSREGATKEYVQHKMTQKASDIWNLLSEGAYLYVCGD

AKGMAKDVHRTLHTIVQEQGSLDSSKAELYVKNLQMAGRYLRDVW

Pelargonium graveolens PgCPR
SEQ ID NO: 34

MAQSSSGSMSPFDFMTAIIKGKMEPSNASLGAAGEVTAMILDNRELVMILTTSIAVLIGC

VVVFIWRRSSSQTPTAVQPLKPLLAKETESEVDDGKQKVTIFFGTQTGTAEGFAKALADE

AKARYDKVTFKVVDLDDYAADDEEYEEKLKKETLAFFFLATYGDGEPTDNAARFYKWFLE

GKERGEWLQNLKFGVFGLGNRQYEHFNKIAIVVDEILAEQGGKRLISVGLGDDDQCIEDD

FTAWRESLWPELDQLLRDEDDTTVSTPYTAAVLEYRVVFHDPADAPTLEKSYSNANGHSV

VDAQHPLRANVAVRRELHTPASDRSCTHLEFDISGTGIAYETGDHVGVYCENLAETVEEA

LELLGLSPDTYFSVHADKEDGTPLSGSSLPPPFPPCTLRTALTLHADLLSSPKKSALLAL

AAHASDPTEADRLRHLASPAGKDEYAQWIVASQRSLLEVMAEFPSAKPPLGVFFASVAPR

LQPRYYSISSSPRIAPSRIHVTCALVYEKTPTGRVHKGVCSTWMKNSVPSEKSDECSWAP

IFVRQSNFKLPADAKVPIIMIGPTGLAPFRGFLQERLALKEAGTELGPSILFFGCRNSK

MDYIYEDELDNFVQNGALSELVLAFSREGPTKEYVQHKMMEKASDIWNLISQGAYLYVCG

DAKGMARDVHRTLHTIAQEQGSLDSSKAESMVKNLQMSGRYLRDVW

Camptotheca acuminata cytochrome P450 reductase; CaCPR
SEQ ID NO: 53

MAQSSSVKVSTFDLMSAILRGRSMDQTNVSFESGESPALAMLIENRELVMILTTSVAVLI

GCFVVLLWRRSSGKSGKVTEPPKPLMVKTEPEPEVDDGKKKVSIFYGTQTGTAEGFAKAL

AEEAKVRYEKASFKVIDLDDYAADDEEYEEKLKKETLTFFFLATYGDGEPTDNAARFYKW

FMEGKERGDWLKNLHYGVFGLGNRQYEHFNRIAKVVDDTIAEQGGKRLIPVGLGDDDQCI

EDDFAAWRELLWPELDQLLQDEDGTTVATPYTAAVLEYRVVFHDSPDASLLDKSFSKSNG

HAVHDAQHPCRANVAVRRELHTPASDRSCTHLEFDISGTGLVYETGDHVGVYCENLIEVV

EEAEMLLGLSPDTFFSIHTDKEDGTPLSGSSLPPPFPPCTLRRALTQYADLLSSPKKSSL

LALAAHCSDPSEADRLRHLASPSGKDEYAQWVVASQRSLLEVMAEFPSAKPPIGAFFAGV

-continued

APRLQPRYYSISSSPRMAPSRIHVTCALVFEKTPVGRIHKGVCSTWMKNAVPLDESRDCS

WAPIFVRQSNFKLPADTKVPVLMIGPGTGLAPFRGFLQERLALKEAGAELGPAILFFGCR

NRQMDYIYEDELNNFVETGALSELIVAFSREGPKKEYVQHKMMEKASDIWNMISQEGYIY

VCGDAKGMARDVHRTLHTIVQEQGSLDSSKTESMVKNLQMNGRYLRDVW

Alcohol Dehydrogenase
Brachypodium distachyon BdDH
SEQ ID NO: 35
MSAAAAVSSSSSPRLEGKVALVTGGASGIGEAIVRLFRQHGAKVCIADVQDEAGQQVRDS

LGDDAGTDVLFVHCDVTVEEDVSRAVDAAAEKFGTLDIMVNNAGITGDKVTDIRNLDFAE

VRKVFDINVHGMLLGMKHAARVMIPGKKGSIVSLASVASVMGGMGPHAYTASKHAVVGLT

KSVALELGKHGIRVNCVSPYAVPTALSMPHLPQGEHKGDAVRDFLAFVGGEANLKGVDLL

PKDVAQAVLYLASDEARYISALNLVVDGGFTSVNPNLKAFED

Citrus sinensis CsABA2
SEQ ID NO: 36
MSNSNSTDSSPAVQRLVGRVALITGGATGIGESTVRLFHKHGAKVCIADVQDNLGQQVCQ

SLGGEPDTFFCHCDVTKEEDVCSAVDLTVEKFGTLDIMVNNAGISGAPCPDIREADLSEF

EKVFDINVKGVFHGMKHAARIMIPQTKGTIISICSVAGAIGGLGPHAYTGSKHAVLGLNK

NVAAELGKYGIRVNCVSPYAVATGLALAHLPEEERTEDAMVGFRNFVARNANMQGTELTA

NDVANAVLFLASDEARYISGTNLMVDGGFTSVNHSLRVFR

Citrus sinensis CsDH
SEQ ID NO: 37
MATPPISSLISQRLLGKVALVTGGASGIGEGIVRLFHRHGAKVCFVDVQDELGYRLQESL

VGDKDSNIFYSHCDVTVEDDVRRAVDLTVTKFGTLDIMVNNAGISGTPSSDIRNVDVSEF

EKVFDINVKGVFMGMKYAASVMIPRKQGSIISLGSVGSVIGGIGPHHYISSKHAVVGLTR

SIAAELGQHGIRVNCVSPYAVPTNLAVAHLPEDERTEDMFTGFREFAKKNANLQGVELTV

EDVANAVLFLASEDARYISGDNLIVDGGFTRVNHSFRVFR

Citrus sinensis CsDH1
SEQ ID NO: 38
MSKPRLQGKVAIIMGAASGIGEATAKLFAEHGAFVIIADIQDELGNQVVSSIGPEKASYR

HCDVRDEKQVEETVAYAIEKYGSLDIMYSNAGVAGPVGTILDLDMAQFDRTIATNLAGSV

MAVKYAARVMVANKIRGSIICTTSTASTVGGSGPHAYTISKHGLLGLVRSAASELGKHGI

RVNCVSPFGVATPESAGTINDVEGFVCKVANLKGIVLKAKHVAEAALFLASDESAYVSGH

DLVVDGGFTAVTNVMSMLEGHG

Citrus sinensis CsDH2
SEQ ID NO: 39
MSNPRMEGKVALITGAASGIGEAAVRLFAEHGAFVVAADVQDELGHQVAASVGTDQVCYH

HCDVRDEKQVEETVRYTLEKYGKLDVLFSNAGIMGPLTGILELDLTGFGNTMATNVCGVA

ATIKHAARAMVDKNIRGSIICTTSVASSLGGTAPHAYTTSKHALVGLVRTACSELGAYGI

RVNCISPFGVATPLSCTAYNLRPDEVEANSCALANLKGIVLKAKHIAEAALFLASDESAY

ISGHNLAVDGGFTVVNHSSSSAT

Citrus sinensis CsDH3
SEQ ID NO: 40
MTTAGSRDSPLVAQRLLGKVALVTGGATGIGESIVRLFHKHGAKVCVVDINDDLGQHLCQ

TLGPTTRFIHGDVAIEDDVSRAVDFTVANFGTLDIMVNNAGMGGPPCPDIREFPISTFEK

VFDINTKGTFIGMKHAARVMIPSKKGSIVSISSVTSAIGGAGPHAYTASKHAVLGLTKSV

-continued

AAELGQHGIRVNCVSPYAILTNLALAHLHEDERTDDARAGFRAFIGKNANLQGVDLVEDD

VANAVLFLASDDARY1SGDNLFVDGGFTCTNHSLRVFR

*Rhodococcus erythropolis* ReCDH
SEQ ID NO: 41

MARVEGQVALITGAARGQGRSHAIKLAEEGADVILVDVPNDVVDIGYPLGTADELDQTAK

DVENLGRKAIVIHADVRDLESLTAEVDRAVSTLGRLDIVSANAGIASVPFLSHDIPDNTW

RQMIDINLTGVWHTAKVAVPHILAGERGGSIVLTSSAAGLKGYAQISHYSAAKHGVVGLM

RSLALELAPHRVRVNSLHPTQVNTPMIQNEGTYRIFSPDLENPTREDFEIASTTTNALPI

PWVESVDVSNALLFLVSEDARYITGAAIPVDAGTTLK

VoDH1
SEQ ID NO: 42

MSTASSGDVSLLSQRLVGKVALITGGATGIGESIARLFYRHGAKVCIVDIQDNPGQNLCR

ELGTDDACFFHCDVSIEIDVIRAVDFVVNRFGKLDIMVNNAGIADPPCPDIRNTDLSIFE

KVFDVNVKGTFQCMKHAARVMVPQKKGSIISLTSVASVIGGAGPHAYTGSKHAVLGLTKS

VAAELGLHGIRVNCVSPYAVPTGMPLAHLPESEKTEDAMMGMRAFVGRNANLQGIELTVD

DVANSVVFLASDEARYVSGLNLMLDGGFSCVNHSLRVFR

*Vitis vinifera* VvDH
SEQ ID NO: 43

MAATSIDNSPLPSQRLLGKVALVTGGATGIGESIVRLFLKQGAKVCIVDVQDDLGQKLCD

TLGGDPNVSFFHCDVTIEDDVCHAVDFTVTKFGTLDIMVNNAGMAGPPCSDIRNVEVSMF

EKVFDVNVKGVFLGMKHAARIMIPLKKGTIISLCSVSSAIAGVGPHAYTGSKCAVAGLTQ

SVAAEMGGHGIRVNCISPYAIATGLALAHLPEDERTEDAMAGFRAFVGKNANLQGVELTV

DDVAHAAVFLASDEARYISGLNLMLDGGFSCTNHSLRVFR

*Zingiber zerumbet* ZzSDR
SEQ ID NO: 44

MRLEGKVALVTGGASGIGESIARLFIEHGAKICIVDVQDELGQQVSQRLGGDPHACYFHC

DVTVEDDVRRAVDFTAEKYGTIDIMVNNAGITGDKVIDIRDADFNEFKKVFDINVNGVFL

GMKHAARIMIPKMKGSIVSLASVSSVIAGAGPHGYTGAKHAVVGLTKSVAAELGRHGIRV

NCVSPYAVPTRLSMPYLPESEMQEDALRGFLTFVRSNANLKGVDLMPNDVAEAVLYLATE

ESKYVSGLNLVIDGGFSIANHTLQVFE

What is claimed is:

1. A microbial host cell for producing rotundone, the microbial cell expressing a heterologous α-guaiene synthase enzyme (αGTPS) and a heterologous α-guaiene oxidase (αGOX) enzyme; wherein the αGOX enzyme comprises an amino acid sequence that is at least 80% identical to SEQ ID NO: 51 or SEQ ID NO: 52.

2. The microbial cell of claim 1, wherein the microbial host cell expresses a cytochrome P450 reductase enzyme.

3. The microbial cell of claim 2, wherein the cytochrome P450 reductase enzyme comprises an amino acid sequence that is at least 90% identical to SEQ ID NO: 53 or SEQ ID NO: 33.

4. The microbial cell of claim 1, wherein the αGTPS and αGOX are expressed together in an operon.

5. The microbial cell of claim 1, wherein the microbial host cell further expresses one or more alcohol dehydrogenases (ADHs).

6. The microbial cell of claim 5, wherein the ADH comprises an amino acid sequence of any one of SEQ ID NOs: 35-44, or an amino acid sequence that is at least 90% identical thereto.

7. The microbial cell of claim 5, wherein the ADH comprises an amino acid sequence having 90% or more sequence identity to SEQ ID NO: 43.

8. The microbial cell of claim 1, wherein the microbial host cell overexpresses one or more enzymes in a methylerythritol phosphate (MEP) or a mevalonic acid (MVA) pathway.

9. The microbial cell of claim 1, wherein the microbial cell is a bacteria, optionally selected from *Escherichia* spp., *Bacillus* spp., *Corynebacterium* spp., *Rhodobacter* spp., *Zymomonas* spp., *Vibrio* spp., and *Pseudomonas* spp.

10. The microbial cell of claim 9, wherein the microbial cell is *Escherichia coli*.

11. The microbial cell of claim 1, wherein the microbial host cell is a yeast, optionally selected from *Saccharomyces, Pichia,* or *Yarrowia*.

12. The microbial cell of claim 1, wherein the αGOX enzyme comprises an amino acid sequence that is at least 85% identical to SEQ ID NO: 51.

13. The microbial cell of claim 1, wherein the αGOX enzyme comprises an amino acid sequence that is at least 90% identical to SEQ ID NO: 51.

14. The microbial cell of claim 1, wherein the αGOX enzyme comprises an amino acid sequence that is at least 95% identical to SEQ ID NO: 51.

15. The microbial cell of claim 1, wherein the αGOX enzyme comprises an amino acid sequence that is at least 85% identical to SEQ ID NO: 52.

16. The microbial cell of claim 1, wherein the αGOX enzyme comprises an amino acid sequence that is at least 90% identical to SEQ ID NO: 52.

17. The microbial cell of claim 1, wherein the αGOX enzyme comprises an amino acid sequence that is at least 95% identical to SEQ ID NO: 52.

18. The microbial cell of claim 1, wherein αGTPS enzyme comprises an amino acid sequence that is at least 90% identical to an amino acid sequence selected from SEQ ID NOS: 1, 3, 4, 6-10, 11-15, and 19.

19. The microbial cell of claim 1, wherein αGTPS enzyme comprises an amino acid sequence that is at least 90% identical to the amino acid sequence of SEQ ID NO: 8.

20. A method for making rotundone, comprising: culturing the microbial cell of claim 1, and recovering the rotundone.

21. The method of claim 20, wherein the culturing is performed using a batch culture, continuous culture, or semi-continuous culture that has a volume of at least 100 L.

22. The method of claim 21, wherein the culture has a volume of at least 1000 L.

23. The method of claim 20, wherein the rotundone is recovered by partitioning into an organic phase, followed by fractional distillation.

24. The method of claim 20, wherein the culturing is a batch culture.

* * * * *

```
                    SEQUENCE LISTING

Sequence total quantity: 56
SEQ ID NO: 1           moltype = AA  length = 561
FEATURE                Location/Qualifiers
source                 1..561
                       mol_type = protein
                       organism = Vitis vinifera
SEQUENCE: 1
MSVPLSVSVT PILSQRIDPE VARHEATYHP NFWGDRFLHY NPDDDFCGTH ACKEQQIQEL   60
KEEVRKSLEA TAGNTSQLLK LIDSIQRLGL AYHFEREIEE ALKAMYQTYT LVDDNDHLTT  120
VSLLFRLLRQ EGYHIPSDVF KKFMDEGGNF KESLVGDLPG MLALYEAAHL MVHGEDILDE  180
ALGFTTAHLQ SMAIDSDNPL TKQVIRALKR PIRKGLPRVE ARHYITIYQE DDSHNESLLK  240
LAKLDYNMLQ SLHRKELSEI TKWWKGLDFA TKLPFARDRI VEGYFWILGV YFEPQYYLAR  300
RILMKVFGVL SIVDDIYDAY GTFEELKLFT EAIERWDASS IDQLPDYMKV CYQALLDVYE  360
EMEEEMTKQG KLYRVHYAQA ALKRQVQAYL LEAKWLKQEY IPTMEEYMSN ALVTSACSML  420
TTTSFVGMGD MVTKEAFDWV FSDPKMIRAS NVICRLMDDI VSHEFEQKRG HVASAVECYM  480
KQYGVSKEEA YDEFKKQVES AWKDNNEEVL QPTAVPVPLL TRVLNFSRMV DVLYKDEDEY  540
TLVGPLMKDL VAGMLIDPVP M                                            561

SEQ ID NO: 2           moltype = AA  length = 552
FEATURE                Location/Qualifiers
source                 1..552
                       mol_type = protein
                       organism = synthetic construct
```

-continued

```
SEQUENCE: 2
MELYAQSVGV GAASRPLANF HPCVWGDKFI VYNPQSCQAG EREEAEELKV ELKRELKEAS  60
DNYMRQLKMV DAIQRLGIDY LFVEDVDEAL KNLFEMFDAF CKNNHDMHAT ALSFRLLRQH  120
GYRVSCEVFE KFKDGKDGFK VPNEDGAVAV LEFFEATHLR VHGEDVLDNA FDFTRNYLES  180
VYATLNDPTA KQVHNALNEF SFRRGLPRVE ARKYISIYEQ YASHHKGLLK LAKLDFNLVQ  240
ALHRRELSED SRWWKTLQVP TKLSFVRDRL VESYFWASGS YFEPNYSVAR MILAKGLAVL  300
SLMDDVYDAY GTFEELQMFT DAIERWDASC LDKLPDYMKI VYKALLDVFE EVDEELIKLG  360
APYRAYYGKE AMKYAARAYM EEAQWREQKH KPTTKEYMKL ATKTCGYITL IILSCLGVEE  420
GIVTKEAFDW VFSRPPFIEA TLIIARLVND ITGHEFEKKR EHVRTAVECY MEEHKVGKQE  480
VVSEFYNQME SAWKDINEGF LRPVEFPIPL LYLILNSVRT LEVIYKEGDS YTHVGPAMQN  540
IIKQLYLHPV PY                                                     552

SEQ ID NO: 3            moltype = AA  length = 547
FEATURE                 Location/Qualifiers
source                  1..547
                        mol_type = protein
                        organism = Aquilaria crassna
SEQUENCE: 3
MSSAKLGSAS EDVNRRDANY HPTVWGDFFL THSSNFLENN DSILEKHEEL KQEVRNLLVV  60
ETSDLPSKIQ LTDEIIRLGV GYHFETEIKA QLEKLHDHQL HLNFDLLTTS VWFRLLRGHG  120
FSISSDVFKR FKNTKGEFET EDARTLWCLY EATHLRVDGE DILEEAIQFS RKKLEALLPE  180
LSFPLNECVR DALHIPYHRN VQRLAARQYI PQYDAEPTKI ESLSLFAKID FNMLQALHQR  240
ELREASRWWK EFDFPSKLPY ARDRIAEGYY WMMGAHFEPK FSLSRKFLNR IIGITSLIDD  300
TYDVYGTLEE VTLFTEAVER WDIEAVKDIP KYMQVIYTGM LGIFEDFKDN LINARGKDYC  360
IDYAIEVFKE IVRSYQREAE YFHTGYVPSY DEYMENSIIS GGYKMFIILM LIGRGEFELK  420
ETLDWASTIP EMVEASSLIA RYIDDLQTYK AEEERGETVS AVRCYMREFG VSEEQACKKM  480
REMIEIEWKR LNKTTLEADE ISSSVVIPSL NFTRVLEVMY DKGDGYSDSQ GVTKDRIAAL  540
LRHAIEI                                                           547

SEQ ID NO: 4            moltype = AA  length = 547
FEATURE                 Location/Qualifiers
source                  1..547
                        mol_type = protein
                        organism = Aquilaria crassna
SEQUENCE: 4
MSSAKLGSAS EDVSRRDANY HPTVWGDFFL THSSNFLENN DSILEKHEEL KQEVRNLLVV  60
ETSDLPSKIQ LTDEIIRLGV GYHFETEIKA QLEKLHDHQL HLNFDLLTTS VWFRLLRGHG  120
FSIPSDVFKR FKNTKGEFET EDARTLWCLY EATHLRVDGE DILEEAIQFS RKRLEALLPK  180
LSFPLSECVR DALHIPYHRN VQRLAARQYI PQYDAEQTKI ESLSLFAKID FNMLQALHQS  240
ELREASRWWK EFDFPSKLPY ARDRIAEGYY WMMGAHFEPK FSLSRKFLNR IVGITSLIDD  300
TYDVYGTLEE VTLFTEAVER WDIEAVKDIP KYMQVIYIGM LGIFEDFKDN LINARGKDYC  360
IDYAIEVFKE IVRSYQREAE YFHTGYVPSY DEYMENSIIS GGYKMFIILM LIGRGEFELK  420
ETLDWASTIP EMVKASSLIA RYIDDLQTYK AEEERGETVS AVRCYMREFG VSEEQACKKM  480
REMIEIEWKR LNKTTLEADE ISSSVVIPSL NFTRVLEVMY DKGDGYSDSQ GVTKDRIAAL  540
LRHAIEI                                                           547

SEQ ID NO: 5            moltype = AA  length = 547
FEATURE                 Location/Qualifiers
source                  1..547
                        mol_type = protein
                        organism = Aquilaria crassna
SEQUENCE: 5
MSSAKLGSAS EDVSRRDANY HPTVWGDFFL THSSDFLENN DSILEKHEEL KQEVRNLLVV  60
ETSDLPSKIQ LTDDIIRLGV GYHFETEIKA QLEKLHDHQL HLNFDLLTTS VWFRLLRGHG  120
FSISSDVFKR FKNTKGEFET EDARTLWCLY EATHLRVDGE DILEEAIQFS RKKLEALLPE  180
LSFPLNECVR DALHIPYHRN VQRLAARQYI PQYDAEPTKI ESLSLFAKID FNMLQALHQR  240
ELREASRWWK EFDFPSKLPY ARDRIAEGYY WMMGAHFEPK FSLSRKFLNR IIGITSLIDD  300
TYDVYGTLEE VTLFTEAVER WDIEAVKDIP KYMQVIYIGM LGIFEDFKDN LINARGKDYC  360
IDYAIEVFKE IVRSYQREAE YFHTGYVPSY DEYMENSIIS GGYKMFIILM LIGRGEFELK  420
ETLDWASTIP EMVKASSLIA RYIDDLQTYK AEEERGETVS AVRCYMREYD VSEEEACKKM  480
REMIEIEWKR LNKTTLEADE VSSSVVIPSL NFTRVLEVMY DKGDGYSDSQ GVTKDRIAAL  540
LRHAIEI                                                           547

SEQ ID NO: 6            moltype = AA  length = 547
FEATURE                 Location/Qualifiers
source                  1..547
                        mol_type = protein
                        organism = Aquilaria crassna
SEQUENCE: 6
MSSAKLGSAS EDVSRRDANY HPTVWGDFFL THSSNFLENN DSILEKHEEL KQEVRNLLVV  60
ETSDLPSKIQ LTDEIIRLGV GYHFETEIKA QLEKLHDHQL HLNFDLLTTS VWFRLLRGHG  120
FSISSDVFKR FKNTKGEFET EDAWTLWCLY EATHLRVDGE DILEEAIQFS RKKLEALLPE  180
LSFPLNECVR DALHIPYHRN VQRLAARQYI PQYDAEPTKI ESLSLFAKID FNMLQALHQS  240
ELREASRWWK EFDFPSKLPY ARDRIAEGYY WMMGAHFEPK FSLSRKFLNR IIGITSLIDD  300
TYDVYGTLEE VTLFTEAVER WDIEAVKDIP KYMQVIYTGM LGIFEDFKDN LINARGKDYC  360
IDYAIEVFKE IVRSYQREAE YFHTGYVPSY DEYMENSIIS GGYKMFIILM LIGRGEFELK  420
ETLDWASTIP EMVKASSLIA RYIDDLQTYK AEEERGETVS AVRCYMREFG VSEEQACKKM  480
REMIEIEWKR LNKTTLEADE ISSSVVIPSL NFTRVLEVMY DKGDGYSDSQ GVTKDRIAAL  540
LRHAIEI                                                           547
```

```
SEQ ID NO: 7              moltype = AA  length = 547
FEATURE                   Location/Qualifiers
source                    1..547
                          mol_type = protein
                          organism = Aquilaria crassna
SEQUENCE: 7
MSSAKLGSAS EDVSRRDANY HPTVWGDFFL THSSNFLENN DSILEKHEEL KQEVRNLLVV   60
ETSDLPSKIQ LTDEIIRLGV GYHFETEIKA QLEKLHDHQL HLNFDLLTTS VWFRLLRGHG  120
FSISSDVFKR FKNTKGEFET EDARTLWCLY EATHLRVDGE DILEEAIQFS RKKLEALLPE  180
LSFPLNECVR DALHIPYHRN VQRLAARQYI PQYDAEPTKI ESLSLFAKID FNMLQALHQS  240
ELREASRWWK EFDFPSKLPY ARDRIAEGYY WMMGAHFEPK FSLSRKFLNR IIGITSLIDD  300
TYDVYGTLEE VTLFTEAVER WDIEAVKDIP KYMQVIYTGM LGIFEDFKDN LINARGKDYC  360
IDYAIEVFKE IVRSYQREAE YFHTGYVPSY DEYMENSIIS GGYKMFIILM LIGRGEFELK  420
ETLDWASTIP EMVKASSLIA RYIDDLQTYK AEEERGETVS AVRCYMREFG VSEEQACKKM  480
REMIEIEWKR LNKTTLEADE ISSSVVIPSL NFTRVLEVMY DKGDGYSDSQ GVTKDRIAAL  540
LRHAIEI                                                           547

SEQ ID NO: 8              moltype = AA  length = 547
FEATURE                   Location/Qualifiers
source                    1..547
                          mol_type = protein
                          organism = Aquilaria crassna
SEQUENCE: 8
MSSAKLGSAS EDVSRRDANY HPTVWGDFFL THSSNFLENN DSILEKHEEL KQEVRNLLVV   60
ETSDLPSKIQ LTDEIIRLGV GYHFETEIKA QLEKLHDHQL HLNFDLLTTS VWFRLLRGHG  120
FSISSDVFKR FKNTKGEFET EDARTLWCLY EATHLRVDGE DILEEAIQFS RKKLEALLPE  180
LSFPLNECVR DALHIPYHRN VQRLAARQYI PQYDAEPTKI ESLSLFAKID FNMLQALHQR  240
ELREASRWWK EFDFPSKLPY ARDRIAEGYY WMMGAHFEPK FSLSRKFLNR IIGITSLIDD  300
TYDVYGTLEE VTLFTEAVER WDIEAVKDIP KYMQVIYTGM LGIFEDFKDN LINARGKDYC  360
IDYAIEVFKE IVRSYQREAE YFHTGYVPSY DEYMENSIIS GGYKMFIILM LIGRGEFELK  420
ETLDWASTIP EMVKASSLIA RYIDDLQTYK AEEERGETVS AVRCYMREFG VSEEQACKKM  480
REMIEIEWKR LNKTTLEADE ISSSVVIPSL NFTRVLEVMY DKGDGYSDSQ GVTKDRIAAL  540
LRHAIEI                                                           547

SEQ ID NO: 9              moltype = AA  length = 547
FEATURE                   Location/Qualifiers
source                    1..547
                          mol_type = protein
                          organism = Aquilaria crassna
SEQUENCE: 9
MSSAKLGSAS EDVSRRDANY HPTVWGDFFL THSSNFLENN DNILEKHEEL KQEVRNLLVV   60
ETSDLPSKIQ LTDEIIRLGV GYHFEMEIKA QLEKLHDHQL HLNFDLLTTS VWFRLLRGHG  120
FSISSDVFKR FKNTKGEFET EDARTLWCLY EATHLRVDGE DILEEAIQFS RKRLEALLPK  180
LSFPLSECVR DALHIPYHRN VQRLAARQYI PQYDAEQTKI ESLSLFAKID FNMLQALHQS  240
ELREASRWWK EFDFPSKLPY ARDRIAEGYY WMMGAHFEPK FSLSRKFLNR IIGITSLIDD  300
TYDVYGTLEE VTLFTEAVER WDIEAVKDIP KYMQVIYIGM LGIFEDFKDN LINARGKDYC  360
IDYAIEVFKE IVRSYQREAE YFHTGYVPSY DEYMENSIIS GGYKMFIILM LIGRGEFELK  420
ETLDWASTIP EMVKASSLIA RYIDDLQTYK AEEERGETVS AVRCYMREYD VSEEEACKKM  480
REMIEIEWKR LNKTTLEADE VSSSVVIPSL NFTRVLEVMY DKGDGYSDSQ GVTKDRIAAL  540
LRHAIEI                                                           547

SEQ ID NO: 10             moltype = AA  length = 547
FEATURE                   Location/Qualifiers
source                    1..547
                          mol_type = protein
                          organism = Aquilaria crassna
SEQUENCE: 10
MSSAKLGSAS EDVSRRDANY HPTVWGDFFL THSSNFLENN DSILEKHEEL KQEVRNLLVV   60
ETIDLPSKIQ LTDEIIRLGV GYHFEMEIKA QLEKLHDHQL HLNFDLLTTS VWFRLLRGHG  120
FSISSDVFKR FKNTKGEFET EDARTLWCLY EATHLRVDGE DILEEAIQFS RKKLEALLPE  180
LSFPLNECVR DALHIPYHLN VQRLAARQYI PQYDAEPTKI ESLSLFAKID FNMLQALHQS  240
ELREASRWWK EFDFPSKLPY ARDRIAEGYY WMMGAHFEPK FSLSRKFLNR IIGITSLIDD  300
TYDVYGTLEE VTLFTEAVER WDIEAVKDIP KYMQVIYTGM LGIFEDFKDN LINARGKDYC  360
IDYAIEVFKE IVRSYQREAE YFHTGYVPSY DEYMENSIIS GGYKMFIILM LIGRGEFELK  420
ETLDWASTIP EMVKASSLIA RYIDDLQTYK AEEERGETVS AVRCYMREYG VSEEEACKKM  480
REMIEIEWKR LNKTTLEADE ISSSVVIPSL NFTRVLEVMY DKGDGYSDSQ GVTKDRIAAL  540
LRHAIEI                                                           547

SEQ ID NO: 11             moltype = AA  length = 547
FEATURE                   Location/Qualifiers
source                    1..547
                          mol_type = protein
                          organism = Aquilaria crassna
SEQUENCE: 11
MSSAKLGSAS EDVSRRDANY HPTVWGDFFL THSSNFLENN DNILEKHEEL KQEVRNLLVV   60
ETSDLPSKIQ LTDEIIRLGV GYHFEMEIKA QLEKLHDHQL HLNFDLLTTS VWFRLLRGHG  120
FSISSDVFKR FKNTKGEFET EDARTLWCLY EATHLRVDGE DILEEAIQFS RKRLEALLPK  180
LSFPLSECVR DALHIPYHRN VQRLAARQYI PQYDAEQTKI ESLSLFAKID FNMLQALHQS  240
```

```
ELREASRWWK EFDFPSKLPY ARDRIAEGYY WMMGAHFEPK FSLSRKFLNR IIGITSLIDD    300
TYDVYGTLEE VTLFTEAVER WDIEAVKDIP KYMQVIYIGM LGIFEDFKDN LINARGKDYC    360
IDYAIEVFKE IVRSYQREAE YFHTGYVPSY DEYMENSIIS GGYKMFIILM LIGRGEFELK    420
QTLDWASTIP EMVKASSLIA RYIDDLQTYK AEEERGETVS AVRCYMREYD VSEEEACKKM    480
REMIEIEWKR LNKTTLEADE VSSSVVIPSL NFTRVLEVMY DKGDGYSDSQ GVTKDRIAAL    540
LRHAIEI                                                             547

SEQ ID NO: 12         moltype = AA  length = 547
FEATURE               Location/Qualifiers
source                1..547
                      mol_type = protein
                      organism = unidentified
SEQUENCE: 12
MSSAKLGSAS EDVSRRDANY HPTVWGDFFL THSSNFLENN DNILEKHEEL KQEVRNLLVV    60
ETSDLPSKIQ LTDKIIRLGV GYHFEMEIKA QLEKLHDHQL HLNFDLLTTS VWFRLLRGHG    120
FSISSDVFKR FKNTKGEFET EDARTLWCLY EATHLRVDGE DILEEAIQFS RKKLEALLPE    180
LSFPLNECVR DALHIPYHRN VQRLAARQYI PQYDAELTKI ESLSLFAKID FNMLQALHQS    240
ELREASRWWK EFDFPSKLPY ARDRIAEGYY WMMGAHFEPK FSLSRKFLNR IIGITSLIDD    300
TYDVYGTLEE VTLFTKAVER WDIEAVQDIP KYMQVIYTGM LGIFEDFKDN LINARGKDYC    360
IDYAIEVFKE IVRSYQREAE YFHTGYVPSY DEYMENSIIS GGYKMFIILM LIGRGEFELK    420
ETLDWASTIP EMVKASSLIA RYIDDLQTYK AEEKRGETVS AVRCYMREYG VSEEEACKKM    480
REMIEIEWKK LNKTTLEANE ISSSVVIPSL NFTRVLEVMY DKGDGYSDSQ GVTKDRIAAL    540
LRHAIEI                                                             547

SEQ ID NO: 13         moltype = AA  length = 547
FEATURE               Location/Qualifiers
source                1..547
                      mol_type = protein
                      organism = unidentified
SEQUENCE: 13
MSSAKLGSAS EDVSRRDANY HPTVWGDFFL THSSNFLENN DNILEKHEEL KQEVTNLLVV    60
ETSDLPSKIQ LTDEIIRLGV GYHFEMEIKA QLEKLHDHQL HLNFDLLTTS VWFRLLRGHG    120
FSISSDVFKR FKNTKGEFET EDARTLWCLY EATHLRVDGE DILEEAIQFS RKKLEALLPE    180
LSFPLNECVR DALHIPYHRN VQRLAARQYI PQYDAELTKI ESLSLFAKID FNMLQALHQS    240
ELREASRWWK EFDFPSKLPY ARDRIAEGYY WMMGAHFEPK FSLSRKFLNR IIGITSLIDD    300
TYDVYGTLEE VTLFTEAVER WDIEAVKDIP KYMQVIYTGM LGIFEDFKDN LINARGKDYC    360
IDYAIEVFKE IVRSYQREAE YFHTGYVPSY DEYMENSIIS GGYKMFIILM LIGRAEFELK    420
ETLDWASTIP EMVKASSLIA RYIDDLQTYK AEEERGETVS AVRCYMREYG VSEEEACKKM    480
REMIEIEWKR LNKTTLEADE ISSSVVIPSL NFTRVLEVMY DKGDGYSDSQ GVTKGRIAAL    540
LRHAIEI                                                             547

SEQ ID NO: 14         moltype = AA  length = 547
FEATURE               Location/Qualifiers
source                1..547
                      mol_type = protein
                      organism = Aquilaria spp.
SEQUENCE: 14
MSSAKLGSAS EDVSRRDANY HPTVWGDFFL THSSNFLENN HSILEKHEEL KQEVRNLLVV    60
ETSDLPSKIQ LTDKIIRLGV GYHFEMEIKA QLEKLHDHQL HLNFDLLTTS VWFRLLRGHG    120
FSISSDVFKR FKNTKGEFET EDARTLWCLY EATHLRVDGE DILEEAIQFS RKKLEALLPE    180
LSFPLNECVR DALHIPYHRN VQRLAARQYI PQYDAELTKI ESLSLFAKID FNMLQALHQS    240
ELREASRWWK EFDFPSKLPY ARDRIAEGYY WMMGAHFEPK FSLSRKFLNR IIGITSLIDD    300
TYDVYGTLEE VTLFTEAVER WDIEAVKDIP KYMQVIYTGM LGIFEDFKDN LINARGKDYC    360
IDYAIEVFKE IVRSYQREAE YFHTGYVPSY DEYMENSIIS GGYKMFIILM LIGRAEFELK    420
ETLDWASTIP EMVKASSLIA RYIDDLQTYK AEEERGETVS AVRCYMREYG VSEEEACKKM    480
REMIEIEWKR LNKTTLEADE ISSSVVIPSL NFTRVLEVMY DKGDGYSDSQ GVTKDRIAAL    540
LRHAIEI                                                             547

SEQ ID NO: 15         moltype = AA  length = 547
FEATURE               Location/Qualifiers
source                1..547
                      mol_type = protein
                      organism = Aquilaria spp.
SEQUENCE: 15
MSSAKLGSAP EDVSRRDANY HPTVWGDFFL THSSNFLENN HSILEKHEEL KQEVRNLLVV    60
ETSDLPSKIQ LTDKIIRLGV GYHFEMEIKA QLEKLQDHQL HLNFDLLTTS VWFRLLRGHG    120
FSISSDVFKR FKNTKGEFET EDARTLWCLY EATHLRVDGE DILEEAIQFS RKKLEALLPE    180
LSFPLNECVR DALHIPYHRN VQRLAARQYI PQYDAELTKI ESLSLFAKID FNMLQALHQS    240
ELREASRWWK EFDFPSKLPY ARDRIAEGYY WMMGAHFEPK FSLSRKFLNR IIGITSLIDD    300
TYDVYGTLEE VTLFTEAVER WDIEAVKDIP KYMQVIYTGM LGIFEDFKDN LINARGKDYC    360
IDYAIEVFKE IVRSYQREAE YFHTGYVPSY DEYMENSIIS GGYKMFIILM LIGRAEFELK    420
ETLDWASTIP EMVKASSLIA RYIDDLQTYK AEEERGETVS AVRCYMREYG VSEEEACKKM    480
REMIEIEWKR LNKTTLEADE ISSSVVIPSL NFTRVLEVMY DKGDGYSDSQ GVTKDRIATL    540
LRHAIEI                                                             547

SEQ ID NO: 16         moltype = AA  length = 538
FEATURE               Location/Qualifiers
source                1..538
                      mol_type = protein
```

```
                        organism = Aquilaria spp.
SEQUENCE: 16
MSSAKLGSAS EDVSRRDADY HPTVWGDFFL THSSNFLENN HSILEKHEEL KQEVRNLLVV  60
ETSDLPSKIQ LTDKIIRLGV GYHFEMEIKA QLEKLHDHQL HLNFDLLTTS VWFRLLRGHG 120
FSISSDVFKR FKNTKGEFET EDARTSWCLY EATHLRVDGE DILEEAIQFS RKKLEALLPE 180
LSFPLNECVR DALHIPYHRN VQRLAARQYI SQYDAELTKI ESLSLFAKID FNMLQALHQS 240
ELREASRWWK EFDFPSKLPY ARDRIAEGYY WMMGAHFEPK FSLSRKFLNR IIGITSLIDD 300
TYDVYGTLEE VTLFTEAVER WDIEAVKDIP KYMQVIYTGM LGIFEDFKDN LINARGKDYC 360
IDYAIEVFKE IVRSYQREAE YFHTGYVPSY DEYMENSIIS GGYKMFIILM LIGRAEFELK 420
ETLDWASTIP EMVKASSLIA RYIDDLQTYK AEEEERGETVS AVRCYMREYG VSEEEACKKM 480
REMIEIEWKR LNKTTLEADE ISSSVVIPSL NFTRVLEVMY DKGDGYSDSQ GVTKDRIA   538

SEQ ID NO: 17          moltype = AA  length = 547
FEATURE                Location/Qualifiers
source                 1..547
                       mol_type = protein
                       organism = Aquilaria spp.
SEQUENCE: 17
MSSAKLGSTS EDVSRRDANY HPTVWGDFFL THSSNFLENN DSILEKHEEL KQEVRNLLVV  60
ETSDLPSKIQ LTDEIIRLGV GYHFETEIKA QLEKLHDHQL HLNFDLLTTS VWFRLLRGHG 120
FSISSDVFKR FKNTKGEFKT EDARTLWCLY EATHLRVDGE DVLEEAIQFS RKKLEALLPE 180
LSFPLSECVR DALHIPYHRN VQRLAARQYI PQYDAEPTKI ESLSLFAKID FNMLQALHQS 240
ELREASRWWK EFDFPSKLPY ARDSIAEGYY WMMGAHFEPK FSLSRKFLNR IIGITSLIDD 300
TYDVYGTLEE VTLFTEAVER WDIEAVKDIP KYMQVIYTGM LGIFEDFKDN LINARGKDYC 360
IDYAIEVFKE IVRSYQREAE YFHTGYVPSY DEYMENSIIS GGYKMFIILM LIGRGEFELK 420
ETLDWASTIP EMVKASSLIA RYIDDLQTYK AEEKRGETVS AVRCYMREYG VSEEEACKKM 480
KEMIEIEWKR LNKTTLEADE ISSSVVIPSL NFTRVLEVMY DKGDGYSDSQ GVTKDRIAAL 540
LRHAIEI                                                           547

SEQ ID NO: 18          moltype = AA  length = 547
FEATURE                Location/Qualifiers
source                 1..547
                       mol_type = protein
                       organism = Aquilaria spp.
SEQUENCE: 18
MSSAKLGSAS EDVSRRDANY HPTVWGDFFL THSSNFLENN DSILEKHEEL KQEVRNLLVV  60
ETSDLPSKIQ LTDEIIRLGV GYHFETEIKA QLEKLHDHQL HLNFDLLTTS VWFRLLRGHG 120
FSISSDVFKR FKNTKGEFKT EDARTLWCLY EATHLRVDGE DVLEEAIQFS RKKLEALLPE 180
LSFPLSECVR DALHIPYHRN VQRLAARQYI PQYDAEPTKI ESLSLFAKID FNMLQALHQS 240
ELREASRWWK EFDFPSKLPY ARDRIAEGYY WMMGAHFEPK FSLSRKFLNR IIGITSLIDD 300
TYDVYGTLEE VTLFTEAVER WDIEAVKDIP KYMQVIYTGM LGIFEDFKDN LINARGKDYC 360
IDYAIEVFKE IVRSYQREAE YFHTGYVPSY DEYMENSIIS GGYKMFIILM LIGRGEFELK 420
ETLDWASTIP EMVKASSLIA RYIDDLQTYK AEEKRGETVS AVRCYMREYG VSEEEACKKM 480
KEMIEIEWKR LNKTTLEADE ISSSVVIPSL NFTRVLEVMY DKGDGYSDSQ GVTKDRIAAL 540
LRHAIEI                                                           547

SEQ ID NO: 19          moltype = AA  length = 547
FEATURE                Location/Qualifiers
source                 1..547
                       mol_type = protein
                       organism = Aquilaria spp.
SEQUENCE: 19
MSSAKLGSAS EDVSRRDANY HPTVWGDFFL THSSNFLENN DSILEKHEEL KQEVRNLLVV  60
ETSDLPSKIQ LTDEIIRLGV GYHFETEIKA QLEKLHDHQL HLNFDLLTTS VWFRLLRGHG 120
FSISSDVFKR FKNTKGEFKT EDARTLWCLY EATHLRVDGE DVLEEAIQFS RKKLEALLPE 180
LSFPLSECVR DALHIPYHRN VQRLAARQYI PQYDAEPTKI ESLSLFAKID FNMLQALHQS 240
ELREASRWWK EFDFPSKLPY ARDRIAEGYY WMMGAHFEPK FSLSRKFLNR IIGITSLIDD 300
TYDVYGTLEE VTLFTEAVER WDIEAVKDIP KYMQVIYTGM LGIFEDFKDN LINARGKDYC 360
IDYAIEVFKE IVRSYQREAE YFHTGYVPSY DEYMENSIIS GGYKMFIILM LIGRGEFELK 420
ETLDWASTIP EMVKASSLIA RYIDDLQTYK AEEERGETVS AVRCYMREYG VSEEEACKKM 480
REMIEIEWKR LNKTTLEADE ISSSVVIPSL NFTRVLEVMY DKGDGYSDSQ GVTKDRIAAL 540
LRHAIEI                                                           547

SEQ ID NO: 20          moltype = AA  length = 547
FEATURE                Location/Qualifiers
source                 1..547
                       mol_type = protein
                       organism = Aquilaria spp.
SEQUENCE: 20
MSSAKLGSAS EDVSRRDANY HPTVWGDFFL THSSNFLENN DNILEKHEEL KQEVRNLLVV  60
ETSDLPSKIQ LTDKIIRLGV GYHFEMEIKA QLEKLHDHQL HLNFDLLTTS VWFRLLRGHG 120
FSISSDVFKR FKNTKGEFET EDARTLWCLY EATHLRVDGE DILEEAIQFS RKRLEALLPK 180
LSFPLSECVR DALHIPYHRN VQRLAARQYI PQYDAEQTKI ESLSLFAKID FNMLQALRQS 240
ELREASRWWK EFDFPSKLPY ARDRIAEGYY WMMGAHFEPK FSLSRKFLNR IIGITSLIDD 300
TYDVYGTLEE VTLFTEAVER WDIEAVKDIP KYMQVIYTGM LGIFEDFKDN LINARGKDYC 360
IDYAIEVFKE IVRSYQREAE YFHTGYVPSY DEYMENSIIS GGYKMFIILM LIGRGEFELK 420
ETLDWASTIP EMVKASSLIA RYIDDLQTYK AEEERGETVS AVRCYMREFG VSEEQACKKM 480
REMIEIEWKR LNKTTLEADE ISSSVVIPSL NFTRVLEVMY DKGDGYSDSQ GVTKDRIAAL 540
LRHAIEI                                                           547
```

```
SEQ ID NO: 21            moltype = AA  length = 561
FEATURE                  Location/Qualifiers
source                   1..561
                         mol_type = protein
                         organism = Vitis vinifera
SEQUENCE: 21
MSVPLSVSVT PILSQRIDPE VARHEATYHP NFWGDRFLHY NPDDDFCGTH ACKEQQIQEL    60
KEEVRKSLEA TAGNTSQLLK LIDSIQRLGL AYHFEREIEE ALKAMYQTYT LVDDNDHLTT   120
VSLLFRLLRQ EGYHIPSDVF KKFMDEGGNF KESLVGDLPG MLALYEAAHL MVHGEDILDE   180
ALGFTTAHLQ SMAIDSDNPL TKQVIRALKR PIRKGLPRVE ARHYITIYQE DDSHNESLLK   240
LAKLDYNMLQ SLHRKELSEI TKWWKGLDFA TKLPFARDRI VEGYFWILGV YFEPQYYLAR   300
RILMKVFGVL SIVDDIYDAY GTFEELKLFT EAIERWDASS IDQLPDYMKV CYQALLDVYE   360
EMEEEMTKQG KLYRVHYAQA ALKRQVQAYL LEAKWLKQEY IPRMDEYMSN ALVSSACSML   420
TTTSFVGMGD IVTKEAFDWV FSDPKMIRAS NVICRLMDDI VSHEFEQKRG HVASAVECYM   480
KQYGVSKEEA YDEFKKQVES AWKDNNEEFL QPTAVPVPLL TRVLNFSRMM DVLYKDEDEY   540
TLVGPLMKDL VAGMLIDPVP M                                            561

SEQ ID NO: 22            moltype = AA  length = 508
FEATURE                  Location/Qualifiers
source                   1..508
                         mol_type = protein
                         organism = Vitis vinifera
SEQUENCE: 22
MELQFSFFPI LCTFLLFIYL LKRLGKPSRT NHPAPKLPPG PWKLPIIGNM HQLVGSLPHR    60
SLRSLAKKHG PLMHLQLGEV SAIVVSSREM AKEVMKTHDI IFSQRPCILA ASIVSYDCTD   120
IAFAPYGGYW RQIRKISVLE LLSAKRVQSF RSVREEEVLN LVRSVSLQEG VLINLTKSIF   180
SLTFSIISRT AFGKKCKDQE AFSVTLDKFA DSAGGFTIAD VFPSIKLLHV VSGMRRKLEK   240
VHKKLDRILG NIINEHKARS AAKETCEAEV DDDLVDVLLK VQKQGDLEFP LTMDNIKAVL   300
LDLFVAGTET SSTAVEWAMA EMLKNPRVMA KAQAEVRDIF SRKGNADETV VRELKFLKLV   360
IKETLRLHPP VPLLIPRESR ERCAINGYEI PVKTRVIINA WAIARDPKYW TDAESFNPER   420
FLDSSIDYQG TNFEYIPFGA GRRMCPGILF GMANVELALA QLLYHFDWKL PNGARHEELD   480
MTEGFRTSTK RKQDLYLIPI TYRPLPVE                                     508

SEQ ID NO: 23            moltype = AA  length = 417
FEATURE                  Location/Qualifiers
source                   1..417
                         mol_type = protein
                         organism = Bacillus subtilis
SEQUENCE: 23
MNEQIPHDKS LDNSLTLLKE GYLFIKNRTE RYNSDLFQAR LLGKNFICMT GAEAAKVFYD    60
TDRFQRQNAL PKRVQKSLFG VNAIQGMDGS AHIHRKMLFL SLMTPPHQKR LAELMTEEWK   120
AAVTRWEKAD EVVLFEEAKE ILCRVACYWA GVPLKETEVK ERADDFIDMV DAFGAVGPRH   180
WKGRRARPRA EEWIEVMIED ARAGLLKTTS GTALHEMAFH TQEDGSQLDS RMAAIELINV   240
LRPIVAISYF LVFSALALHE HPKYKEWLRS GNSREREMFV QEVRRYYPFG PFLGALVKKD   300
FVWNNCEFKK GTSVLLDLYG TNHDPRLWDH PDEFRPERFA EREENLFDMI PQGGGHAEKG   360
HRCPGEGITI EVMKASLDFL VHQIEYDVPE QSLHYSLARM PSLPESGFVM SGIRRKS     417

SEQ ID NO: 24            moltype = AA  length = 407
FEATURE                  Location/Qualifiers
source                   1..407
                         mol_type = protein
                         organism = Bacillus subtilis
SEQUENCE: 24
MQMEKLMFHP HGKEFHHNPF SVLGRFREEE PIHRFELKRF GATYPAWLIT RYDDCMAFLK    60
DNRITRDVKN VMNQEQIKML NVSEDIDFVS DHMLAKDTPD HTRLRSLVHQ AFTPRTIENL   120
RGSIEQIAEQ LLDEMEKENK ADIMKSFASP LPFIVISELM GIPKEDRSQF QIWTNAMVDT   180
SEGNRELTNQ ALREFKDYIA KLIHDRRIKP KDDLISKLVH AEENGSKLSE KELYSMLFLL   240
VVAGLETTVN LLGSGTLALL QHKKECEKLK QQPEMIATAV EELLRYTSPV VMMANRWAIE   300
DFTYKGHSIK RGDMIFIGIG SANRDPNFFE NPEILNINRS PNRHISFGFG IHFCLGAPLA   360
RLEGHIAFKA LLKRFPDIEL AVAPDDIQWR KNVFLRGLES LPVSLSK                407

SEQ ID NO: 25            moltype = AA  length = 404
FEATURE                  Location/Qualifiers
source                   1..404
                         mol_type = protein
                         organism = Bacillus cereus
SEQUENCE: 25
MASPENVILV HEISKLKTKE ELWNPYEWYQ FMRDNHPVHY DEEQDVWNVF LYEDVNRVLS    60
DYRLFSSRRE RRQFSIPPLE TRININSTDP PEHRNVRSIV SKAFTPRSLE QWKPRIQAIA   120
NELVQHIGKY SEVNIVEEFA APLPVTVISD LLGVPTTDRK KIKAWSDILF MPYSKEKFND   180
LDVEKGIALN EFKAYLLPIV QEKRYHLTDD IISDLIRAEY EGERLTDEEI VTFSLGLLAA   240
GNETTTNLII NSFYCFLVDS PGTYKELREE PTLISKAIEE VLRYRFPITL ARRITEDNI   300
FGPLMKKDQM VVAWVSAANL DEKKFSQASK FNIHRIGNEK HLTFGKGPHF CLGAPLARLE   360
AEIALTTDFIN AFEKIALSPS FNLEQCILEN EQTLKFLPIC LKTQ                  404

SEQ ID NO: 26            moltype = AA  length = 410
FEATURE                  Location/Qualifiers
source                   1..410
```

```
                        mol_type =  protein
                        organism =  Bacillus cereus
SEQUENCE: 26
MKKLTFNDLN  SPETMRNPIM  FYKNLMEQKE  RFFHIDDFYG  MGGAWVVFHY  DDVVAILKDS   60
RFIKDLRKFT  PPHYKQNPIE  ENTAVSKLFE  WLMNMPNMLT  VDPPDHTRLR  RLVSKSFTPR  120
MIEDLRPRIQ  QIADELLDVV  QEQRKMEIIA  DFAYPLPIIV  ISEMLGIPAT  DRNQFRAWTQ  180
ELMKASVDPG  QGTTVTATLE  KFINYIEILF  NEKHLNPSDD  LISALVQAKE  QEDKLSKNEL  240
LSTIWLLIIA  GHETTVNLIS  NGVLALLQHP  EQMNLLRQDP  SLLASAVDEL  LRYAGPIMFS  300
SRFASEDVTI  HGNRIRKGEL  VLLSLTAANI  DPNIFPYPEE  LNISREENNH  LAFGAGIHQC  360
LGAPLARLEG  QIALDTLLKR  LPNLRLAIEA  DQLIYNHSKI  RSLASLPVIF               410

SEQ ID NO: 27           moltype = AA   length = 711
FEATURE                 Location/Qualifiers
source                  1..711
                        mol_type =  protein
                        organism =  Stevia rebaudiana
SEQUENCE: 27
MAQSDSVKVS  PFDLVSAAMN  GKAMEKLNAS  ESEDPTTLPA  LKMLVENREL  LTLFTTSFAV   60
LIGCLVFLMW  RRSSSKKLVQ  DPVPQVIVVK  KKEKESEVDD  GKKKVSIFYG  TQTGTAEGFA  120
KALVEEAKVR  YEKTSFKVID  LDDYAADDDE  YEELKKESL   AFFFLATYGD  GEPTDNAANF  180
YKWFTEGDDK  GEWLKKLQYG  VFGLGNRQYE  HFNKIAIVVD  DKLTEMGAKR  LVPVGLGDDD  240
QCIEDDPFTAW KELVWPELDQ  LLRDEDDTSV  TTPYTAAVLE  YRVVHDKPA   DSYAEDQTHT  300
NGHVVHDAQH  PSRSNVAFKK  ELHTSQSDRS  CTHLEFDISH  TGLSYETGDH  VGVYSENLSE  360
VVDEALKLLG  LSPDTYFSVH  ADKEDGTPIG  GASLPPPFPP  CTLRDALTRY  ADVLSSPKKV  420
ALLALAAHAS  DPSEADRLKF  LASPAGKDEY  AQWIVANQRS  LLEVMQSFPS  AKPPLGVFFA  480
AVAPRLQPRY  YSISSSPKMS  PNRIHVTCAL  VYETTPAGRI  HRGLCSTWMK  NAVPLTESPD  540
CSQASIFVRT  SNFRLPVDPK  VPVIMIGPGT  GLAPFRGFLQ  ERLALKESGT  ELGSSIFFFG  600
CRNRKVDFIY  EDELNNFVET  GALSELIVAF  SREGTAKEYV  QHKMSQKASD  IWKLLSEGAY  660
LYVCGDAKGM  AKDVHRTLHT  IVQEQGSLDS  SKAELYVKNL  QMSGRYLRDV  W           711

SEQ ID NO: 28           moltype = AA   length = 693
FEATURE                 Location/Qualifiers
source                  1..693
                        mol_type =  protein
                        organism =  Arabidopsis thaliana
SEQUENCE: 28
MATSALYASD  LFKQLKSIMG  TDSLSDDVVL  VIATTSLALV  AGFVVLLWKK  TTADRSGELK   60
PLMIPKSLMA  KDEDDDLDLG  SGKTRVSIFF  GTQTGTAEGF  AKALSEEIKA  RYEKAAVKVI  120
DLDDYAADDD  QYEELKKKET  LAFFCVATYG  DGEPTDNAAR  FYKWFTEENE  RDIKLQQLAY  180
GVFALGNRQY  EHFNKIGIVL  DEELCKKGAK  RLIEVGLGDD  DQSIEDDFNA  WKESLWSELD  240
KLLKDEDDKS  VATPYTAVIP  EYRVVTHDPR  FTTQKSMESN  VANGNTTIDI  HHPCRVDVAV  300
QKELHTHESD  RSCIHLEFDI  SRTGITYETG  DHVGVYAENH  VEIVEEAGKL  LGHSLDLVFS  360
IHADKEDGSP  LESAVPPPFP  GPCTLGTGLA  RYADLLNPRK  KSALVALAAY  ATEPSEAEKL  420
KHLTSPDGKD  EYSQWIVASQ  RSLLEVMAAF  PSAKPPLGVF  FAAIAPRLQP  RYYSISSSPR  480
LAPSRVHVTS  ALVYGPTPTG  RIHKGVCSTW  MKNAVPAEKS  HECSGAPIFI  RASNFKLPSN  540
PSTPIVMVGP  GTGLAPFRGF  LQERMALKED  GEELGSSLLF  FGCRNRQMDF  IYEDELNNFV  600
DQGVISELIM  AFSREGAQKE  YVQHKMMEKA  AQVWDLIKEE  GYLYVCGDAK  GMARDVHRTL  660
HTIVQEQEGV  SSSEAEAIVK  KLQTEGRYLR  DVW                                 693

SEQ ID NO: 29           moltype = AA   length = 712
FEATURE                 Location/Qualifiers
source                  1..712
                        mol_type =  protein
                        organism =  Arabidopsis thaliana
SEQUENCE: 29
MASSSSSSST  SMIDLMAAII  KGEPVIVSDP  ANASAYESVA  AELSSMLIEN  RQFAMIVTTS   60
IAVLIGCIVM  LVWRRSGSGN  SKRVEPLKPL  VIKPREEEID  DGRKKVTIFF  GTQTGTAEGF  120
AKALGEEAKA  RYEKTRFKIV  DLDDYAADDD  EYEEKLKKED  VAFFFLATYG  DGEPTDNAAR  180
FYKWFTEGND  RGEWLKNLKY  GVFGLGNRQY  EHFNKVAKVV  DDILVEQGAQ  RLVQVGLGDD  240
DQCIEDDFTA  WREALWPELD  TILREEGDTA  VATPYTAAVL  EYRVSIHDSE  DAKFNDINMA  300
NGNGYTVFDA  QHPYKANVAV  KRELHTPESD  RSCIHLEFDI  AGSGLTYETG  DHVGVLCDNL  360
SETVDEALRL  LDMSPDTYFS  LHAEKEDGTP  ISSSLPPPFP  PCNLRTALTR  YACLLSSPKK  420
SALVALAAHA  SDPTEARLK   HLASPAGKDE  YSKWVVESQR  SLLEVMAEFP  SAKPPLGVFF  480
AGVAPRLQPR  FYSISSSPKI  AETRIHVTCA  LVYEKMPTGR  IHKGVCSTWM  KNAVPYEKSE  540
NCSSAPIFVR  QSNFKLPSDS  KVPIIMIGPG  TGLAPFRGFL  QERLALVESG  VELGPSVLFF  600
GCRNRRMDFI  YEEELQRFVE  SGALAELSVA  FSREGPTKEY  VQHKMMDKAS  DIWNMISQGA  660
YLYVCGDAKG  MARDVHRSLH  TIAQEQGSMD  STKAEGFVKN  LQTSGRYLRD  VW          712

SEQ ID NO: 30           moltype = AA   length = 713
FEATURE                 Location/Qualifiers
source                  1..713
                        mol_type =  protein
                        organism =  Arabidopsis thaliana
SEQUENCE: 30
MASSSSSSST  SMIDLMAAII  KGEPVIVSDP  ANASAYESVA  AELSSMLIEN  RQFAMIVTTS   60
IAVLIGCIVM  LVWRRSGSGN  SKRVEPLKPL  VIKPREEEID  DGRKKVTIFF  GTQTGTAEGF  120
AKALGEEAKA  RYEKTRFKIV  DLDDYAADDD  EYEEKLKKED  VAFFFLATYG  DGEPTDNAAR  180
FYKWFTEGND  RGEWLKNLKY  GVFGLGNRQY  EHFNKVAKVV  DDILVEQGAQ  RLVQVGLGDD  240
DQCIEDDFTA  WREALWPELD  TILREEGDTA  VATPYTAAVL  EYRVSIHDSE  DAKFNDITLA  300
```

```
NGNGYTVFDA QHPYKANVAV KRELHTPESD RSCIHLEFDI AGSGLTMKLG DHVGVLCDNL    360
SETVDEARL  LDMSPDTYFS LHAEKEDGTP ISSSLPPPFP PCNLRTALTR YACLLSSPKK    420
```
```
SETVDEARLRL LDMSPDTYFS LHAEKEDGTP ISSSLPPPFP PCNLRTALTR YACLLSSPKK   420
SALVALAAHA  SDPTEAERLK HLASPAGKDE YSKWVVESQR SLLEVMAEFP SAKPPLGVFF   480
AGVAPRLQPR  FYSISSSPKI AETRIHVTCA LVYEKMPTGR IHKGVCSTWM KNAVPYEKSE   540
KLFLGRPIFV  RQSNFKLPSD SKVPIIMIGP GTGLAPFRGF LQERLALVES GVELGPSVLF   600
FGCRNRRMDF  IYEEELQRFV ESGALAELSV AFSREGPTKE YVQHKMMDKA SDIWNMISQG   660
AYLYVCGDAK  GMARDVHRSL HTIAQEQGSM DSTKAEGFVK NLQTSGRYLR DVW          713

SEQ ID NO: 31              moltype =  length =
SEQUENCE: 31
000

SEQ ID NO: 32              moltype = AA   length = 708
FEATURE                    Location/Qualifiers
source                     1..708
                           mol_type = protein
                           organism = Stevia rebaudiana
SEQUENCE: 32
MAQSNSVKIS PLDLVTALFS GKVLDTSNAS ESGESAMLPT IAMIMENREL LMILTTSVAV    60
LIGCVVVLVW RRSSTKKSAL EPPVIVVPKR VQEEEVDDGK KKVTVFFGTQ TGTAEGFAKA    120
LVEEEAKARYE KAVFKVIDLD DYAADDDEYE EKLKKESLAF FFLATYGDGE PTDNAARFYK   180
WFTEGDAKGE WLNKLQYGVF GLGNRQYEHF NKIAKVVDQL LVEQGAKRLV PVGLGDDDQC    240
IEDDFTAWKE LVWPELDQLL RDEDDTTVAT PYTAAVAEYR VVFHEKPDAL SEDYSYTNGH    300
AVHDAQHPCR SNVAVKKELH SPESDRSCTH LEFDISNTGL SYETGDHVGV YCENLSEVVN    360
DAERLVGLPP DTYFSIHTDS EDGSPLGGAS LPPPFPPCTL RKALTCYADV LSSPKKSALL    420
ALAAHATDPS EADRLKFLAS PAGKDEYSQW IVASQRSLLE VMEAFPSAKP SLGVFFASVA    480
PRLQPRYYSI SSSPKMAPDR IHVTCALVYE KTPAGRIHKG VCSTWMKNAV PMTESQDCSW    540
APIYVRTSNF RLPSDPKVPV IMIGPGTGLA PFRGFLQERL ALKEAGTDLG LSILFFGCRN    600
RKVDFIYENE LNNFVETGAL SELIVAFSRE GPTKEYVQHK MSEKASDIWN LLSEGAYLYV    660
CGDAKGMAKD VHRTLHTIVQ EQGSLDSSKA ELYVKNLQMS GRYLRDVW                 708

SEQ ID NO: 33              moltype = AA   length = 705
FEATURE                    Location/Qualifiers
source                     1..705
                           mol_type = protein
                           organism = Artemisia annua
SEQUENCE: 33
MAQSTTSVKL SPFDLMTALL NGKVSFDTSN TSDTNIPLAV FMENRELLMI LTTSAVLIG     60
CVVVLVWRRS SSAAKKAAES PVIVVPKKVT EDEVDDGRKK VTVFFGTQTG TAEGFAKALV    120
EEEAKARYEKA VFKVIDLDDY AAEDDEYEEK LKKESLAFFF LATYGDGEPT DNAARFYKWF   180
TEGEEKGEWL DKLQYAVFGL GNRQYEHFNK IAKVVDEKLV EQGAKRLVPV GMGDDDQCIE    240
DDFTAWKELV WPELDQLLRD EDDTSVATPY TAAVAEYRVV FHDKPETYDQ DQLTNGHAVH    300
DAQHPCRSNV AVKKELHSPL SDRSCTHLEF DISNTGLSYE TGDHVGVYE NLSEVVDEAE    360
KLIGLPPHTY FSVHADNEDG TPLGGASLPP PFPPCTLRKA LASYADVLSS PKKSALLALA    420
AHATDSTEAD RLKFLASPAG KDEYAQWIVA SHRSLLEVME APPSAKPPLG VFFASVAPRL    480
QPRYYSISSS PRFAPNRIHV TCALVYEQTP SGRVHKGVCS TWMKNAVPMT ESQDCSWAPI    540
YVRTSNFRLP SDPKVPVIMI GPGTGLAPFR GFLQERLAQK EAGTELGTAI LFFGCRNRKV    600
DFIYEDELNN FVETGALSEL VTAFSREGAT KEYVQHKMTQ KASDIWNLLS EGAYLYVCGD    660
AKGMAKDVHR TLHTIVQEQG SLDSSKAELY VKNLQMAGRY LRDVW                    705

SEQ ID NO: 34              moltype = AA   length = 706
FEATURE                    Location/Qualifiers
source                     1..706
                           mol_type = protein
                           organism = Pelargonium graveolens
SEQUENCE: 34
MAQSSSGSMS PFDFMTAIIK GKMEPSNASL GAAGEVTAMI LDNRELVMIL TTSIAVLIGC    60
VVVFIWRRSS SQTPTAVQPL KPLLAKETES EVDDGKQKVT IFFGTQTGTA EGFAKALADE    120
AKARYDKVTF KVVDLDDYAA DDEEYEEKLK KETLAFFFLA TYGDGEPTDN AARFYKWFLE    180
GKERGEWLQN LKFGVFGLGN RQYEHFNKIA IVVDEILAEQ GGKRLISVGL GDDDQCIEDD    240
FTAWRESLWP ELDQLLRDED DTTVSTPYTA AVLEYRVVFH DPADAPTLEK SYSNANGHSV    300
VDAQHPLRAN VAVRRELHTP ASDRSCTHLE FDISGTGIAY ETGDHVGVYC ENLAETVEEA    360
LELLGLSPDT YFSVHADKED GTPLSGSSLP PPFPPCTLRK ALTLHADLLS SPKKSALLAL    420
AAHASDPTEA DRLRHLASPA GKDEYAQWIV ASQRSLLEVM AEFPSAKPPL GVFFASVAPR    480
LQPRYYSISS SPRIAPSRIH VTCALVYEKT PTGRVHKGVC STWMKNSVPS EKSDECSWAP    540
IFVRQSNFKL PADAKVPIIM IGPGTGLAPF RGFLQERLAL KEAGTELGPS ILFFGCRNSK    600
MDYIYEDELD NFVQNGALSE LVLAFSREGP TKEYVQHKMM EKASDIWNLI SQGAYLYVCG    660
DAKGMARDVH RTLHTIAQEQ GSLDSSKAES MVKNLQMSGR YLRDVW                   706

SEQ ID NO: 35              moltype = AA   length = 282
FEATURE                    Location/Qualifiers
source                     1..282
                           mol_type = protein
                           organism = Brachypodium distachyon
SEQUENCE: 35
MSAAAAVSSS SSPRLEGKVA LVTGGASGIG EAIVRLFRQH GAKVCIADVQ DEAGQQVRDS    60
LGDDAGTDVL FVHCDVTVEE DVSRAVDAAA EKFGTLDIMV NNAGITGDKV TDIRNLDFAE    120
VRKVFDINVH GMLLGMKHAA RVMIPGKKGS IVSLASVASV MGGMGPHAYT ASKHAVVGLT    180
KSVALELGKH GIRVNCVSPY AVPTALSMPH LPQGEHKGDA VRDFLAFVGG EANLKGVDLL    240
```

```
PKDVAQAVLY LASDEARYIS ALNLVVDGGF TSVNPNLKAF ED                           282

SEQ ID NO: 36            moltype = AA   length = 280
FEATURE                  Location/Qualifiers
source                   1..280
                         mol_type = protein
                         organism = Citrus sinensis
SEQUENCE: 36
MSNSNSTDSS PAVQRLVGRV ALITGGATGI GESTVRLFHK HGAKVCIADV QDNLGQQVCQ        60
SLGGEPDTFF CHCDVTKEED VCSAVDLTVE KFGTLDIMVN NAGISGAPCP DIREADLSEF        120
EKVFDINVKG VFHGMKHAAR IMIPQTKGTI ISICSVAGAI GGLGPHAYTG SKHAVLGLNK        180
NVAAELGKYG IRVNCVSPYA VATGLALAHL PEEERTEDAM VGFRNFVARN ANMQGTELTA        240
NDVANAVLFL ASDEARYISG TNLMVDGGFT SVNHSLRVFR                             280

SEQ ID NO: 37            moltype = AA   length = 280
FEATURE                  Location/Qualifiers
source                   1..280
                         mol_type = protein
                         organism = Citrus sinensis
SEQUENCE: 37
MATPPISSLI SQRLLGKVAL VTGGASGIGE GIVRLFHRHG AKVCFVDVQD ELGYRLQESL        60
VGDKDSNIFY SHCDVTVEDD VRRAVDLTVT KFGTLDIMVN NAGISGTPSS DIRNVDVSEF        120
EKVFDINVKG VFMGMKYAAS VMIPRKQGSI ISLGSVGSVI GGIGPHHYIS SKHAVVGLTR        180
SIAAELGQHG IRVNCVSPYA VPTNLAVAHL PEDERTEDMF TGFREFAKKN ANLQGVELTV        240
EDVANAVLFL ASEDARYISG DNLIVDGGFT RVNHSFRVFR                             280

SEQ ID NO: 38            moltype = AA   length = 262
FEATURE                  Location/Qualifiers
source                   1..262
                         mol_type = protein
                         organism = Citrus sinensis
SEQUENCE: 38
MSKPRLQGKV AIIMGAASGI GEATAKLFAE HGAFVIIADI QDELGNQVVS SIGPEKASYR        60
HCDVRDEKQV EETVAYAIEK YGSLDIMYSN AGVAGPVGTI LDLDMAQFDR TIATNLAGSV        120
MAVKYAARVM VANKIRGSII CTTSTASTVG GSGPHAYTIS KHGLLGLVRS AASELGKHGI        180
RVNCVSPFGV ATPFSAGTIN DVEGFVCKVA NLKGIVLKAK HVAEAALFLA SDESAYVSGH        240
DLVVDGGFTA VTNVMSMLEG HG                                                262

SEQ ID NO: 39            moltype = AA   length = 263
FEATURE                  Location/Qualifiers
source                   1..263
                         mol_type = protein
                         organism = Citrus sinensis
SEQUENCE: 39
MSNPRMEGKV ALITGAASGI GEAAVRLFAE HGAFVVAADV QDELGHQVAA SVGTDQVCYH        60
HCDVRDEKQV EETVRYTLEK YGKLDVLFSN AGIMGPLTGI LELDLTGFGN TMATNVCGVA        120
ATIKHAARAM VDKNIRGSII CTTSVASSLG GTAPHAYTTS KHALVGLVRT ACSELGAYGI        180
RVNCISPFGV ATPLSCTAYN LRPDEVEANS CALANLKGIV LKAKHIAEAA LFLASDESAY        240
ISGHNLAVDG GFTVVNHSSS SAT                                               263

SEQ ID NO: 40            moltype = AA   length = 278
FEATURE                  Location/Qualifiers
source                   1..278
                         mol_type = protein
                         organism = Citrus sinensis
SEQUENCE: 40
MTTAGSRDSP LVAQRLLGKV ALVTGGATGI GESIVRLFHK HGAKVCVVDI NDDLGQHLCQ        60
TLGPTTRFIH GDVAIEDDVS RAVDFTVANF GTLDIMVNNA GMGGPPCPDI REFPISTFEK        120
VFDINTKGTF IGMKHAARVM IPSKKGSIVS ISSVTSAIGG AGPHAYTASK HAVLGLTKSV        180
AAELGQHGIR VNCVSPYAIL TNLALAHLHE DERTDDARAG FRAFIGKNAN LQGVDLVEDD        240
VANAVLFLAS DDARYISGDN LFVDGGFTCT NHSLRVFR                               278

SEQ ID NO: 41            moltype = AA   length = 277
FEATURE                  Location/Qualifiers
source                   1..277
                         mol_type = protein
                         organism = Rhodococcus erythropolis
SEQUENCE: 41
MARVEGQVAL ITGAARGQGR SHAIKLAEEG ADVILVDVPN DVVDIGYPLG TADELDQTAK        60
DVENLGRKAI VIHADVRDLE SLTAEVDRAV STLGRLDIVS ANAGIASVPF LSHDIDPNTW        120
RQMIDINLTG VWHTAKVAVP HILAGERGGS IVLTSSAAGL KGYAQISHYS AAKHGVVGLM        180
RSLALELAPH RVRVNSLHPT QVNTPMIQNE GTYRIFSPDL ENPTREDFEI ASTTTNALPI        240
PWVESVDVSN ALLFLVSEDA RYITGAAIPV DAGTTLK                                277

SEQ ID NO: 42            moltype = AA   length = 279
FEATURE                  Location/Qualifiers
REGION                   1..279
                         note = Synthetic Sequence
source                   1..279
```

```
                        mol_type = protein
                        organism = synthetic construct
SEQUENCE: 42
MSTASSGDVS LLSQRLVGKV ALITGGATGI GESIARLFYR HGAKVCIVDI QDNPGQNLCR    60
ELGTDDACFF HCDVSIEIDV IRAVDFVVNR FGKLDIMVNK AGIADPPCPD IRNTDLSIFE   120
KVFDVNVKGT FQCMKHAARV MVPQKKGSII SLTSVASVIG GAGPHAYTGS KHAVLGLTKS   180
VAAELGLHGI RVNCVSPYAV PTGMPLAHLP ESEKTEDAMM GMRAFVGRNA NLQGIELTVD   240
DVANSVVFLA SDEARYVSGL NLMLDGGFSC VNHSLRVFR                          279

SEQ ID NO: 43           moltype = AA   length = 280
FEATURE                 Location/Qualifiers
source                  1..280
                        mol_type = protein
                        organism = Vitis vinifera
SEQUENCE: 43
MAATSIDNSP LPSQRLLGKV ALVTGGATGI GESIVRLFLK QGAKVCIVDV QDDLGQKLCD    60
TLGGDPNVSF FHCDVTIEDD VCHAVDFTVT KFGTLDIMVN NAGMAGPPCS DIRNVEVSMF   120
EKVFDVNVKG VFLGMKHAAR IMIPLKKGTI ISLCSVSSAI AGVGPHAYTG SKCAVAGLTQ   180
SVAAAEMGGHG IRVNCISPYA IATGLALAHL PEDERTEDAM AGFRAFVGKN ANLQGVELTV   240
DDVAHAAVFL ASDEARYISG LNLMLDGGFS CTNHSLRVFR                         280

SEQ ID NO: 44           moltype = AA   length = 267
FEATURE                 Location/Qualifiers
source                  1..267
                        mol_type = protein
                        organism = Zingiber zerumbet
SEQUENCE: 44
MRLEGKVALV TGGASGIGES IARLFIEHGA KICIVDVQDE LGQQVSQRLG GDPHACYFHC    60
DVTVEDDVRR AVDFTAEKYG TIDIMVNNAG ITGDKVIDIR DADFNEFKKV FDINVNGVFL   120
GMKHAARIMI PKMKGSIVSL ASVSSVIAGA GPHGYTGAKH AVVGLTKSVA AELGRHGIRV   180
NCVSPYAVPT RLSMPYLPES EMQEDALRGF LTFVRSNANL KGVDLMPNDV AEAVLYLATE   240
ESKYVSGLNL VIDGGFSIAN HTLQVFE                                       267

SEQ ID NO: 45           moltype = AA   length = 514
FEATURE                 Location/Qualifiers
source                  1..514
                        mol_type = protein
                        organism = unidentified
SEQUENCE: 45
MDAILNLQTV PLGTALTIGG PAVALGGISL WFLKEYVNDQ KRKSSNFLPP LPEVPGLPVI    60
GNLLQLTEKK PHKTFTNWAE TYGPIYSIKT GANTIVVLNT NELAKEAMVT RYSAISTRKL   120
TNALKILTCD KSIVAISDYD EFHKTVKRHV LTSVLGPNAQ KRHRIHRDTL IENVSKQLHD   180
LVRKYPNEAV NLRKIFQSEL FGLALKQALG KDIESIYVEG LDATLPREDV LKTLVLDIME   240
GAIDVDWRDF FPYLKWVPNK SFENRIQRKH LRREAVMKAL IMEQRKRINS GEKLNSYIDY   300
LSSEANTLTE KQILMLLWEA IIETSDTTVV STEWAMYELA KDPKRQEQLF LEIQNVCGSN   360
KITEEKLCQL PYLCAVFHET LRKHSPVPIV PLRYVHEDTQ LGGYHIPKGA EIAINIYGCN   420
RDKKVWESPE EWKPERFLDG KYDPVELQKT MAFGGGKRVC AGALQAMTIT CTTIARLIQE   480
FEWSLKDGEE ENVATMGLTT HKLHPMQAHI KPRK                               514

SEQ ID NO: 46           moltype = AA   length = 512
FEATURE                 Location/Qualifiers
source                  1..512
                        mol_type = protein
                        organism = Lactuca sativa
SEQUENCE: 46
MDGVIDMQTI PLRTAIAIGG TAVALVVALY FWFLRSYASP SHHSNHLPPV PEVPGVPVLG    60
NLLQLKEKKP YMTFTKWAEM YGPIYSIRTG ATSMVVVSSN EIAKEVVVTR FPSISTRKLS   120
YALKVLTEDK SMVAMSDYHD YHKTVKRHIL TAVLGPNAQK KFRAHRDTMM ENVSNELHAF   180
FEKNPNQEVN LRKIFQSQLF GLAMKQALGK DVESIYVKDL ETTMKREEIF EVLVVDPMMG   240
AIEVDWRDFF PYLKWVPNKS FENIIHRMYT RREAVMKALI QEHKKRIASG ENLNSYIDYL   300
LSEAQTLTDK QLLMSLWEPI IESSDTTMVT TEWAMYELAK NPNMQDRLYE EIQSVCGSEK   360
ITEENLSQLP YLYAVFQETL RKHCPVPIMP LRYVHENTVL GGYHVPAGTE VAINIYGCNM   420
DKKVWENPEE WNPERFLSEK ESMDLYKTMA FGGGKRVCAG SLQAMVISCI GIGRLVQDFE   480
WKLKDDAEED VNTLGLTTQK LHPLLALINP RK                                 512

SEQ ID NO: 47           moltype = AA   length = 513
FEATURE                 Location/Qualifiers
SITE                    307
                        note = misc_feature - Xaa can be any naturally occurring
                         amino acid
SITE                    356
                        note = misc_feature - Xaa can be any naturally occurring
                         amino acid
source                  1..513
                        mol_type = protein
                        organism = Cynara cardunculus
SEQUENCE: 47
MDMQSIPAIA IGSTAVAIAL GLFFWFFRRH VPDHIDHPNH LPSVPEVPGI PVLGNLLQLK    60
EKKPYMTFTK WAETYGPIYS IRTGAISMVV VSSNAIAKEA LVTRFPSIST RKLSKALEVL   120
```

```
TADKTMVAMS DYNDYHKTVK RHILTAVLGP NAQKKHRVHR DIMMQNLSNQ LHTFVQNSPQ   180
EEVNLRKVFQ SELFGLAMRQ TMGKDVESIY VEDLGTTMNR DEIFQVLVVD PLMGAIEVDW   240
RDFFPYLKWI PNRNFENTIQ QMYIRREAVM KALIQEHRKR IASGENLNSY IDYLLSEAQT   300
LSEKQLXMSL WEPIIESSDT TMVTTEWAMY ELAKNPKIQD RLYREIQGVC GSDKIXEENL   360
GQLPYLSAIF NETLRRHGPV PIIPLRYVHE DTELGGYHIP AGTQIAVNIY GCNMEKAVWE   420
NPEEWNPERF FEVEGDQKTM AFGGGKRVCA GSLQAMLIAC IGIGRMVQEF EWKLKDEAAQ   480
EDVNTLGLTT QKLRPLHAII YPRKENDAKV WKC                                513

SEQ ID NO: 48              moltype =    length =
SEQUENCE: 48
000

SEQ ID NO: 49              moltype = AA   length = 512
FEATURE                    Location/Qualifiers
source                     1..512
                           mol_type = protein
                           organism = Artemisia annua
SEQUENCE: 49
MDALTDMLQI PPATPITVAI TTVTIAVAIF LYIKSHASNH SRRSTHLPPV PEVPGVPVLG    60
NLLQLKEKKP YLTFTRWAQT YGAIYSIRTG ATSMVVVSSS EIAKEAMVTR FSSISTRNLS   120
KALTILTADK TMVAMSDYND YHRTVKRHIL TAMLGPNAQR KQRVHRDFMI ENISKQLHAF   180
VENSPKEEVD LRKIFQSELF GLAMKQAVGK DVESLNVEDL GVTMKRDEIF QVLVVDPMMG   240
AIEVDWRDFF PYLKWVPNKK FENTIQQMYI RRKAVMKALI KEHKKRIASG ENLNSYIDYL   300
LSEAQTFTDE QLIMSLWEPI IESSDTTMVT TEWAMYELAK NPKMQDRLYR DIQSVCGSDK   360
ITEENLSQLP YLSAIFHETL RRHSPVPIIP LRHVHEDTVL GGYHVPAGTE LAVNIYGCNM   420
EKNVWENPEE YNPDRFMKEN ETIDMQRTMA FGGGKRVCAG SLQAMLISCI GIGRMVQEFE   480
WRFKDKAEED INTLGLTTQR LNPLRAIIKP RN                                 512

SEQ ID NO: 50              moltype = AA   length = 511
FEATURE                    Location/Qualifiers
source                     1..511
                           mol_type = protein
                           organism = Helianthus annuus
SEQUENCE: 50
MDALTGMLPI PPATALAIGG TAIALAVAIS FWFLRSYTSG ESNRLPRVPE VPGVPVLGNL    60
LQLKEKKPYM TFTRWAETYG PIYSIRTGAT SMVVVSSNEI AKEAVTRFE SISTRNLSKA   120
LKILTDDKTM VAMSDYNDYH KTVKRHILTA MLGPNAQKKH RIQRDIMMEN LSNRLHAFVK   180
TSTEQEEVDL REIFQSELFG LAMRQTMGKD VESIYVEDLK ITMKRDEIFQ VLVVDPMMGA   240
IDVDWRDFFP YLKWVPNKKF ENTIQQMYIR REAVMKALIK QHKERIASGE KLNSYIDYLL   300
SEAQSLTDRQ LLMSVWEPII ESSDTTMVTT EWAIYELAKN PHIQDRLYRD IQSVCGSDII   360
KEEHLSQLPF ITAIFHETLR RHSPVPIIPL RYVHEDTVLG GYHVPAGTEL AINIYGCNME   420
KSVWENPEEW NPERFMKENE TIDFQKTMAF GGGKRVCAGS LQAMLISCVG IGRMVQEFKW   480
ELKNKAQEEV NTIGLTTQML RPLRAIIKPR N                                  511

SEQ ID NO: 51              moltype = AA   length = 505
FEATURE                    Location/Qualifiers
REGION                     1..505
                           note = Synthetic Sequence
source                     1..505
                           mol_type = protein
                           organism = synthetic construct
SEQUENCE: 51
MAWEYALIGL VVGIIIGAVA MRWYLKSYTS ARRSQSNHLP RVPEVPGVPL LGNLLQLKEK    60
KPYMTFTKWA ATYGPIYSIK TGATSVVVVS SNEIAKEALV TRFQSISTRN LSKALKVLTA   120
DKQMVAMSDY DDYHKTVKRH ILTAVLGPNA QKKHRIHRDI MMDNISTQLH EFVKNNPEQE   180
EVDLRKIFQS ELFGLAMRQA LGKDVESLYV EDLKITMNRD EILQVLVVDP MMGAIDVDWR   240
DFFPYLKWVP NKKFENTIQQ MYIRREAVMK SLIKEQKKRI ASGEKLNSYI DYLLSEAQTL   300
TDQQLLMSLW EPIIESSDTT MVTTEWAMYE LAKNPKLQDR LYRDIKSVCG SEKITEEHLS   360
QLPYITAIFH ETLRKHSPVP LPLRHVHED TVLGGYHVPA GTELAVNIYG CNMDKNVWEN   420
PEEWNPERFM KENETIDFQK TMAFGGGKRV CAGSLQALLI ASIGIGRMVQ EFEWKLKDMT   480
QEEVNTIGLT NQMLRPLRAI IKPRI                                         505

SEQ ID NO: 52              moltype = AA   length = 492
FEATURE                    Location/Qualifiers
REGION                     1..492
                           note = Synthetic Sequence
source                     1..492
                           mol_type = protein
                           organism = synthetic construct
SEQUENCE: 52
MAKPPLFFIV IIGLIVVAAS FLYKLLTRPT SSKNRLPEPW RLPIIGHMHH LIGTMPHRGV    60
MDLARKYGSL MHLQLGEVSA IVVSSPKWAK EILTTYDIPF ANRPETLTGE IIAYHNTDIV   120
LAPYGEYWRQ LRKLCTLELL SVKKVKSFQS LREEECWNLV QEIKASGSGT PFNLSEGIFK   180
VIATVLSRAA FGKGIKDQKQ FTEIVKEILR ETGGFDVADI FPSKKFLHHL SGKRGRLTSI   240
HNKLDSLINN LVAEHTVSKS SKVNETLLDV LLRLKNSEEF PLTADNVKAI ILDMFGAGTD   300
TSSATVEWAI SELIRCPRAM EKVQAELRQA LNGKERIKEE EIQDLPYLNL VIRETLRLHP   360
PLPLVMPREC RQAMNLAGYD VANKTKLIVN VFAINRDPEY WKDAESFNPE RFENSNTTIM   420
GADYEYLPFG AGRRMCPGSA LGLANVQLPL ANILYYFKWK LPNGASHDQL DMTESFGATV   480
QRKTELMLVP SF                                                       492
```

```
SEQ ID NO: 53           moltype = AA  length = 709
FEATURE                 Location/Qualifiers
source                  1..709
                        mol_type = protein
                        organism = Camptotheca acuminata
SEQUENCE: 53
MAQSSSVKVS TFDLMSAILR GRSMDQTNVS FESGESPALA MLIENRELVM ILTTSVAVLI   60
GCFVVLLWRR SSGKSGKVTE PPKPLMVKTE PEPEVDDGKK KVSIFYGTQT GTAEGFAKAL  120
AEEAKVRYEK ASFKVIDLDD YAADDEEYEE KLKKETLTFF FLATYGDGEP TDNAARFYKW  180
FMEGKERGDW LKNLHYGVFG LGNRQYEHFN RIAKVVDDTI AEQGGKRLIP VGLGDDDQCI  240
EDDFAAWREL LWPELDQLLQ DEDGTTVATP YTAAVLEYRV VFHDSPDASL LDKSFSKSNG  300
HAVHDAQHPC RANVAVRREL HTPASDRSCT HLEFDISGTG LVYETGDHVG VYCENLIEVV  360
EEEAEMLLGLS PDTFFSIHTD KEDGTPLSGS SLPPPFPPCT LRRALTQYAD LLSSPKKSSL  420
LALAAHCSDP SEADRLRHLA SPSGKDEYAQ WVVASQRSLL EVMAEFPSAK PPIGAFFAGV  480
APRLQPRYYS ISSSPRMAPS RIHVTCALVF EKTPVGRIHK GVCSTWMKNA VPLDESRDCS  540
WAPIFVRQSN FKLPADTKVP VLMIGPGTGL APFRGFLQER LALKEAGAEL GPAILFFGCR  600
NRQMDYIYED ELNNFVETGA LSELIVAFSR EGPKKEYVQH KMMEKASDIW NMISQEGYIY  660
VCGDAKGMAR DVHRTLHTIV QEQGSLDSSK TESMVKNLQM NGRYLRDVW             709

SEQ ID NO: 54           moltype = AA  length = 516
FEATURE                 Location/Qualifiers
REGION                  1..516
                        note = Synthetic Sequence
source                  1..516
                        mol_type = protein
                        organism = synthetic construct
SEQUENCE: 54
MAQDLRLILI IVGAIAIIAL LVHGFLLIKR SSRSSVHKQQ VLLASLPPSP PRLPLIGNIH   60
QLVGGNPHRI LLQLARTHGP LICLRLGQVD QVVASSVEAV EEIIKRHDLK FADRPRDLTF  120
SRIFFYDGNA VVMTPYGGEW KQMRKIYAME LLNSRRVKSF AAIREDVARK LTGEIAHKAF  180
AQTPVINLSE MVMSMINAIV IRVAFGDKCK QQAYFLHLVK EAMSYVSSFS VADMYPSLKF  240
LDTLTGLKSK LEGVHGKLDK VFDEIIAQRQ AALAAEQAEE DLIIDVLLKL KDEGNQEFPI  300
TYTSVKAIVM EIFLAGTETS SSVIDWVMSE LIKNPKAMEK VQKEMREAMQ GKTKLEESDI  360
PKFSYLNLVI KETLRLHPPG PLLFPRECRE TCEVMGYRVP AGARLLINAF ALSRDEKYWG  420
SDAESFKPER FEGISVDFKG SNFEFMPFGA GRRICPGMTF GISSVEVALA HLLFHFDWQL  480
PQGMKIEDLD MMEVSGMSAT RRSPLLVLAK LIIPLP                           516

SEQ ID NO: 55           moltype = AA  length = 510
FEATURE                 Location/Qualifiers
REGION                  1..510
                        note = Synthetic Sequence
source                  1..510
                        mol_type = protein
                        organism = synthetic construct
SEQUENCE: 55
MAQDLRLILI IVGAIAIIAL LVHGFLKSAV TKPKLNLPPG PWTLPLIGSI HHIVSNPLPY   60
RAMKLAHKH GPLMMLWLGE VPTLVVSSPE AAQAITKTHD VSFADRHINS TVDILTFNGM  120
DMVFGSYGEQ WRQLRKLSVL ELLSAARVQS FQRIREEEVA RFMRSLAASA SAGATVDLSK  180
MISSFINDTF VRESIGSRCK YQDEYLAALD TAIRVAAELS VGNIFPSSRV LQSLSTARRK  240
AIASRDEMAR ILGQIIRETK ESMDQGDKTS NESMISVLLR LQKDAGLPIE LTDNVVMALM  300
FDLFGAGSDT SSTTLTWCMT ELVRYPATMA KAQAEVREAF KGKTTITEDD LSTANLRYLK  360
LVVKEALRLH CPVPLLLPRK CREACQVMGY DIPKGTCVPV NVWAICRDPR YWEDAEEFKP  420
ERFENSNLDY KGTYYEYLPF GSGRRMCPGA NLGVANLELA LASLLYHFDW KLPSGQEPKD  480
VDVWEAAGLV AKKNIGLVLH PVSHIAPVNA                                  510

SEQ ID NO: 56           moltype = AA  length = 511
FEATURE                 Location/Qualifiers
REGION                  1..511
                        note = Synthetic Sequence
source                  1..511
                        mol_type = protein
                        organism = synthetic construct
SEQUENCE: 56
MAQDLRLILI IVGAIAIIAL LVHGFFLLRK WKNSNSQSKK LPPGPWKLPL LGSMLHMVGG   60
LPHHVLRDLA KKYGPLMHLQ LGEVSAVVVT SPDMAKEVLK THDIAFASRP KLLAPEIVCY  120
NRSDIAFCPY GDYWRQMRKI CVLEVLSAKN VRSFSSIRRD EVLRLVNFVR SSTSEPVNFT  180
ERLFLFTSSM TCRSAFGKVF KEQETFIQLI KEVIGLAGGF DVADIPSLK FLHVLTGMEG  240
KIMKAHHKVD AIVEDVINEH KKNLAMGKTN GALGGEDLID VLLRLMNDGG LQFPITNDNI  300
KAIIFDMFAA GTETSSSTLV WAMVQMMRNP TILAKAQAEV REAFKGKETF DENDVEELKY  360
LKLVIKETLR LHPPVPLLVP RECREETEIN GYTIPVKTKV MVNVWALGRD PKYWDDADNF  420
KPERFEQCSV DFIGNNFEYL PFGGGRRICP GISFGLANVY LPLAQLLYHF DWKLPTGMEP  480
KDLDLTELVG ITIARKSDLM LVATPYQPSR E                                511
```